US010865186B2

(12) United States Patent
Duarte et al.

(10) Patent No.: US 10,865,186 B2
(45) Date of Patent: Dec. 15, 2020

(54) OPIOID AGONISTS AND USES THEREOF

(71) Applicant: Nektar Therapeutics, San Francisco, CA (US)

(72) Inventors: Franco J. Duarte, Walnut Creek, CA (US); Neel K. Anand, San Mateo, CA (US); Pankaj Sharma, New Delhi (IN); Devendrapratap Singh, Mumbai (IN)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 16/109,456

(22) Filed: Aug. 22, 2018

(65) Prior Publication Data

US 2018/0362468 A1 Dec. 20, 2018

Related U.S. Application Data

(60) Division of application No. 15/603,942, filed on May 24, 2017, now Pat. No. 10,081,602, which is a continuation of application No. 15/039,686, filed as application No. PCT/IN2014/000739 on Nov. 27, 2014, now Pat. No. 9,688,638.

(30) Foreign Application Priority Data

Nov. 27, 2013 (IN) ............................ 3456/DEL/2013
Feb. 13, 2014 (IN) ............................. 401/DEL/2014

(51) Int. Cl.
*C07D 221/26* (2006.01)
*C07D 513/08* (2006.01)
*C07D 401/12* (2006.01)

(52) U.S. Cl.
CPC ......... *C07D 221/26* (2013.01); *C07D 401/12* (2013.01); *C07D 513/08* (2013.01)

(58) Field of Classification Search
CPC .................................................. C07D 221/26
USPC ......................................................... 546/74
See application file for complete search history.

(56) References Cited

U.S. PATENT DOCUMENTS

| | | | | |
|---|---|---|---|---|
| 9,688,638 B2* | 6/2017 | Duarte | ................. | C07D 221/26 |
| 9,815,824 B2* | 11/2017 | Anand | ................. | C07C 233/40 |
| 10,081,602 B2* | 9/2018 | Duarte | ................. | C07D 221/26 |
| 2003/0187009 A1 | 10/2003 | Wentland | | |
| 2005/0136031 A1 | 6/2005 | Bentley et al. | | |
| 2010/0048602 A1* | 2/2010 | Riggs-Sauthier | .... | A61K 31/439 |
| | | | | 514/282 |
| 2017/0022167 A1 | 1/2017 | Duarte et al. | | |
| 2017/0253565 A1 | 9/2017 | Duarte et al. | | |

FOREIGN PATENT DOCUMENTS

| | | |
|---|---|---|
| DE | 2127819 | 1/1972 |
| WO | WO 02/098949 A1 | 12/2002 |
| WO | WO 2013/070617 A1 | 5/2013 |
| WO | WO 2013/167963 A1 | 11/2013 |

OTHER PUBLICATIONS

Mikhail, Biomacromolecules (2010), 11(5), 1273-80.*
Dorwald F. A. Side Reactions in Organic Synthesis, 2005, Wiley: VCH, Weinheim p. IX of Preface p. 1-15.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Venkatesh, J. Pharm. Sci. 89, 145-54 (2000) (p. 146, left column).*
Chen et al., "Synthesis and Properties of ABA Amphiphiles", J. Org. Chem., vol. 64, pp. 6870-6873, (1999).
Ertl et al., "Fast Calculation of Molecular Polar Surface Area as a Sum of Fragment-Based Contributions and Its Application to the Prediction of Drug Transport Properties", J. Med. Chem., vol. 43, pp. 3714-3717, (2000).
Karra et al., "Sar and evaluation of novel 5H-benzo[c][1,8]naphthyridin-6-one analogs as Aurora kinase inhibitors", Bioorganic & Medicinal Chemistry Letters, vol. 23, pp. 3081-3087, (2013).
Kelder et al., "Polar Molecular Surface as a Dominating Determinant for Oral Absorption and Brain Penetration of Drugs", Pharmaceutical Research, vol. 16, No. 10, pp. 1514-1519, (1999).
Rubin, "The Cell Biology of the Blood-Brain Barrier", Annu. Rev. Neurosci., vol. 22, pp. 11-28, (1999).
Shiyama, et al., "Design and synthesis of novel hydrophilic spacers for the reduction of nonspecific binding proteins on affinity resins", Bioorganic & Medicinal Chemistry, vol. 12, pp. 2831-2841, (2004).
Summerfield et al., "Central Nervous System Drug Disposition: the Relationship between in Situ Brain Permeability and Brain Free Fraction", the Journal of Pharmacology and Experimental Therapeutics, vol. 322, No. 1, pp. 205-213, (2007).
Tsuji, "Small Molecular Drug Transfer across the Blood-Brain Barrier via Carrier-Mediated Transport Systems", NeuroRx: The Journal of the American Society for Experimental NeuroTherapeutics, vol. 2, pp. 54-62, (Jan. 2005).
Wentland, et al., "Syntheses and Opioid Receptor Binding Affinities of 8-Amino-2,6-methano-3-benzazocines", J. Med. Chem., vol. 46, pp. 838-849, (2003).
Wentland et al., "Syntheses and opioid receptor binding properties of carboxamido-substituted opioids", Bioorganic & Medicinal Chemistry Letters, vol. 19, pp. 203-208, (2009).
International Search Report and Written Opinion in PCT Application No. PCT/IN2014/000739 dated Mar. 19, 2015.
International Preliminary Report on Patentability in PCT Application No. PCT/IN2014/000739 dated Jun. 9, 2016.
Enzon Pharmaceuticals, Macromolecular Engineering Technologies, 16 pages, (2004).

(Continued)

*Primary Examiner* — Nizal S Chandrakumar
(74) *Attorney, Agent, or Firm* — Jacqueline F. Mahoney

(57) ABSTRACT

Provided are compounds, including those of Formula I; and pharmaceutically acceptable salts and solvates thereof. The compounds described herein relate to and/or have application(s) in (among others) the fields of drug discovery, pharmacotherapy, physiology, organic chemistry and polymer chemistry.

11 Claims, No Drawings

(56) References Cited

OTHER PUBLICATIONS

Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003-$1^{st}$, (Jan. 2003).
NOF Corporation, PEG Derivatives, Phospholipid and Drug Delivery Materials for Pharmaceuticals, 27 pages, Catalogue 2003-$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PET™ (dPEG™) derivatives, (Product Catalog), 26 pages, (Updated: Jul. 18, 2005).
Quanta Biodesign, Ltd., Leading innovator, producer and provider of monodisperse discrete PET™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Examination Report in European Patent Application No. 14 837 046.3-1462 dated Jul. 18, 2017.

\* cited by examiner

OPIOID AGONISTS AND USES THEREOF

This application is a divisional of U.S. patent application Ser. No. 15/603,942, filed May 24, 2017, now U.S. Pat. No. 10,081,602, which is a continuation of U.S. patent application Ser. No. 15/039,686, filed May 26, 2016, now U.S. Pat. No. 9,688,638, which is a 35 U.S.C. § 371 application of International Application No. PCT/IN2014/000739, filed Nov. 27, 2014, designating the United States, which claims the benefit of priority to Indian Patent Application No. 401/DEL/2014, filed Feb. 13, 2014, and to Indian Patent Application No. 3456/DEL/2013, filed Nov. 27, 2013, the disclosures of which are all incorporated herein by reference in their entireties.

The present disclosure relates to novel compounds and to their use as agonists of the kappa opioid receptor, the mu opioid receptor, or mixed agonists of both receptors. The disclosure also relates to methods for preparation of the compounds and to pharmaceutical compositions containing such compounds. The compounds described herein relate to and/or have application(s) in (among others) the fields of drug discovery, pharmacotherapy, physiology, organic chemistry and polymer chemistry.

Opioid agonists, such as morphine, have long been used to treat patients suffering from pain. Opioid agonists exert their analgesic and other pharmacological effects through interactions with opioid receptors, of which there are three main classes: mu (μ) receptors, kappa (κ) receptors, and delta (δ) receptors. Many of the clinically used opioid agonists are relatively selective for mu receptors, although opioid agonists typically have agonist activity at other opioid receptors (particularly at increased concentrations).

Pharmacologically, opioid agonists represent an important class of agents employed in the management of pain. Opioid agonists currently used in analgesia, however, contain considerable addictive properties that complicate and limit their use in therapeutic practice. The medical, social and financial complications arising from opioid abuse impose severe constraints on the ability of physicians to prescribe opioids for use in chronic pain.

Kappa opioid agonists that exhibit full agonist properties at the kappa opioid receptor have been widely shown to be efficacious in preclinical models of pain, particularly visceral pain. Kappa opioid agonists are understood to lack several of the side effects of mu opioid agonists, including abuse liability, gastrointestinal transit inhibition and respiratory depression. Kappa opioid agonists, however, are understood to produce complicating CNS mediated side effects, such as dysphoria and sedation at analgesic doses. As a result, the presence of these side effects has hindered the development of selective kappa opioid agonists as clinically useful analgesics.

Mixed mu and kappa opioid agonist that exhibit full agonist properties at the respective opioid receptors have also been shown to be efficacious in preclinical models of pain, including visceral pain. However, despite the combined analgesic properties a mixed mu and kappa opioid agonists may demonstrate, they are understood to produce several side effects related to both mu and kappa opioid receptor mechanisms, including abuse liability, respiratory depression, gastrointestinal transit inhibition, sedation and dysphoria.

Beyond analgesia, kappa agonists have shown anti-inflammatory effects in vivo. Additionally, asimadoline, a kappa opioid agonist that is moderately restricted to the periphery, is currently undergoing studies for the treatment of irritable bowel syndrome. Due to its limited CNS entry, asimadoline may reduce the extent of side effects associated with less restricted kappa agonists, though studies are still ongoing. Additional known kappa opioid agonists, such as enadoline and spiradoline, enter the CNS (Central Nervous System) causing dysphoria, and may have contributed to not being developed clinically. Further, while mixed agonists (acting on kappa and mu receptors) have been marketed, including pentazocine, to date, no full kappa agonist has been approved for use in humans for the treatment of pain.

The incorporation of a poly(ethylene glycol) moiety into a small molecule scaffold has been utilized to modify the rate of CNS entry of several classes of molecules. See U.S. Patent Application Publication No. 2005/0136031 and U.S. Patent Application Publication No. 2010/0048602. The sites of incorporation and further modifications to the molecules, however, have differing effects on the overall activity and pharmacological properties of the resulting molecule.

In view of the above, there remains a need for peripherally acting opioid agonists that retain sufficient efficacy to treat visceral pain and other symptoms or disease states associated with the opioid receptor, while reducing the CNS side effects. The present invention seeks to address these and other needs.

In one or more embodiments, a compound selected from the formula:

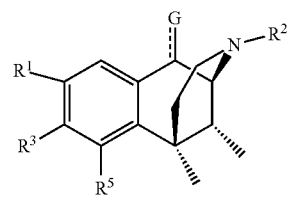

Formula I wherein:

$R^1$ is selected from hydrogen, optionally substituted alkyl, optionally substituted aryl, and X-POLY;

$R^3$ is selected from hydroxyl, optionally substituted alkyl, optionally substituted amino, optionally substituted heterocyclyl, and —X-POLY;

$R^5$ is selected from hydrogen and —X-POLY;

or $R^1$ and $R^3$ are taken together with their intervening atoms to form a fused, optionally substituted heteroaryl or optionally substituted heterocyclyl; or $R^3$ and $R^5$ are taken together with their intervening atoms to form a fused, optionally substituted heteroaryl;

$R^2$ is selected from optionally substituted alkyl and —X-POLY;

--- is optionally a single bond or a double bond;

G is —O—$R^4$ or —NH—$R^4$ when --- represents a single bond, or G is =O or =N—$R^4$ when --- represents a double bond;

X is a spacer moiety and is preferably selected from a covalent bond, —NHC(O)—, —NH—, and —O—;

POLY is a water soluble, non-peptidic oligomer; and $R^4$ is -L-POLY or —X-POLY, wherein L is an optional amino acid residue, provided that one of $R^1$, $R^2$, $R^3$, $R^4$, and $R^5$ comprises a POLY group; and pharmaceutically acceptable salts and solvates thereof.

In certain embodiments of Formula I, $R^1$ is selected from hydrogen, optionally substituted alkyl, optionally substituted aryl, and —X-POLY; $R^2$ is selected from optionally substituted alkyl and —X-POLY; $R^3$ is selected from hydroxyl, optionally substituted alkyl, optionally substituted amino, optionally substituted heterocyclyl, and —X-POLY; or R$^1$ and R$^3$ are taken together with their intervening atoms to form a fused, optionally substituted heteroaryl or optionally substituted heterocyclyl; or R$^3$ and R$^5$ are taken together with their intervening atoms to form a fused, optionally substituted heteroaryl; --- is optionally a single bond or a double bond; G is —O—R$^4$ or NH—R$^4$ when --- represents a single bond or G is =O or =N—R$^4$ when --- represents a double bond; X is selected from a covalent bond, —NHC(O)—, —NH—, and —O—; POLY is a water soluble, non-peptidic oligomer; R$^4$ is -L-POLY or —X-POLY, wherein L is an optional amino acid residue; R$^5$ is selected from hydrogen and —X-POLY; provided one of R$^1$, R$^2$, R$^3$, R$^4$, and R$^5$ comprises a POLY group; and pharmaceutically acceptable salts and solvates thereof.

In one or more embodiments of the invention, a composition is provided, the composition comprising (i) a compound as described herein, and, optionally, (ii) a pharmaceutically acceptable excipient.

In one or more embodiments of the invention, a composition of matter is provided, the composition of matter comprising a compound as described herein, wherein the compound is present in a dosage form.

In one or more embodiments of the invention, a method is provided, the method comprising administering a compound as described herein to a patient in need thereof.

Additional embodiments of the present compounds, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

As used in this specification, the singular forms "a," "an," and "the" include plural referents unless the context clearly dictates otherwise.

In describing and claiming the present invention, the following terminology will be used in accordance with the definitions described below.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like. As used herein, "lower alkyl" refers to an alkyl group having from 1 to 6 carbon atoms. Specific examples of lower alkyl include, but are not limited to, methyl, ethyl, n-propyl, iso-propyl, n-butyl, iso-butyl, t-butyl, n-hexyl, and the like.

The term "substituted alkyl" refers to an alkyl group having 1 to 5 substituents (in certain embodiments 1, 2, or 3) selected from alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxyl, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)— heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R is alkyl, aryl or heteroaryl and n is 0, 1, or 2. "Substituted lower alkyl" refers to a lower alkyl group defined above, substituted as defined for alkyl.

The term "alkylene" refers to a diradical of a branched or unbranched saturated hydrocarbon chain, in certain embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like. The term "lower alkylene" refers to a diradical of a branched or unbranched saturated hydrocarbon chain, in certain embodiments, having 1, 2, 3, 4, 5 or 6 carbon atoms.

The terms "substituted alkylene" and "substituted lower alkylene" refer to an alkylene group or lower alkylene group as defined above having 1 to 5 substituents (in certain embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in certain embodiments, from 2 to 10 carbon atoms, e.g. 2 to 6 carbon atoms) and having from 1 to 6 carbon-carbon double bonds, e.g. 1, 2 or 3 carbon-carbon double bonds. In certain embodiments, alkenyl groups include ethenyl (or vinyl, i.e. —CH=CH$_2$), 1-propylene (or allyl, i.e. —CH$_2$CH=CH$_2$), isopropylene (—C(CH$_3$)=CH$_2$), and the like. The term "lower alkenyl" refers to alkenyl as defined above having from 2 to 6 carbon atoms.

The term "substituted alkenyl" refers to an alkenyl group as defined above having 1 to 5 substituents (in certain embodiments, 1, 2, or 3 substituents) as defined for substituted alkyl.

The term "substituted lower alkenyl" refers to a lower alkenyl group as defined above having 1 to 5 substituents (in certain embodiments, 1, 2, or 3 substituents) as defined for substituted alkyl.

The term "alkenylene" refers to a diradical of a branched or unbranched unsaturated hydrocarbon group having from 2 to 20 carbon atoms (in certain embodiments, from 2 to 10 carbon atoms, e.g. 2 to 6 carbon atoms) and having from 1 to 6 carbon-carbon double bonds, e.g. 1, 2, or 3 carbon-carbon double bonds.

The term "alkynyl" refers to a monoradical of an unsaturated hydrocarbon, in certain embodiments, having from 2 to 20 carbon atoms (in certain embodiments, from 2 to 10 carbon atoms, e.g. 2 to 6 carbon atoms) and having from 1 to 6 carbon-carbon triple bonds e.g. 1, 2, or 3 carbon-carbon triple bonds. In certain embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in certain embodiments, 1, 2, or 3 substituents) as defined for substituted alkyl.

The term "alkynylene" refers to a diradical of an unsaturated hydrocarbon, in certain embodiments, having from 2 to 20 carbon atoms (in certain embodiments, from 2 to 10 carbon atoms, e.g. 2 to 6 carbon atoms) and having from 1 to 6 carbon-carbon triple bonds e.g. 1, 2, or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In certain embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like. The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is optionally substituted alkylene and Z is substituted alkenyl or substituted alkynyl, where substituted alkyl, substituted alkenyl and substituted alkynyl are as defined herein.

The term "C$_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In certain embodiments, C$_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, and 3-fluoropropyl.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in certain embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in certain embodiments, 1, 2 or 3 substituents), selected from alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)— heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl.

The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

As used herein, "—X-POLY" refers to a water-soluble, nonpeptidic oligomer POLY attached through a linker "X".

"Water soluble oligomer" indicates a non-peptidic oligomer that is at least 35% (by weight) soluble, preferably greater than 70% (by weight), and more preferably greater than 95% (by weight) soluble, in water at room temperature. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. In certain embodiments, the oligomers used in connection with present the invention are homo-oligomers. The water-soluble oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 1 to about 50 monomers, preferably from about 1 to about 30 monomers. In certain embodiments, an "oligomer" is a molecule possessing from about 2 to about 50 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or any polyethylene glycol is one in which substantially all (preferably all) monomeric subunits are ethylene oxide subunits, though, the oligomer may contain distinct end capping moieties or functional groups, e.g., for providing a site of covalent modification or reaction with another compound. PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. For the PEG oligomers, the variable (n) ranges from about 1 to 50, and the terminal groups and architecture of the overall PEG can vary. When PEG further comprises a functional group, A, for linking to, e.g., a small molecule, the functional group when covalently attached to a PEG oligomer does not result in formation of an oxygen-oxygen bond (—O—O—, a peroxide linkage).

The terms "end-capped" or "terminally capped" are interchangeably used herein to refer to a terminal or endpoint of an oligomer having an end-capping moiety. Typically, although not necessarily, the end-capping moiety comprises a hydroxy or $C_{1-20}$ alkoxy group. Thus, examples of end-capping moieties include alkoxy (e.g., methoxy, ethoxy and benzyloxy), as well as aryl, alkyl, heteroaryl, cyclo, heterocyclo, and the like. Further examples include $C_{1-3}$ haloalkyl and carboxy. In addition, saturated, unsaturated, substituted and unsubstituted forms of each of the foregoing are envisioned. Moreover, the end-capping group can also be a silane. The end-capping group can also comprise a detectable label. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

In the context of describing the consistency of oligomers in a given composition, "substantially" or "essentially" means nearly totally or completely, for instance, 95% or greater, in certain embodiments 97% or greater, in certain embodiments 98% or greater, in certain embodiments 99% or greater, and in certain embodiments 99.9% or greater.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). In certain embodiments, a monodisperse oligomer composition possesses a MW/Mn value of 1.0005 or less, and in certain embodiments, a MW/Mn value of 1.0000. By extension, a composition comprised of monodisperse compounds means that substantially all oligomers of all compounds in the composition have a single and definable number (as a whole number) of monomers rather than a distribution and would possess a MW/Mn value of 1.0005, and in certain embodiments, a MW/Mn value of 1.0000 if the oligomer were not attached to a compound of the present invention. A composition comprised of monodisperse compounds can include, however, one or more substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. In certain embodiments, for a bimodal oligomer composition as described herein, each peak is generally symmetric about its mean, although the size of the two peaks may differ. Ideally, the polydispersity index of each peak in the bimodal distribution, Mw/Mn, is 1.01 or less, in certain embodiments 1.001 or less, in certain embodiments 1.0005 or less, and in certain embodiments a MW/Mn value of 1.0000. By extension, a composition comprised of bimodal compounds means that substantially all oligomers of all compounds in the composition have one of two definable and different numbers (as whole numbers) of monomers rather than a large distribution and would possess a MW/Mn value of 1.01 or less, in certain embodiments 1.001 or less, in certain embodiments 1.0005 or less, and in certain embodiments a MW/Mn value of 1.0000 if the oligomer were not attached to a compound of the present invention. A composition comprised of bimodal compounds can include, however, one or more substances such as solvents, reagents, excipients, and so forth.

"Branched", in reference to the geometry or overall structure of an oligomer, refers to an oligomer having two or more oligomers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

As used herein "X" is a spacer moiety including a covalent bond or a group of 1-20 atoms. X may include, but is not limited to optionally substituted alkylene, optionally substituted alkenylene, optionally substituted alkynylene, optionally substituted alkoxy, hydroxyl, optionally substituted amino, optionally substituted aryl, optionally substituted heterocyclyl, optionally substituted heteroaryl, optionally substituted ester, alkyl amine, dialkyl amine, keto, optionally substituted acyl, aminocarbonyl, carboxyalkyl, acyloxy, acylamino, alkoxycarbonylamino, aminocarbonylamino, and the like. It is understood that the spacer X will comprise diradicals of the respective groups. Exemplary spacer moieties include a covalent bond, —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —NH—C(O)—CH$_2$—O—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—, —O—C(O)—NH—CH$_2$—, —O—C(O)—NH—CH$_2$—CH$_2$—, —NH—CH$_2$—CH$_2$—, —CH$_2$—NH—CH$_2$—, —CH$_2$CHOHCH$_2$NH—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C (O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—C(O)—NH—CH$_2$—CH$_2$—NH—C(O)—CH$_2$—, a bivalent cycloalkyl group, amino, substituted amino. Additional spacers include, acylamino, acyl, aryloxy, alkylene, amino, substituted amino, piperidino, and pyrrolidino. For purposes of the present invention, however, a group of atoms is not considered a spacer when it is immediately adjacent to an oligomeric segment, and the group of atoms is the same as a monomer of the oligomer such that the group would represent a mere extension of the oligomer chain.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In certain embodiments, aryls include phenyl, fluorenyl, naphthyl, anthryl, and the like.

Unless otherwise constrained by the definition for the aryl substituent, such aryl groups can optionally be substituted with 1, 2, 3, 4, or 5 substituents (In certain embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In certain embodiments, the "heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in certain embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl." The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in certain embodiments, 1, 2, or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, amino carbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —X-POLY, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2, or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$. The term "substituted amino" refers to the group —NRR where each R is independently selected from the group consisting of hydrogen, alkyl, —X-POLY, cycloalkyl, aryl, heteroaryl and heterocyclyl provided that both R groups are not hydrogen, or a group —Y—Z, in which Y is optionally substituted alkylene and Z is alkenyl, cycloalkenyl or alkynyl. Unless otherwise constrained by the definition, all substituents may optionally be further substituted by 1, 2, or 3 substituents chosen from alkyl, alkenyl, alkynyl, —X-POLY, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1, or 2.

The term "alkyl amine" refers to —NHR in which R is optionally substituted alkyl.

The term "dialkyl amine" refers to —NRR in which each R is independently an optionally substituted alkyl.

The term "cyano" refers to the group —CN.

The term "azido" refers to a group N=N=N.

The term "keto" or "oxo" refers to a group =O.

The term "carboxy" or "carboxyl" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, —X-POLY, cyano or —S(O)$_n$R$^a$, in which R$^a$ is alkyl, aryl or heteroaryl and n is 0, 1, or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "carboxyalkyl" refers to the groups —C(O)O-alkyl or —C(O)O— cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "alkoxycarbonylamino" refers to the group —N(R$^d$)C(O)OR in which R is alkyl and R$^d$ is hydrogen or alkyl. Unless otherwise constrained by the definition, each alkyl may optionally be further substituted by 1, 2, or 3 substituents selected from alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "aminocarbonylamino" refers to the group —NR$^c$C(O)NRR, wherein R$^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2, or 3 substituents selected from the group consisting of alkyl, alkenyl, alkynyl, carboxy, carboxyalkyl, aminocarbonyl, hydroxy, alkoxy, halogen, CF$_3$, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)₂NRR, wherein each R is independently hydrogen, alkyl, cycloalkyl, aryl, heteroaryl or heterocyclyl. Unless otherwise constrained by the definition, all substituents may optionally be further substituted by 1, 2, or 3 substituents selected from alkyl, alkenyl, alkynyl, carboxy, carboxyalkyl, aminocarbonyl, hydroxy, alkoxy, halogen, CF₃, amino, substituted amino, —X-POLY, cyano, cycloalkyl, heterocyclyl, aryl, heteroaryl, and —S(O)$_n$R$^a$, in which R$^a$ is alkyl, aryl or heteroaryl and n is 0, 1, or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

The term "amino acid residue" refers to an amino acid that is altered by the presence of one or more bonds that are not present in the parent amino acid. An example of a glycine residue is provided below:

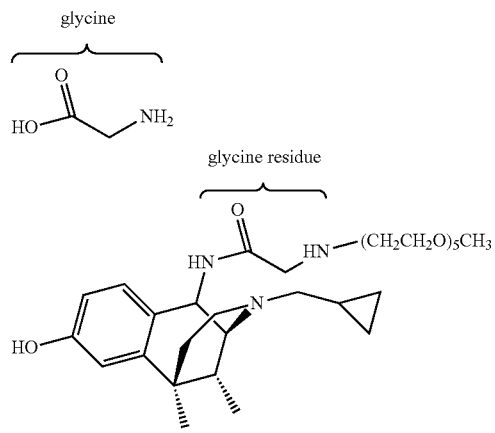

Exemplary amino acid residues include residues of alanine, valine, leucine, isoleucine, glycine, threonine, serine, cysteine, methionine, tyrosine, phenylalanine, tryptophan, aspartic acid, glutamic acid, lysine, arginine, histidine, proline, and non-naturally occurring amino acids. Included in this definition are both the representative L-amino acids and D-amino acids.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. In certain contexts the term "biological membrane" does not include those membranes associated with the middle gastrointestinal tract (e.g., stomach and small intestines) For example, in some instances it may be desirable for a compound of the invention to have a limited ability to cross the blood-brain barrier, yet be desirable that the same compound cross the middle gastro-intestinal tract.

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

"Pharmacologically effective amount," "physiologically effective amount," and "therapeutically effective amount" are used interchangeably herein to mean the amount of a compound of the present invention alone or present in a composition that is needed to provide a threshold level of the compound in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

The term "patient," refers to a living organism suffering from or prone to a condition that can be prevented or treated by administration of a compound as described herein, and includes both humans and animals.

The compounds of the invention, if chiral, may be in a racemic mixture, or an optically active form, for example, a single optically active enantiomer, or any combination or ratio of enantiomers (i.e., scalemic mixture). In addition, the compound may possess one or more geometric isomers. With respect to geometric isomers, a composition can comprise a single geometric isomer or a mixture of two or more geometric isomers. A compound for use in the present invention can be in its customary active form, or may possess some degree of modification.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

The term "pharmaceutically acceptable salt" refers to non-toxic salts of the compounds of this invention. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Also included are salts with acidic amino acid such as aspartate and glutamate. Base addition salts include alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or solvates.

The term "solvate" refers to a complex formed by the combining of a compound of the present invention and a solvent.

The term "hydrate" refers to the complex formed by the combining of a compound of the present invention and water.

Selected substituents comprising the compounds of Formula I may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

In some instances, names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of certain compounds of the disclosure is illustrated with a representative compound of the formula

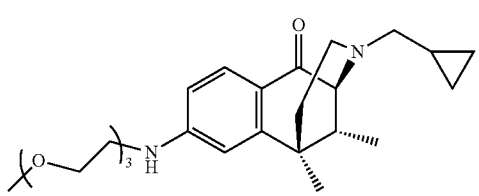

which is named (6R,11R)-3-(Cyclopropylmethyl)-8-({2-[2-(2-methoxy)ethoxy]ethyl}amino-6.11-dimethyl-3,4,5,6-tetrahydro-2,6-methano-3-benzazocin-1(2H)-one.

In some instances, names of compounds of the present disclosure are provided using the chemical naming functionality of ChemBioDraw Ultra (Cambridgesoft, Waltham, Mass., Version 12.0) (e.g. Examples 1-28). Other compounds or radicals may be named with common names or systematic or non-systematic names. The naming and numbering of certain compounds of the disclosure is illustrated with a representative compound of the formula

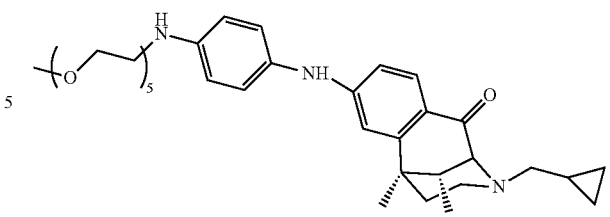

which is named: (2S,6R,11R)-8-((4-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one.

In certain embodiments, a compound is selected from the formula:

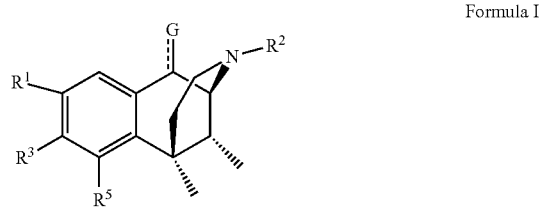

Formula I wherein:
$R^1$ is selected from hydrogen, optionally substituted alkyl, optionally substituted aryl, and —X-POLY; $R^2$ is selected from optionally substituted alkyl and —X-POLY; $R^3$ is selected from hydroxyl, optionally substituted alkyl, optionally substituted amino, optionally substituted heterocyclyl, and —X-POLY; or $R^1$ and $R^3$ are taken together with their intervening atoms to form a fused, optionally substituted heteroaryl or optionally substituted heterocyclyl; or $R^3$ and $R^5$ are taken together with their intervening atoms to form a fused, optionally substituted heteroaryl; ⸺ is optionally a single bond or a double bond; G is —O—$R^4$ or —NH—$R^4$ when ⸺ represents a single bond or G is =O when ⸺ represents a double bond; X is selected from for example, a covalent bond, —C(O)—, —NHC(O)—, —NH—, —CH$_2$CHOHCH$_2$NH—, and —O—; POLY is a water soluble, non-peptidic oligomer; $R^4$ is -L-POLY or —X-POLY, wherein L is an optional amino acid residue; $R^5$ is selected from hydrogen and —X-POLY; provided one of $R^1$, $R^2$, $R^3$, $R^4$, and $R^5$ comprises a POLY group; and pharmaceutically acceptable salts and solvates thereof.

In certain embodiments of a compound of Formula I, $R^5$ is hydrogen.

In certain embodiments of a compound of Formula I, $R^2$ is alkyl.

In certain embodiments of a compound of Formula I, $R^2$ is cyclopropylmethyl.

In certain embodiments of a compound of Formula I, G is —O— and ⸺ represents a double bond.

In certain embodiments of a compound of Formula I, $R^1$ is hydrogen.

In certain embodiments of a compound of Formula I, $R^3$ is selected from optionally substituted alkyl, optionally substituted amino, and —X-POLY.

In certain embodiments of a compound of Formula I, $R^3$ is optionally substituted amino.

In certain embodiments of a compound of Formula I, $R^3$ is amino substituted with an optionally substituted aryl or optionally substituted alkyl.

In certain embodiments of a compound of Formula I, $R^3$ is amino substituted with an optionally substituted phenyl.

In certain embodiments, the compound of Formula I is selected from a compound of the formula

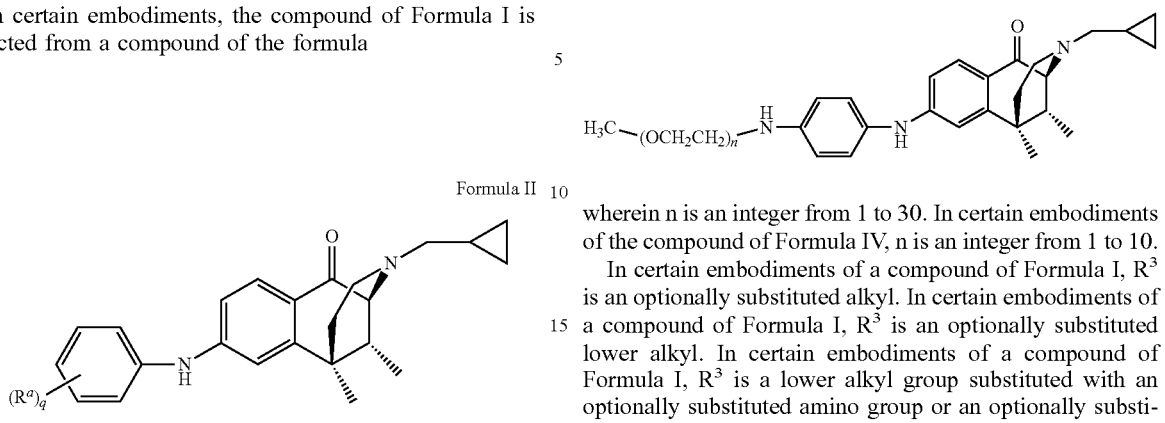

Formula II wherein q is an integer from 1 to 3; each $R^a$ is independently selected from optionally substituted amino, halo, optionally substituted alkyl, and —X-POLY; X is selected from a covalent bond, —NH— or —O—; POLY is a water soluble, non-peptidic oligomer; and wherein only one $R^a$ is X-POLY.

In certain embodiments of the compound of Formula II, q is 1.

In certain embodiments of the compound of Formula II, X is —NH—. In certain embodiments of the compound of Formula II, X is —O—.

In certain embodiments of the compound of Formula II, POLY is a poly(alkylene oxide) oligomer. In certain embodiments of the compound of Formula II, POLY is a poly(ethylene oxide) oligomer. In certain embodiments of the compound of Formula II, POLY is capped with an optionally substituted alkyl. In certain embodiments of the compound of Formula II, POLY is capped with a methyl, trifluoromethyl, or methyl substituted with a carboxy group.

In certain embodiments, the compound of Formula I or Formula II is selected from a compound of the formula

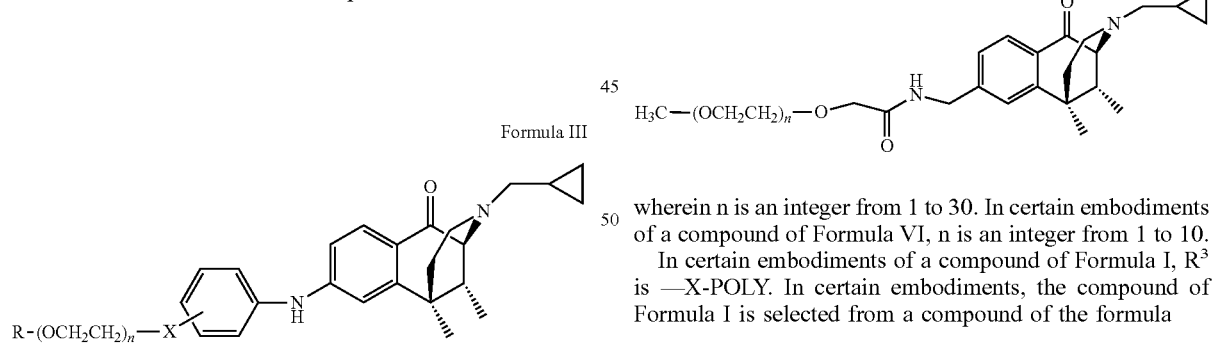

Formula III wherein R is selected from methyl, trifluoromethyl, and methyl substituted with a carboxy group; n is an integer from 1 to 30; and X is selected from —O— or —NH—.

In certain embodiments of the compound of Formula III, X is —O—. In certain embodiments of the compound of Formula III, X is —NH—.

In certain embodiments of the compound of Formula III, n is an integer from 1 to 10.

In certain embodiments, the compound of Formula I, II, or III is selected from a compound of the formula

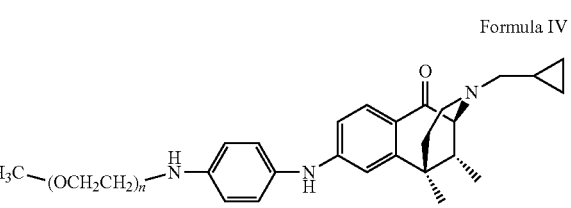

Formula IV wherein n is an integer from 1 to 30. In certain embodiments of the compound of Formula IV, n is an integer from 1 to 10.

In certain embodiments of a compound of Formula I, $R^3$ is an optionally substituted alkyl. In certain embodiments of a compound of Formula I, $R^3$ is an optionally substituted lower alkyl. In certain embodiments of a compound of Formula I, $R^3$ is a lower alkyl group substituted with an optionally substituted amino group or an optionally substituted acylamino group.

In certain embodiments, the compound of Formula I is selected from a compound of the formula

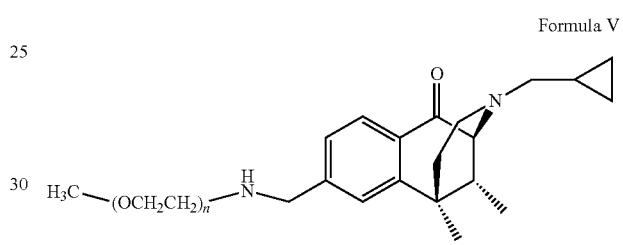

Formula V wherein n is an integer from 1 to 30. In certain embodiments of a compound of Formula V, n is an integer from 1 to 10.

In certain embodiments, the compound of Formula I is selected from a compound of the formula

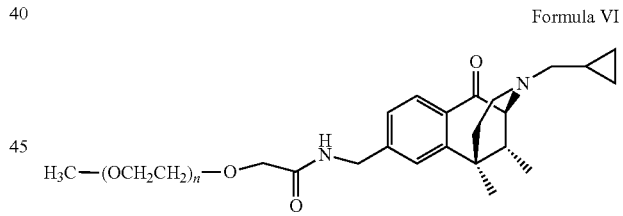

Formula VI wherein n is an integer from 1 to 30. In certain embodiments of a compound of Formula VI, n is an integer from 1 to 10.

In certain embodiments of a compound of Formula I, $R^3$ is —X-POLY. In certain embodiments, the compound of Formula I is selected from a compound of the formula

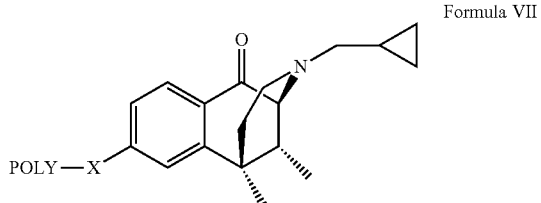

Formula VII wherein X is selected from —O—, —CH$_2$CHOHCH$_2$NH—, —NHC(O)—, and —NH—; and POLY is a poly(alkylene oxide) oligomer. In certain embodiments of a compound of Formula VII, X is —O—. In certain embodiments of a compound of Formula VII, X is —NH—. In certain embodiments of a compound of Formula VII, X is —NHC(O)—. In certain embodiments of a compound of Formula VII, X is —CH₂CHOHCH₂NH—. In certain embodiments the compound of Formula VII is selected from a compound of the formula Formula VIII wherein X is selected from —O—, —NHC(O)—, —CH₂CHOHCH₂NH—, and —NH—; and n is an integer from 1 to 30. In certain embodiments of a compound of Formula VIII, n is an integer from 1 to 10.

In certain embodiments of a compound of Formula I, $R^1$ and $R^3$ are taken together with their intervening atoms to form a fused, optionally substituted heteroaryl or optionally substituted heterocyclyl. In certain embodiments of a compound of Formula I, $R^1$ and $R^3$ are taken together with their intervening atoms to form a fused, optionally substituted heteroaryl. In certain embodiments of a compound of Formula I, $R^1$ and $R^3$ are taken together with their intervening atoms to form a fused, optionally substituted heterocyclyl. In certain embodiments of a compound of Formula I, the heteroaryl or heterocyclyl is substituted with an optionally substituted amino group. In certain embodiments the compound of Formula I is selected from a compound of the formula:

Formula IX wherein n is an integer from 1 to 30. In certain embodiments of a compound of Formula IX, n is an integer from 1 to 10.

In certain embodiments of a compound of Formula I, $R^3$ is OH.

In certain embodiments of a compound of Formula I, $R^3$ is OH and $R^1$ is selected optionally substituted alkyl, optionally substituted aryl, and —X-POLY. In certain embodiments of a compound of Formula I, $R^1$ is optionally substituted lower alkyl. In certain embodiments of a compound of Formula I, $R^1$ is optionally substituted methyl. In certain embodiments the compound of Formula I is selected from a compound of the formula Formula X wherein n is an integer from 1 to 30. In certain embodiments of a compound of Formula X, n is 1 to 10.

In certain embodiments of a compound of Formula I, $R^1$ is selected from phenyl substituted with 1 to 3 substituents chosen from halo and —X-POLY. In certain embodiments of a compound of Formula I, $R^1$ is selected from phenyl substituted with 1 to 3 substituents chosen from halo and —X-POLY and $R^3$ is hydroxyl. In certain embodiments of a compound of Formula I, $R^1$ is selected from phenyl substituted with 1 to 3 substituents chosen from halo and —O—(CH₂CH₂O)$_n$CH₃, where n is an integer from 1 to 30.

In certain embodiments the compound of Formula I is selected from a compound of the formula:

Formula XI wherein n is an integer from 1 to 30. In certain embodiments of a compound of Formula XI, n is an integer from 1 to 10.

In certain embodiments of a compound of Formula I, $R^3$ is OH and $R^5$ is X-POLY. In certain embodiments the compound of Formula I, is selected from a compound of the formula:

XII wherein X is selected from —O— and —NH—, and n is an integer from 1 to 30. In certain embodiments of a compound of Formula XII, n is 1 to 10. In certain embodiments X is —O—. In certain embodiments, X is —NH—.

In certain embodiments of a compound of Formula I, $R^2$ is —X-POLY. In certain embodiments of a compound of Formula I, G is —O— and ⹀ is a double bond. In certain embodiments of a compound of Formula I, $R^1$ is hydrogen. In certain embodiments of a compound of Formula I, $R^5$ is hydrogen. In certain embodiments of a compound of Formula I, $R^3$ is —OH.

In certain embodiments the compound of Formula I, is selected from a compound of the formula:

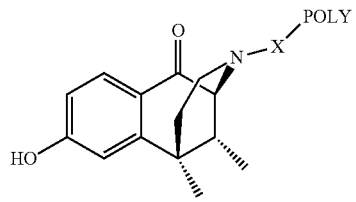

Formula XIII wherein X is selected from a covalent bond and —C(O)—; and POLY is a poly(alkylene oxide) oligomer.

In certain embodiments of a compound of Formula I, the compound is selected from a compound of the formula:

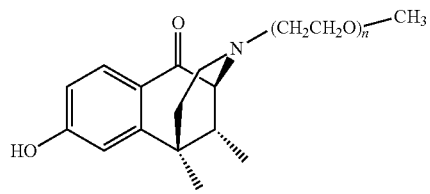

Formula XIV wherein n is an integer from 1 to 30. In certain embodiments of a compound of Formula XIV, n is an integer from 1 to 10.

In certain embodiments of a compound of Formula I, ⹀ is a single bond. In certain embodiments of a compound of Formula I, $R^1$ is hydrogen. In certain embodiments of a compound of Formula I, $R^2$ is cyclopropylmethyl. In certain embodiments of a compound of Formula I, $R^3$ is —OH. In certain embodiments of a compound of Formula I, $R^5$ is hydrogen. In certain embodiments the compound of Formula I is selected from a compound of the formula:

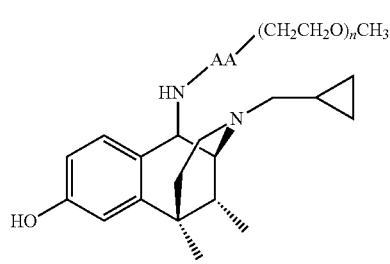

XV wherein AA is an amino acid residue; and n is an integer from 1 to 30. In certain embodiments of a compound of Formula XV, AA is a glycine residue. In certain embodiments of a compound of Formula XV, n is 1 to 10.

In certain embodiments of a compound of Formula I, $R^3$ is amino substituted with a substituted lower alkyl.

In certain embodiments, the compound of Formula I is selected from a compound of the formula

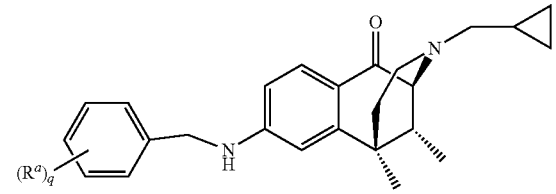

Formula XVI wherein q is an integer from 1 to 3; each $R^a$ is independently selected from optionally substituted amino, halo, optionally substituted alkyl, and —X—$(CH_2CH_2O)_n$$CH_3$; X is selected from a covalent bond, —NH— or —O—; and n is an integer from 1 to 30; wherein one $R^a$ is —X—$(CH_2CH_2O)_n$$CH_3$. In certain embodiments of a compound of Formula XVI, n is 1 to 10. In certain embodiments of a compound of Formula XVI, q is 1. In certain embodiments of a compound of Formula XV, X is —O—.

In certain embodiments, the compound of Formula XVI is selected from a compound of the formula

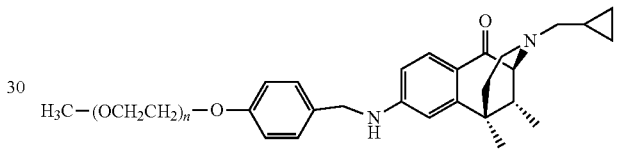

Formula XVII wherein n is an integer from 1 to 30. In certain embodiments of a compound of Formula XVII, n is an integer from 1 to 10.

In certain embodiments of a compound of Formula I, $R^3$ is an optionally substituted heterocyclyl. In certain embodiments of a compound of Formula I, $R^3$ is a heterocyclyl substituted with —X-POLY. In certain embodiments of a compound of Formula I, $R^3$ is a piperazinyl group substituted with —X-POLY. In certain embodiments, the compound of Formula I is selected from a compound of the formula

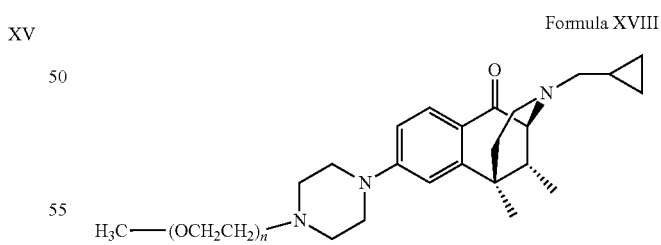

Formula XVIII wherein n is 1 to 30. In certain embodiments of a compound of Formula XVIII, n is 1 to 10.

In certain embodiments of a compound of Formula I, $R^3$ and $R^5$ are taken together with their intervening atoms to form a fused, optionally substituted heteroaryl. In certain embodiments of a compound of Formula I, the heteroaryl is substituted with an optionally substituted amino group. In certain embodiments the compound of Formula I is selected from a compound of the formula:

Formula XIX

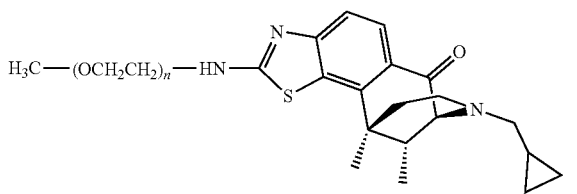

wherein n is an integer from 1 to 30. In certain embodiments of a compound of Formula XIX, n is an integer from 1 to 10.

In certain embodiments of a compound of Formula I, the compound is selected from a compound of the formula Formula XX

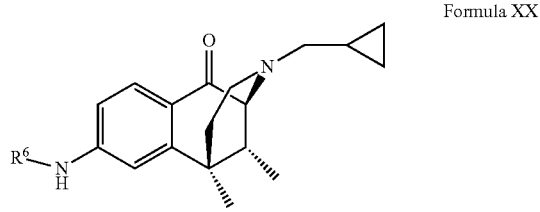

wherein $R^6$ is an optionally substituted alkyl or an optionally substituted heterocyclyl. In certain embodiments, $R^6$ is an optionally substituted lower alkyl. In certain embodiments, $R^6$ is a lower alkyl substituted with 1 to 5 substituents selected from hydroxyl, lower alkoxy, halogen, and lower alkyl. In certain embodiments, $R^6$ is an isopropyl or t-butyl group, substituted with 1 to 3 hydroxyl groups. In certain embodiments of a compound of Formula XX, $R^6$ is an optionally substituted heterocyclyl. In certain embodiments, $R^6$ is a heterocyclyl substituted with —X—(CH$_2$CH$_2$O)$_n$CH$_3$; wherein X is selected from a covalent bond, —NH— or —O—; and n is an integer from 1 to 30. In certain embodiments, $R^6$ is a piperidinyl group substituted with —X—(CH$_2$CH$_2$O)$_n$CH$_3$; wherein X is selected from a covalent bond, —NH— or —O—; and n is an integer from 1 to 30. In certain embodiments, $R^6$ is a piperidinyl group substituted with —X—(CH$_2$CH$_2$O)$_n$CH$_3$; wherein X is a covalent bond; and n is an integer from 1 to 10. In certain embodiments, the substituted heterocyclyl group is a substituted piperidin-4-yl.

In certain embodiments of a compound of Formula I, --- is a single bond. In certain embodiments of a compound of Formula I, $R^1$ is hydrogen. In certain embodiments of a compound of Formula I, $R^2$ is cyclopropylmethyl. In certain embodiments of a compound of Formula I, $R^3$ is —OH. In certain embodiments of a compound of Formula I, $R^5$ is hydrogen. In certain embodiments the compound of Formula I is selected from a compound of the formula:

XXI

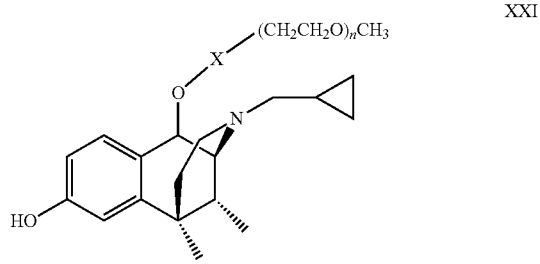

wherein X is a covalent bond; and n is an integer from 1 to 30. In certain embodiments, n is an integer from 1 to 10.

In certain embodiments, the compound of Formula I is selected from (2S,6R,11R)-3-(Cyclopropylmethyl)-8-({2-[2-(2-methoxy)ethoxy]ethyl}amino-6,11-dimethyl-3,4,5,6-tetrahydro-2,6-methano-3-benzazocin-1(2H)-one;

(2S,6R,11R)-3-(Cyclopropylmethyl)-6,11-dimethyl-8-(2,5,8,11,14-pentaoxahexadecan-16-ylamino)-3,4,5,6-tetrahydro-2,6-methano-3-benzazocin-1(2H)-one;

(2S,6R,11R)-3-(Cyclopropylmethyl)-8-(2,5,8,11,14,17,20-heptaoxadocosan-22-ylamino)-6,11-dimethyl-3,4,5,6-tetrahydro-2,6-methano-3-benzazocin-1(2H)-one;

(2S,6R,11R)-3-(Cyclopropylmethyl)-8-{2-[2-(2-methoxyethoxy)ethoxy]ethoxy}-6,11-dimethyl-3,4,5,6-tetrahydro-2,6-methano-3-benzazocin-1(2H)-one;

(2S,6R,11R)-3-(Cyclopropylmethyl)-6,11-dimethyl-8-(2,5,8,11,14-pentaoxahexadecan-16-ylamino)-3,4,5,6-tetrahydro-2,6-methano-3-benzazocin-1(2H)-one;

(2S,6R,11R)-3-(Cyclopropylmethyl)-8-(2,5,8,11,14,17,20-heptaoxadocosan-22-yloxy)-6,11-dimethyl-3,4,5,6-tetrahydro-2,6-methano-3-benzazocin-1(2H)-one;

(2S,6R,11R)-8-((2-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one;

(2S,6R,11R)-8-((3-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one;

(2S,6R,11R)-8-((4-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one;

(2S,6R,11R)-8-((4-(2,5,8,11,14-pentaoxahexadecan-16-ylamino)phenyl)amino)-3 (cyclopropylmethyl)-6,11-dimethyl-3,4,5,6-tetrahydro-2,6-methanobenzo[d]azocin-1(2H)-one;

(2S,6R,11R)-8-((3-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one;

(2S,6R,11R)-8-((4-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one;

(6S,10R,12R)-2-(2,5,8,11,14-pentaoxahexadecan-16-ylamino)-7-(cyclopropylmethyl)-10,12-dimethyl-7,8,9,10-tetrahydro-6,10-methanothiazolo[4',5':4,5]benzo[1,2-d]azocin-5(6H)-one;

(2S,6R,11R)-8-hydroxy-3-(2-(2-methoxyethoxy)ethyl)-6,11-dimethyl-3,4,5,6-tetrahydro-2,6-methanobenzo[d]azocin-1(2H)-one;

N-((2S,6R,11R)-3-(cyclopropylmethyl)-6,11-dimethyl-1-oxo-1,2,3,4,5,6-hexahydro-2,6-methanobenzo[d]azocin-8-yl)-2-(2-methoxyethoxy)acetamide;

(2S,6R,11R)-3-(cyclopropylmethyl)-N-(2-methoxyethyl)-6,11-dimethyl-1-oxo-1,2,3,4,5,6-hexahydro-2,6-methanobenzo[d]azocine-8-carboxamide;

N,N-(((2S,6R,11R)-3-(cyclopropylmethyl)-6,11-dimethyl-1-oxo-1,2,3,4,5,6-hexahydro-2,6-methanobenzo[d]azocin-8-yl)methyl)-2-(2-methoxyethoxy)acetamide;

(2S,6R,11R)-3-(cyclopropylmethyl)-8-(((2-(2-methoxyethoxy) ethyl)amino)methyl)-6,11-dimethyl-3,4,5,6-tetrahydro-2,6-methanobenzo[d]azocin-1(2H)-one;

(2S,6R,11R)-7-(2,5,8,11,14-pentaoxahexadecan-16-yloxy)-3-(cyclopropylmethyl)-8-hydroxy-6,11-dimethyl-3,4,5,6-tetrahydro-2,6-methanobenzo[d]azocin-1(2H)-one;

(2S,6R,11R)-3-(cyclopropylmethyl)-6,11-dimethyl-8-((4-((1,1,1-trifluoro-2,5,8,11,14-pentaoxahexadecan-16-yl)amino)phenyl)amino)-3,4,5,6-tetrahydro-2,6-methanobenzo[d]azocin-1(2H)-one;

(2S,6R,11R)-3-(cyclopropylmethyl)-8-((16-(hydroxymethyl)-2,5,8,11,14-pentaoxaheptadecan-17-yl)amino)-6,11-dimethyl-3,4,5,6-tetrahydro-2,6-methanobenzo[d]azocin-1(2H)-one;

(7S,11R,12R)-2-(2,5,8,11,14-pentaoxahexadecan-16-ylamino)-8-(cyclopropylmethyl)-11,12-dimethyl-8,9,10,11-tetrahydro-7,11-methanothiazolo[5',4':3,4]benzo[1,2-d]azocin-6(7H)-one;

(2S,6R,11R)-3-(cyclopropylmethyl)-8-((1-hydroxy-2-methylpropan-2-yl)amino)-6,11-dimethyl-3,4,5,6-tetrahydro-2,6-methanobenzo[d]azocin-1(2H)-one;

(2S,6R,11R)-3-(cyclopropylmethyl)-8-((1,3-dihydroxypropan-2-yl)amino)-6,11-dimethyl-3,4,5,6-tetrahydro-2,6-methanobenzo[d]azocin-1(2H)-one;

(1R,2S,6R,11R)-1-(2,5,8,11,14-pentaoxahexadecan-16-yloxy)-3-(cyclopropylmethyl)-6,11-dimethyl-1,2,3,4,5,6-hexahydro-2,6-methanobenzo[d]azocin-8-ol;

(2S,6R,11R)-7-(2,5,8,11,14-pentaoxahexadecan-16-ylamino)-3-(cyclopropylmethyl)-8-hydroxy-6,11-dimethyl-3,4,5,6-tetrahydro-2,6-methanobenzo[d]azocin-1(2H)-one;

(2S,6R,11R)-3-(cyclopropylmethyl)-8-((1-(2-methoxyethyl)piperidin-4-yl)amino)-6,11-dimethyl-3,4,5,6-tetrahydro-2,6-methanobenzo[d]azocin-1(2H)-one; and (2S,6R,11R)-3-(cyclopropylmethyl)-8-(4-(2-(2-(2-methoxyethoxy)ethoxy)ethyl) piperazin-1-yl)-6,11-dimethyl-3,4,5,6-tetrahydro-2,6-methanobenzo[d]azocin-1(2H)-one, and pharmaceutically acceptable salts thereof.

The compounds of the present invention may be prepared using techniques known to one of skill in the art. As disclosed herein, each compound of Formula I comprises at least one —X-POLY group. The incorporation of the —X-POLY group into a compound of Formula I can be achieved by reacting a synthetic precursor/synthetic intermediate of a compound of Formula I with a POLY group having a functional group that is capable of reacting with a functional group on the synthetic intermediate to compound of Formula I. The synthetic intermediate of a compound of Formula I may in certain embodiments possess a group suitable for covalent attachment of the oligomer. Such groups include, but are not limited to, a free hydroxyl, carboxyl, carbonyl, thio, amino group, or the like. Such groups can be incorporated into the synthetic intermediate to provide a point of attachment for the oligomer. As such, the oligomer can be incorporated at various stages of the synthesis, depending on the synthetic scheme. The introduction and conversion of functional groups in a synthetic intermediate are transformations that are generally known to those of skill in the art and can be found in the relevant texts. See e.g. M. Smith, *March's Advanced Organic Chemistry: Reactions, Mechanisms and Structure*, ($7^{th}$ ed. 2013); Carey and Sundberg, *Advanced Organic Chemistry*, ($5^{th}$ ed. 2007).

The group "X" adjacent to POLY in the compound of Formula I is typically formed by reaction of a functional group on a terminus of the oligomer (or one or more monomers when it is desired to "grow" the oligomer onto the compound of the present invention) with a corresponding functional group within synthetic precursor/intermediate to a compound of Formula I. For example, an amino group on an oligomer may be reacted with a carboxylic acid or an activated carboxylic acid derivative on the intermediate, or vice versa, to produce an amide linkage. Alternatively, reaction of an amine on an oligomer with an activated carbonate (e.g. succinimidyl or benzotriazyl carbonate) on the intermediate, or vice versa, forms a carbamate linkage. Reaction of an amine on an oligomer with an isocyanate (R—N=C=O) on an intermediate, or vice versa, forms a urea linkage (R—NH—(C=O)—NH—R'). Further, reaction of an alcohol (alkoxide) group on an oligomer with an alkyl halide, or halide group within an intermediate, or vice versa, forms an ether linkage. In yet another approach, an intermediate having an aldehyde function is coupled to an oligomer amino group by reductive amination, resulting in formation of a secondary amine linkage between the oligomer and the compound (or intermediate thereof) of the present invention.

Accordingly, each "POLY" (oligomer) is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where in certain embodiments, alkyl is methyl; α-hydroxy acid, such as lactic acid or glycolic acid; phosphazene, oxazoline, amino acids, carbohydrates such as monosaccharides, saccharide or mannitol; and N-acryloylmorpholine. In certain embodiments, monomer types include alkylene oxide, olefinic alcohol, hydroxyalkyl methacrylamide or methacrylate, N-acryloylmorpholine, and α-hydroxy acid. In certain embodiments, each oligomer is, independently, a co-oligomer of two monomer types selected from this group, or, in certain embodiments, is a homo-oligomer of one monomer type selected from this group.

The two monomer types in a co-oligomer may be of the same monomer type, for example, two alkylene oxides, such as ethylene oxide and propylene oxide. In certain embodiments, the oligomer is a homo-oligomer of ethylene oxide. Usually, although not necessarily, the terminus (or termini) of the oligomer that is not covalently attached to a compound (or intermediate thereof) of the present invention is capped to render it unreactive. Alternatively, the terminus may include a reactive group. When the terminus is a reactive group, the reactive group is either selected such that it is unreactive under the conditions of formation of the final oligomer or during covalent attachment of the oligomer to a compound (or intermediate thereof) of the present invention, or it is protected as necessary. One common end-functional group is hydroxyl or —OH, particularly for oligoethylene oxides.

The water-soluble oligomer (e.g., "POLY" in the structures provided herein) can have any of a number of different geometries. For example, it can be linear, branched, or forked. Most typically, the water-soluble oligomer is linear or is branched, for example, having one branch point. Although much of the discussion herein is focused upon poly(ethylene oxide) as an illustrative oligomer, the discussion and structures presented herein can be readily extended to encompass any of the water-soluble oligomers described above.

The molecular weight of the water-soluble oligomer, excluding the linker portion, in certain embodiments is generally relatively low. For example, the molecular weight of the water-soluble oligomer is typically below about 2200 Daltons, and more typically at around 1500 Daltons or below. In certain other embodiments, the molecular weight of the water-soluble oligomer may be below 800 Daltons.

In certain embodiments, exemplary values of the molecular weight of the water-soluble oligomer include less than or equal to about 500 Daltons, or less than or equal to about 420 Daltons, or less than or equal to about 370 Daltons, or less than or equal to about 370 Daltons, or less than or equal to about 325 Daltons, less than or equal to about 280 Daltons, less than or equal to about 235 Daltons, or less than or equal to about 200 Daltons, less than or equal to about 175 Daltons, or less than or equal to about 150 Daltons, or less than or equal to about 135 Daltons, less than or equal to about 90 Daltons, or less than or equal to about 60 Daltons, or even less than or equal to about 45 Daltons.

In certain embodiments, exemplary values of the molecular weight of the water-soluble oligomer, excluding the linker portion, include: below about 1500 Daltons; below about 1450 Daltons; below about 1400 Daltons; below about 1350 Daltons; below about 1300 Daltons; below about 1250 Daltons; below about 1200 Daltons; below about 1150 Daltons; below about 1100 Daltons; below about 1050 Daltons; below about 1000 Daltons; below about 950 Daltons; below about 900 Daltons; below about 850 Daltons; below about 800 Daltons; below about 750 Daltons; below about 700 Daltons; below about 650 Daltons; below about 600 Daltons; below about 550 Daltons; below about 500 Daltons; below about 450 Daltons; below about 400 Daltons; and below about 350 Daltons; but in each case above about 250 Daltons.

In certain embodiments, the number of monomers in the water-soluble oligomer falls within one or more of the following inclusive ranges: between 1 and 30 (i.e., is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30); between 1 and 25 (i.e., is selected from 1, 2, 3, 4, 5, 6, 7, 8, 9, 10, 11, 12, 13, 14, 15, 16, 17, 18, 19, 20, 21, 22, 23, 24, and 25); between 1 and 20 (i.e., is selected from 1, 2, 3, 4, 5, 6, 7, 8, 9, 10, 11, 12, 13, 14, 15, 16, 17, 18, 19, and 20); between 1 and 15 (is selected from 1, 2, 3, 4, 5, 6, 7, 8, 9, 10, 11, 12, 13, 14, 15); between 1 and 10 (i.e., is selected from 1, 2, 3, 4, 5, 6, 7, 8, 9, and 10); between 10 and 25 (i.e., is selected from 10, 11, 12, 13, 14, 15, 16, 17, 18, 19, 20, 21, 22, 23, 24, and 25); and between 15 and 20 (i.e., is selected from 15, 16, 17, 18, 19, and 20). In certain instances, the number of monomers in series in the oligomer (and the corresponding compound) is one of 1, 2, 3, 4, 5, 6, 7, 8, 9, 10, 11, 12, 13, 14, 15, 16, 17, 18, 19, 20, 21, 22, 23, 24, or 25. Thus, for example, when the water-soluble oligomer includes $CH_3—(OCH_2CH_2)_n—$, "n" is an integer that can be 1, 2, 3, 4, 5, 6, 7, 8, 9, 10, 11, 12, 13, 14, 15, 16, 17, 18, 19, 20, 21, 22, 23, 24, or 25. In certain embodiments, the number of monomers in the water-soluble oligomer falls within one or more of the following inclusive ranges: between 1 and 5 (i.e., is selected from 1, 2, 3, 4, and 5); between 1 and 4 (i.e., can be 1, 2, 3, or 4); between 1 and 3 (i.e., selected from 1, 2, or 3); between 1 and 2 (i.e., can be 1 or 2); between 2 and 5 (i.e., can be selected from 2, 3, 4, and 5); between 2 and 4 (i.e., is selected from 2, 3, and 4); between 2 and 3 (i.e., is either 2 or 3); between 3 and 5 (i.e., is either 3, 4 or 5); between 3 and 4 (i.e., is 3 or 4); and between 4 and 5 (i.e., is 4 or 5). In a specific instance, the number of monomers in series in the oligomer (and the corresponding compound) is selected from 1, 2, 3, 4, or 5. Thus, for example, when the water-soluble oligomer includes $CH_3—(OCH_2CH_2)_n—$, "n" is an integer that can be 1, 2, 3, 4, or 5.

When the water-soluble oligomer is attached to the synthetic intermediate of a compound of Formula I (in contrast to the step-wise addition of one or more monomers to effectively "grow" the oligomer onto the compound of Formula I or synthetic intermediate thereof), the composition containing an activated form of the water-soluble oligomer may be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and in certain embodiments, is 1.001 or less, and in certain embodiments is 1.0005 or less. In certain embodiments, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

In certain embodiment, the water-soluble oligomer is obtained from a composition that is unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble oligomers can be prepared as described in Chen and Baker, *J. Org. Chem.* 6870-6873 (1999), WO 02/098949, and U.S. Patent Application Publication 2005/0136031.

As stated above, the water-soluble oligomer includes at least one functional group prior to reaction with the synthetic intermediate of a compound of Formula I. The functional group typically comprises an electrophilic or nucleophilic group for covalent attachment to the intermediate, depending upon the reactive group contained within the intermediate. Examples of nucleophilic groups that may be present in either the oligomer or the intermediate include hydroxyl, amine, hydrazine (—$NHNH_2$), hydrazide (—C(O)$NHNH_2$), and thiol. Preferred nucleophiles include amine, hydrazine, hydrazide, and thiol, particularly amine. Most intermediates will possess a free hydroxyl, amino, thio, aldehyde, ketone, or carboxyl group for reaction with the functional group on the oligomer.

Examples of electrophilic functional groups that may be present in either the oligomer or the synthetic intermediate of a compound of Formula I include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

It is possible, for example, to react a synthetic intermediate of a compound of Formula I bearing a carboxyl group by coupling it to an amino-terminated oligomeric ethylene glycol, to provide a synthetic intermediate for further modification or a compounds of Formula I wherein X comprises an amide. This can be performed, for example, by combining the carboxyl group-bearing intermediate with the amino-terminated oligomeric ethylene glycol in the presence of a coupling reagent, (such as dicyclohexylcarbodiimide or "DCC") in an anhydrous organic solvent. Similarly, the above reaction may take place between a synthetic intermediate of a compound of Formula I bearing an amino group and a carboxyl-terminated oligomeric ethylene glycol.

Further, it is possible to react a synthetic intermediate of a compound of Formula I bearing a hydroxyl group with an oligomeric ethylene glycol halide to result in a synthetic intermediate for further modification or a compound of Formula I wherein X comprises an ether (—O—). This can be performed, for example, by using sodium hydride to deprotonate the hydroxyl group followed by reaction with a halide-terminated oligomeric ethylene glycol. Similarly, the above reaction may take place between a synthetic intermediate of a compound of Formula I bearing a halo group and an oligomeric ethylene glycol bearing a hydroxyl group.

In another example, it is possible to convert a ketone of a synthetic intermediate of a compound of Formula I bearing a ketone group to a hydroxyl group by first reducing the ketone group to form the corresponding hydroxyl group. Thereafter, the synthetic intermediate may be reacted now bearing a hydroxyl group may be reacted as described herein.

In still another instance, it is possible to react a synthetic intermediate of a compound of Formula I bearing an amine group. In one approach, the amine group-bearing synthetic intermediate and a carbonyl-bearing oligomer are dissolved in a suitable buffer after which a suitable reducing agent (e.g., NaCNBH$_3$) is added. Following reduction, the result is an amine linkage formed between the amine group of the amine group-containing synthetic intermediate and the carbonyl carbon of the aldehyde-bearing oligomer. Similarly, the reaction may take place where the synthetic intermediate bears a carbonyl group and the oligomer bears and amine.

In another approach for preparing a compound of the present invention, where the synthetic intermediate bears an amine group, a carboxylic acid-bearing oligomer and the amine group-bearing intermediate are combined, typically in the presence of a coupling reagent (e.g., DCC). The result is an amide linkage formed between the amine group of the amine group-containing synthetic intermediate and the carbonyl of the carboxylic acid-bearing oligomer. Similarly, the above reaction may take place when the synthetic intermediate bears a carboxyl group and the oligomer bears an amine group.

As non-limiting examples, the synthetic examples below provide exemplary means for preparing compounds of the present invention. One of skill in the art would understand such procedures may be modified depending on the desired target compound or reaction conditions.

In certain embodiments, compounds of Formula I, including those of Formula XVI and XVII, may be prepared according to the following scheme:

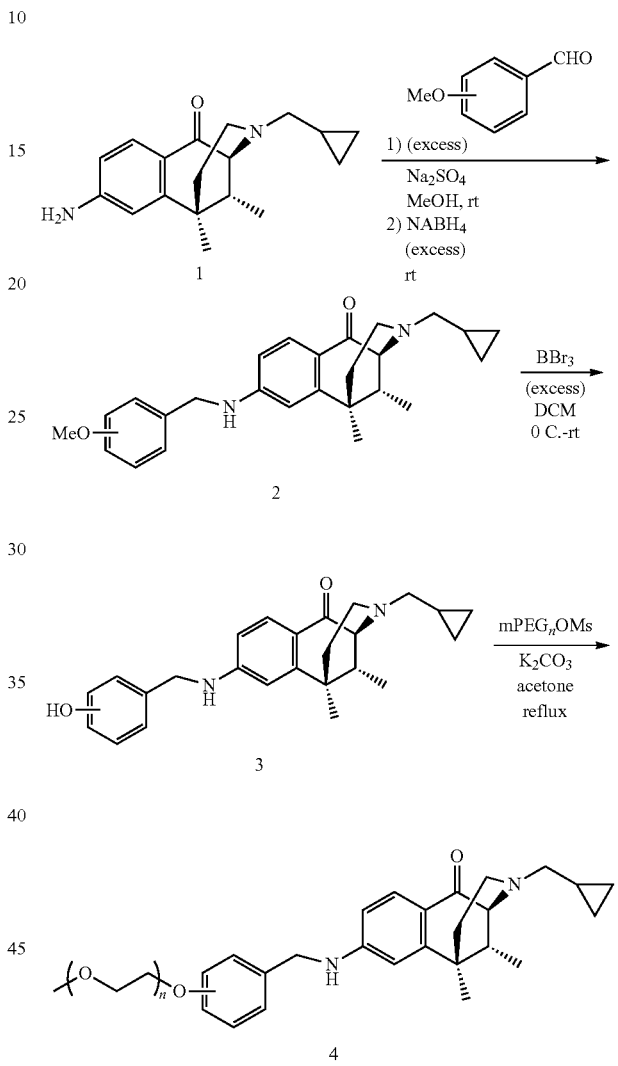

In this scheme, a compound of formula 1 is reacted with an aldehyde or ketone under reductive amination conditions. The resulting compound 2 is further deprotected (submitted to O-demethylation conditions) to form a free hydroxyl containing compound. That compound is further subjected to reaction with a poly(ethylene glycol) coupling conditions for forming a compound of Formula I, including those of Formula XVI and XVII. It is understood that the reagents and conditions listed in this scheme are exemplary and substitutions could be made based on the desired target compound.

In certain embodiments, compounds of Formula I, including those of Formula XV, may be prepared according to the following scheme:

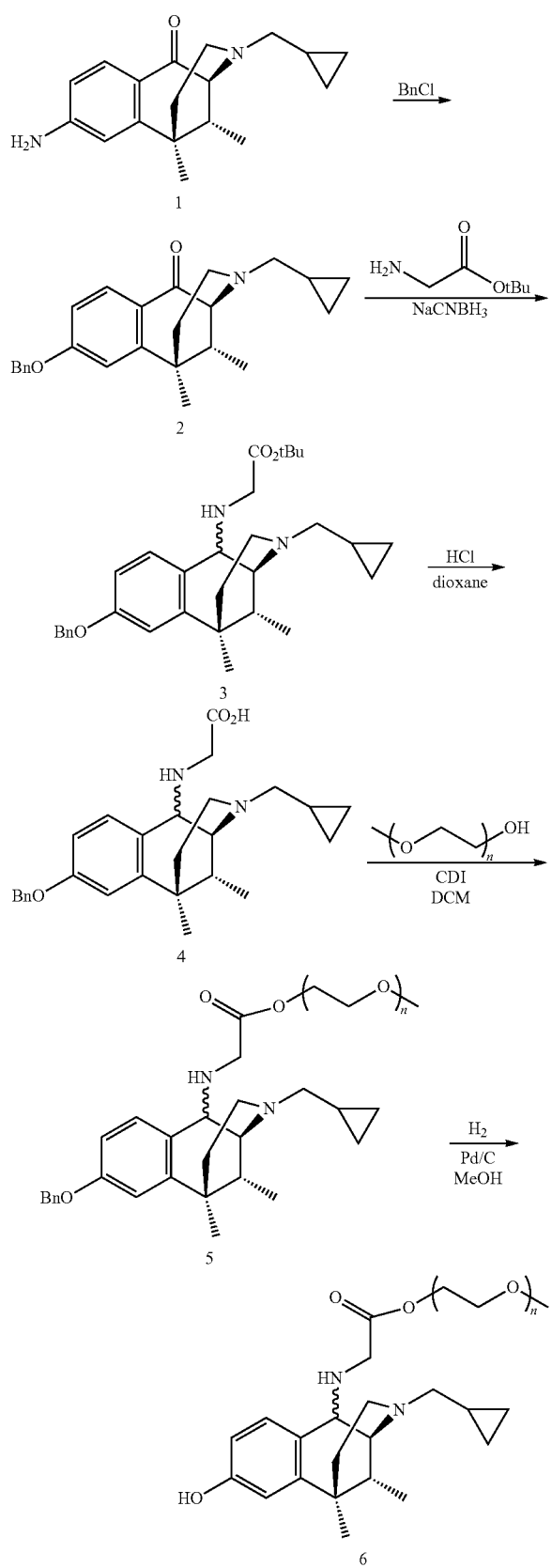

ing compound of formula 2 is coupled to a protected amino acid, under reductive amino acid conditions. The acid portion of the compound of formula 3 is deprotected and reacted with a poly(ethylene glycol) reagent. Finally, the compound of formula 5 is deprotected to provide the target compound of formula 6. One of skill in the art would appreciate that various other amino acids could be substituted, depending on the desired product.

In certain embodiments, compounds of Formula I, including those of Formula X, may be prepared according to the following scheme:

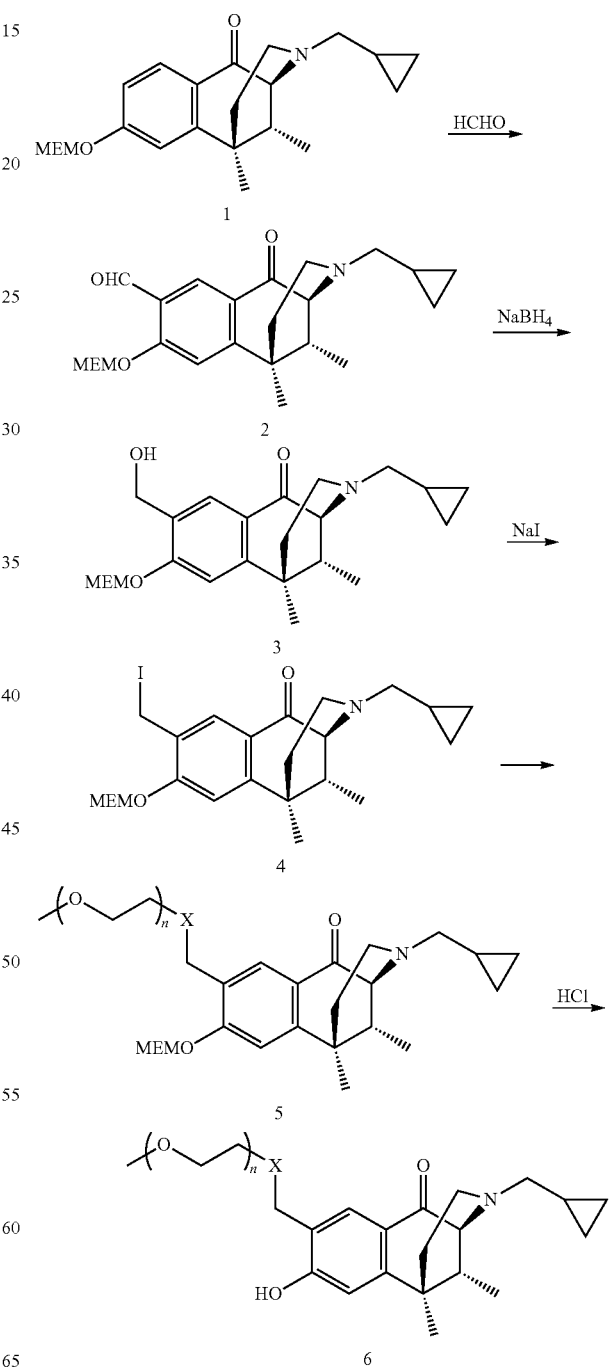

In the above scheme, the compound of formula 1 is protected under standard protection conditions. The result- In the reaction scheme above, the compound of formula 1 is submitted to formylation conditions to prepare compound of formula 2. That compound of formula 2 is reduced to the hydroxylated compound of formula 3. A suitable leaving group may be introduced into the compound to formula 3, for example a halogen, to form a compound of formula 4. That compound of formula 4 may be reacted with a suitable poly(ethylene glycol) reagent (e.g. where X is O or N) to form a compound of formula 5. The target compound of formula 6 is prepared by deprotecting the compound of formula 6.

Certain compounds of the present invention are understood to have activity as agonists of the kappa opioid receptor. The compounds may also have activity as agonists of the mu opioid receptor. Further, the compounds of the present invention may be mixed agonists of both the kappa and mu opioid receptor. The ability of each compound disclosed herein to act as kappa, mu, or mixed opioid agonists may be determined using methods known to those of skill in the art and as disclosed herein. The activity of compounds as kappa, mu, or mixed agonists can be assessed with in-vitro binding and functional assays in kappa opioid receptor and/or mu opioid receptor expressing cell lines/membranes and compared to known kappa/mu agonists.

Approaches for evaluating analgesic activity of a compound of the present invention in vivo include a "writhing test." Briefly, the compound to be tested is administered [by, for example, injection (e.g., subcutaneous injection)] to the mouse. Thereafter, a 0.5% acetic acid solution is administered (i.p.) to a mouse and the numbers of writhing responses are counted for twenty minutes. Antinociception is quantified as reduction in the number of writhes respective to vehicle.

Beyond acting as kappa, mu, and/or mixed opioid agonists, the present compounds are intended to act primarily on opioid receptors in the peripheral nervous system rather than those receptors in the central nervous system. As recited above, each compound of Formula I includes at least one —X-POLY group. It is believed that the POLY portion of the compound of Formula I acts to reduce the rate and/or extent to which the compound of Formula I crosses into the central nervous system. The propensity of a compound of the present invention to cross the blood-brain barrier may be measured by methods known to those of skill in the art and those described herein.

With respect to the blood-brain barrier ("BBB"), this barrier consists of a continuous layer of unique endothelial cells joined by tight junctions. The cerebral capillaries, which comprise more than 95% of the total surface area of the BBB, represent the principal route for the entry of most solutes and drugs into the central nervous system.

As will be understood by one of skill in the art, molecular size, lipophilicity, and P-glycoprotein ("PgP") interaction are among the primary parameters affecting the intrinsic BBB permeability properties of a given molecule. That is to say, these factors, when taken in combination, play a significant role in determining whether a given molecule passes through the BBB. Other factors (e.g., other active transport mechanisms) may also play a role in ultimately determining whether a given molecule will pass through the BBB.

With respect to molecular size, the molecular size plays a significant role in determining whether a given molecule will pass through the BBB. Relatively very large molecules, for example a molecule having a molecular weight of 5,000 Daltons, will not cross the BBB, whereas relatively small molecules are more likely to cross the BBB. Other factors, however, also play a role in BBB crossing. Antipyrine and atenolol are both small molecule drugs; antipyrine readily crosses the BBB, whereas passage of atenolol is very limited, or effectively non-existent. Antipyrine is an industry standard for a high BBB permeation; atenolol is an industry standard for low permeation of the BBB. See, e.g., Summerfield et al., *J Pharmacol Exp Ther* 322:205-213 (2007).

Lipophilicity is also a factor in BBB permeation. Lipophilicity may be expressed as log P (partition coefficient) or in some instances log D (distribution coefficient). The log P (or log D) for a given molecule can be readily assessed by one of skill in the art. The value for log P may be a negative number (more hydrophilic molecules) or a positive number (more hydrophobic molecules). As used herein when referring to log P, "more negative" means moving in the direction, on the log P scale, from positive to negative log P (e.g., a log P of 2.0 is "more negative" than a log P of 4.0, a log P of −2.0 is "more negative" than a log P of −1.0). Molecules having a negative log P (hydrophilic molecules) generally do not permeate the BBB.

Permeability across the BBB is also dependent on the influence of transporters, such as P-glycoprotein, or PgP, an ATP-dependent efflux transporter highly expressed at the BBB. One of skill in the art can readily determine whether a compound is a substrate for PgP using in vitro methods. Compounds which are substrates for PgP in vitro likely will not permeate the BBB in vivo. Conversely, poor substrates for PgP, as assessed in vitro, are generally likely to display in vivo permeability of the BBB, provided the compound meets other criteria as discussed herein and as known to one of skill in the art. See, e.g., Tsuji, *NeuroRx* 2:54-62 (2005) and Rubin and Staddon, *Annu. Rev. Neurosci.* 22:11-28 (1999).

Even in the context of multiple variables (e.g., molecular size, lipophilicity, transporter influences, linkage type), it is possible to analyze a particular compounds ability to cross the BBB using methods known to those of skill in the art.

For any given compound whose degree of BBB crossing ability is not readily known, such BBB crossing ability can be determined using a suitable animal model such as an in situ rat brain perfusion ("RBP") model. Briefly, the RBP technique involves cannulation of the carotid artery followed by perfusion with a compound solution under controlled conditions, followed by a wash out phase to remove compound remaining in the vascular space. More specifically, in the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl et al. (2000) *J. Med. Chem.* 43:3714-3717 and Kelder et al. (1999) *Pharm. Res.* 16:1514-1519.

The compounds of the present invention are expected to have varying degrees of activity against opioid receptors as well as varying degrees to which they cross the BBB. While the compounds of the present invention have activity against the kappa and/or mu opioid receptor, they are believed to also have some degree of exclusion from the central nervous system based on the presence of the X-POLY group in each compound.

Brain PK studies may also be conducted to measure the extent of brain entry in-vivo drug concentrations at enter the CNS at various time post-dose. In brief, rodents are administered with the test article (oral, subcutaneous, or other). At various times post dose terminal blood is collected. Then the rodent is transcardially perfused with cold isotonic saline to remove as much blood from the tissues and brain are extracted. Both plasma and brain are measured for drug content with LC/MS/MS.

The locomotor activity (LMA) model may be conducted to measure changes in activity following test article administration, which may be used to assess the CNS effects of the drug. In brief, at a predetermined time post-dose, rats are placed into observation chambers which are equipped with infrared photocells that can sense motion in the x, y, and z planes. Activity is measured as the number of photobeam breaks in a given plane (horizontal or vertical) or total distance traveled.

In further embodiments, the invention provides for compositions comprising the compounds disclosed herein and a pharmaceutically acceptable excipient or carrier. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the compound or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the compound in the composition will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, in certain embodiments from about 5%-98% by weight, in certain embodiments from about 15-95% by weight of the excipient, and in certain embodiments concentrations less than 30% by weight.

These foregoing pharmaceutical excipients along with other excipients and general teachings regarding pharmaceutical compositions are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. In certain embodiments, preparations are in a form suitable for oral administration such as a tablet, caplet, capsule, gel cap, troche, dispersion, suspension, solution, elixir, syrup, lozenge, transdermal patch, spray, suppository, and powder. Oral dosage forms are preferred for those compounds that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the compounds described herein. In addition to the compound, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the compound-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compound can also be administered through the skin using conventional transdermal patch or other transdermal delivery system, wherein the compound is contained within a laminated structure that serves as a drug delivery device to be affixed to the skin. In such a structure, the compound is contained in a layer, or "reservoir," underlying an upper backing layer. The laminated structure can contain a single reservoir, or it can contain multiple reservoirs.

The compound can also be formulated into a suppository for rectal administration. With respect to suppositories, the compound is mixed with a suppository base material which is (e.g., an excipient that remains solid at room temperature but softens, melts or dissolves at body temperature) such as coca butter (*theobroma* oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a compound provided herein to a patient suffering from a condition that is responsive to treatment with the compound such as pain. The method comprises administering, generally orally, a therapeutically effective amount of the compound (in certain embodiments provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The method of administering may be used to treat any condition that can be remedied or prevented by administration of a kappa opioid agonist, a mu opioid agonist, or a mixed opioid agonist. Most commonly, the compounds provided herein are administered for the management of pain, including visceral pain, chronic pelvic pain and interstitial cystitis. Kappa agonists have also been used to treat irritable bowel syndrome. Those of ordinary skill in the art appreciate which conditions a specific compound can effectively treat. The actual dose to be administered will vary depend upon the age, weight, and general condition of the subject as well as the severity of the condition being treated, the judgment of the health care professional, and compound being administered. Therapeutically effective amounts are known to those skilled in the art and/or are described in the pertinent reference texts and literature. Generally, a therapeutically effective amount will range from about 0.001 mg to 1000 mg, in certain embodiments in doses from 0.01 mg/day to 750 mg/day, and in certain embodiments in doses from 0.10 mg/day to 500 mg/day.

The unit dosage of any given compound (in certain embodiments, provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are hereby incorporated by reference in their entireties.

It is to be understood that while the invention has been described in conjunction with certain and specific embodiments, the foregoing description as well as the examples that follow are intended to illustrate and not limit the scope of the invention. Other aspects, advantages and modifications within the scope of the invention will be apparent to those skilled in the art to which the invention pertains.

EXAMPLES

All chemical reagents referred to in the appended examples are commercially available unless otherwise indicated. The preparation of PEG-mers is described in, for example, U.S. Patent Application Publication No. 2005/0136031.

Example 1

Preparation of (2S,6R,11R)-3-(Cyclopropylmethyl)-8-({2-[2-(2-methoxy)ethoxy]ethyl}amino-6.11-dimethyl-3,4,5,6-tetrahydro-2,6-methano-3-benzazocin-1(2H)-one (1)

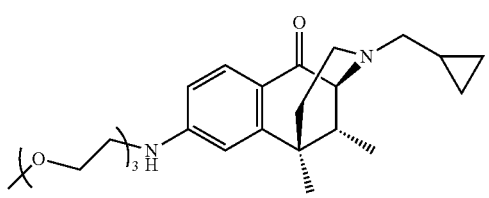

(2S,6R,11R)-3-(Cyclopropylmethyl)-8-({2-[2-(2-methoxy)ethoxy]ethyl}amino-6.11-dimethyl-3,4,5,6-tetrahydro-2,6-methano-3-benzazocin-1(2H)-one (1) was prepared according to the following steps.

Step 1: Preparation of (2S,6R,11R)-3-(Cyclopropylmethyl)-6,11-dimethyl-1-oxo-1,2,3,4,5,6-hexahydro-2,6-methano-3-benzazocin-8-yl trifluoromethanesulfonate

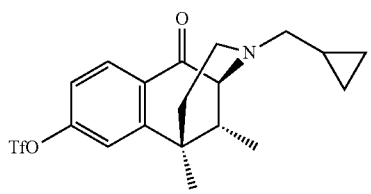 [SMILES: C[C@H]1[C@H]2C(=O)c3ccc(OS(=O)(=O)C(F)(F)F)cc3[C@@]1(C)CCN2CC1CC1]

Ketazocine (0.50 g, 1.75 mmol) was dissolved in anhydrous dichloromethane (40 mL) and triethylamine (1.24 mL, 8.76 mmol). The light-yellow solution was cooled to 0° C. and added N-phenyl-bis(trifluoromethanesulfonimide) (0.94 g, 2.63 mmol). The yellow reaction mixture was allowed to equilibrate to room temperature. After approximately 17 hours the reaction mixture was diluted with dichloromethane (50 mL). The mixture was transferred to a separatory funnel and washed with water (40 mL), 1N sodium hydroxide (40 mL) and saturated sodium chloride (40 mL). The organic portion was dried over anhydrous sodium sulfate and concentrated in vacuo. The residue was purified on a column of silica gel using dichloromethane/methanol (9:1) as eluent to give (2S,6R,11R)-3-(cyclopropylmethyl)-6,11-dimethyl-1-oxo-1,2,3,4,5,6-hexahydro-2,6-methano-3-benzazocin-8-yl trifluoromethanesulfonate (0.64 g, 88%) as a yellow oil. $^1$H NMR (500 MHz, CDCl$_3$): δ 8.09 (m, 1H), 7.22 (m, 2H), 3.32 (m, 1H), 2.93 (m, 1H), 2.67 (m, 1H), 2.23 (m, 1H), 2.09 (m, 1H), 2.01 (m, 2H), 1.95 (m, 1H), 1.53 (m, 1H), 1.50 (s, 3H), 0.87 (m, 2H), 0.50 (m, 2H), 0.07 (m, 1H), 0.05 (m, 1H); MS (EI) for C$_{19}$H$_{22}$F$_3$NO$_4$S: 418 (MH$^+$).

Step 2: Preparation of (2S,6R,11R)-3-(Cyclopropylmethyl)-8-({2-[2-(2-methoxy)ethoxy]ethyl}amino-6.11-dimethyl-3,4,5,6-tetrahydro-2,6-methano-3-benzazocin-1(2H)-one (1)

(2S,6R,11R)-3-(Cyclopropylmethyl)-6,11-dimethyl-1-oxo-1,2,3,4,5,6-hexahydro-2,6-methano-3-benzazocin-8-yl trifluoromethanesulfonate (33 mg, 0.079 mmol) from step 1, 2-[2-(2-methoxyethoxy)ethoxy]ethanamine (40 mg, 0.24 mmol) and 1-methyl-2-pyrrolidinone (3 mL) were added to a 2-5 mL microwave vial, and then heated under microwave irradiation for 2 hours at 200° C. The reaction mixture was cooled to room temperature, poured into 12 mL water and extracted with methyl tert-butyl ether (3×5 mL). The combined organic portions were washed with water (20 mL) and saturated sodium chloride (20 mL) and then dried over anhydrous sodium sulfate. The residue was purified by silica gel chromatography using methanol/dichloromethane (1:9) as eluent to give 0.012 g (35%) of (2S,6R,11R)-3-(cyclopropylmethyl)-8-({2-[2-(2-methoxy)ethoxy]ethyl}amino-6.11-dimethyl-3,4,5,6-tetrahydro-2,6-methano-3-benzazocin-1(2H)-one (1) as a yellow oil. $^1$H NMR (500 MHz, CDCl$_3$): 7.85 (s, 1H), 6.50 (m, 1H), 6.39 (s, 1H), 4.84 (m, 1H), 3.74 (m, 2H), 3.72 (m, 6H), 3.66 (m, 2H), 3.37 (m, 5H), 2.91 (m, 1H), 2.76 (m, 1H), 2.12 (m, 2H), 2.01 (m, 3H), 1.52 (m, 1H), 1.31 (m, 3H), 0.89 (m, 4H), 0.47 (m, 2H), 0.25 (m, 1H), 0.05 (m, 1H); MS (EI) for C$_{25}$H$_{38}$N$_2$O$_4$: 431 (MH$^+$).

Example 2

Preparation of (2S,6R,11R)-3-(Cyclopropylmethyl)-6,11-dimethyl-8-(2,5,8,11,14-pentaoxahexadecan-16-ylamino)-3,4,5,6-tetrahydro-2,6-methano-3-benzazocin-1(2H)-one (2)

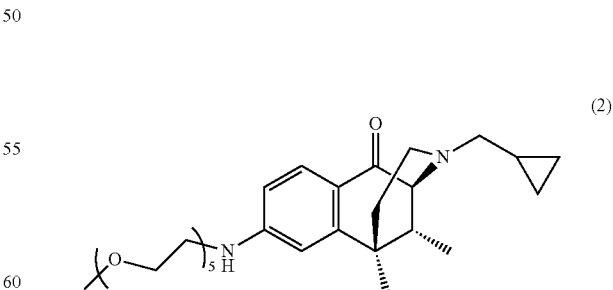

(2S,6R,11R)-3-(Cyclopropylmethyl)-6,11-dimethyl-1-oxo-1,2,3,4,5,6-hexahydro-2,6-methano-3-benzazocin-8-yl trifluoromethanesulfonate (0.10 g, 0.24 mmol) (from Example 1, step 1), 2,5,8,11,14-pentaoxahexadecan-16-amine (0.18 g, 0.73 mmol) and 1-methyl-2-pyrrolidinone (3 mL) were added to a 2-5 mL microwave vial, and then heated under microwave irradiation for 2 hours at 200° C. The reaction mixture was cooled to room temperature, poured into 12 mL water and extracted with methyl tert-butyl ether (3×5 mL). The combined organic portions were washed with water (20 mL) and saturated sodium chloride (20 mL) and then dried over anhydrous sodium sulfate. The residue was purified by silica gel chromatography using methanol/dichloromethane (1:9) as eluent to give 0.012 g (35%) of (2S,6R,11R)-3-(cyclopropylmethyl)-6,11-dimethyl-8-(2,5,8,11,14-pentaoxahexadecan-16-ylamino)-3,4,5,6-tetrahydro-2,6-methano-3-benzazocin-1(2H)-one as a yellow oil. $^1$H NMR (500 MHz, CDCl3): 7.85 (m, 1H), 6.48 (m, 1H), 6.39 (m, 1H), 4.92 (m, 1H), 3.72 (m, 2H), 3.63 (m, 15H), 3.55 (m, 2H), 3.37 (m, 5H), 2.90 (m, 1H), 2.74 (m, 1H), 2.12-1.95 (m, 4H), 1.51 (m, 1H), 1.38 (s, 3H), 0.89 (m, 4H), 0.47 (m, 2H), 0.25 (m, 1H), 0.05 (m, 1H); MS (EI) for $C_{29}H_{46}N_2O_6$: 519 (MH$^+$).

Example 3

Preparation of (2S,6R,11R)-3-(Cyclopropylmethyl)-8-(2,5,8,11,14,17,20-heptaoxadocosan-22-ylamino)-6,11-dimethyl-3,4,5,6-tetrahydro-2,6-methano-3-benzazocin-1(2H)-one (3)

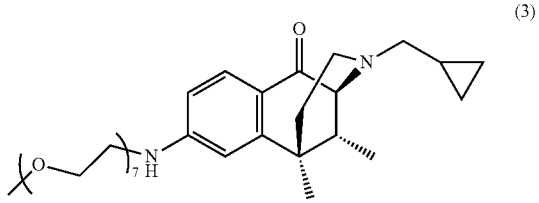

(3)

(2S,6R,11R)-3-(Cyclopropylmethyl)-6,11-dimethyl-1-oxo-1,2,3,4,5,6-hexahydro-2,6-methano-3-benzazocin-8-yl trifluoromethanesulfonate (0.10 g, 0.24 mmol) (from Example 1, step 1), 2,5,8,11,14,17,20-heptaoxadocosan-22-amine (0.18 g, 0.73 mmol) and 1-methyl-2-pyrrolidinone (3 mL) were added to a 2-5 mL microwave vial, and then heated under microwave irradiation for 2 hours at 200° C. The reaction mixture was cooled to room temperature, poured into 12 mL water and extracted with methyl tert-butyl ether (3×5 mL). The combined organic portions were washed with water (20 mL) and saturated sodium chloride (20 mL) and then dried over anhydrous sodium sulfate. The residue was purified by silica gel chromatography using methanol/dichloromethane (1:9) as eluent to give 0.08 g (55%) of (2S,6R,11R)-3-(cyclopropylmethyl)-8-(2,5,8,11,14,17,20-heptaoxadocosan-22-ylamino)-6,11-dimethyl-3,4,5,6-tetrahydro-2,6-methano-3-benzazocin-1(2H)-one as a yellow oil. $^1$H NMR (500 MHz, CDCl3): 7.85 (m, 1H), 6.49 (m, 1H), 6.38 (m, 1H), 3.73 (m, 2H), 3.72 (m, 24H), 3.71 (m, 2H), 3.54 (m, 5H), 2.97 (m, 1H), 2.75 (m, 1H), 2.15 (m, 1H), 2.01 (m, 3H), 1.49 (m, 1H), 1.38 (s, 3H), 0.89 (m, 3H), 0.48 (m, 2H), 0.46 (m, 2H), 0.25 (m, 1H); MS (EI) for $C_{33}H_{54}N_2O_8$: 607 (MH$^+$).

Example 4

Preparation of (2S,6R,11R)-3-(Cyclopropylmethyl)-8-{2-[2-(2-methoxyethoxy)ethoxy]ethoxy}-6,11-dimethyl-3,4,5,6-tetrahydro-2,6-methano-3-benzazocin-1(2H)-one (4)

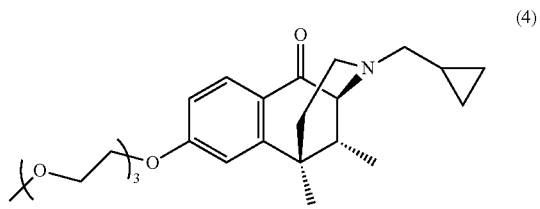

(4)

Into a three-necked flask was placed ketazocine (0.47 g, 1.66 mmol), potassium carbonate (0.57 g, 4.16 mmol), 2-[2-(2-methoxyethoxy)ethoxy]ethyl methanesulfonate (0.44 g, 1.83 mmol) in acetone (35 mL). The yellow reaction mixture was heated to reflux and stirred under nitrogen. After approximately 17 hours reflux the yellow mixture was cooled to room temperature. The solvent was removed under reduced pressure and the residue partitioned between water and dichloromethane (25 mL each). The aqueous layer was extracted with dichloromethane (3×12 mL). The combined organic portions were washed with water and saturated sodium chloride (2×25 mL each). The organic portion was filtered and concentrated and the residue was purified on a column of silica gel using dichloromethane/methanol (9:1) as eluent to give (2S,6R,11R)-3-(cyclopropylmethyl)-8-{2-[2-(2-methoxyethoxy)ethoxy]ethoxy}-6,11-dimethyl-3,4,5,6-tetrahydro-2,6-methano-3-benzazocin-1(2H)-one (64 mg, 37% yield), as a light-yellow oil. $^1$H NMR (500 MHz, CDCl$_3$): δ 7.80 (m, 1H), 6.94 (m, 1H), 6.86 (m, 1H), 4.19 (m, 2H), 3.75 (m, 2H), 3.75 (m, 2H), 3.58-3.42 (m, 8H), 3.33 (s, 3H), 3.13 (m, 1H), 2.77 (m, 1H), 2.47 (m, 2H), 2.05-1.85 (m, 4H), 1.45 (m, 1H), 1.38 (s, 3H), 0.85 (m, 1H0, 0.77 (m, 3H), 0.42 (m, 2H), 0.19 (m, 1H); MS (EI) for $C_{25}H_{37}NO_5$: 432 (MH$^+$).

The compound was converted into the hydrochloride salt by dissolving the oil in acetonitrile and adding 1N hydrochloric acid. The solution was lyopholized to give the hydrochloride salt as a white powder.

Example 5

Preparation of (2S,6R,11R)-3-(Cyclopropylmethyl)-6,11-dimethyl-8-(2,5,8,11,14-pentaoxahexadecan-16-ylamino)-3,4,5,6-tetrahydro-2,6-methano-3-benzazocin-1(2H)-one (5)

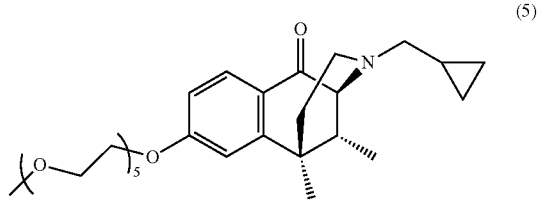

(5)

Into a three-necked flask was placed ketazocine (0.10 g, 0.35 mmol), potassium carbonate (0.12 g, 0.87 mmol), 2,5,8,11,14-pentaoxahexadecan-16-yl methanesulfonate (0.12 g, 0.38 mmol) in acetone (12 mL). The yellow reaction mixture was heated to reflux and stirred under nitrogen. After approximately 17 hours reflux the yellow mixture was cooled to room temperature. The solvent was removed under reduced pressure and the residue partitioned between water and dichloromethane (10 mL each). The aqueous layer was extracted with dichloromethane (3×8 mL). The combined organic portions were washed with water and saturated sodium chloride (2×15 mL each). The organic portion was filtered and concentrated and the residue was purified on a column of silica gel using dichloromethane/methanol (9:1) as eluent to give (2S,6R,11R)-3-(cyclopropylmethyl)-6,11-dimethyl-8-(2,5,8,11,14-pentaoxahexadecan-16-ylamino)-3,4,5,6-tetrahydro-2,6-methano-3-benzazocin-1(2H)-one (0.11 g, 63% yield), as a light-yellow oil. $^1$H NMR (500 MHz, CDCl$_3$): δ 7.95 (m, 1H), 6.82 (m, 2H), 4.19 (m, 2H), 3.81 (m, 2H), 3.75-3.56 (m, 16H), 3.34 (s, 3H), 3.25 (m, 1H), 2.92 (m, 1H), 2.71 (m, 1H), 2.18 (m, 1H), 1.94 (m, 3H), 1.50 (m, 1H), 1.40 (s, 3H), 0.88 (m, 4H), 0.49 (m, 2H), 0.30 (m, 1H), 0.10 (m, 1H); MS (EI) for C$_{29}$H$_{45}$NO$_7$: 520 (MH$^+$).

Example 6

Preparation of (2S,6R,11R)-3-(Cyclopropylmethyl)-8-(2,5,8,11,14,17,20-heptaoxadocosan-22-yloxy)-6,11-dimethyl-3,4,5,6-tetrahydro-2,6-methano-3-benzazocin-1(2H)-one (6)

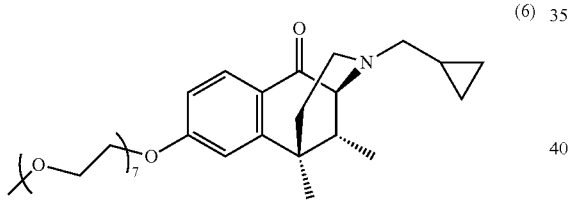

(6)

Into a three-necked flask was placed ketazocine (0.10 g, 0.35 mmol), potassium carbonate (0.12 g, 0.87 mmol), 2,5,8,11,14,17,20-heptaoxadocosan-22-yl methanesulfonate (0.15 g, 0.36 mmol) in acetone (10 mL). The yellow reaction mixture was heated to reflux and stirred under nitrogen. After approximately 17 hours reflux the yellow mixture was cooled to room temperature. The solvent was removed under reduced pressure and the residue partitioned between water and dichloromethane (10 mL each). The aqueous layer was extracted with dichloromethane (3×8 mL). The combined organic portions were washed with water and saturated sodium chloride (2×15 mL each). The organic portion was filtered and concentrated and the residue was purified on a column of silica gel using dichloromethane/methanol (9:1) as eluent to give (2S,6R,11R)-3-(cyclopropylmethyl)-8-(2,5,8,11,14,17,20-heptaoxadocosan-22-yloxy)-6,11-dimethyl-3,4,5,6-tetrahydro-2,6-methano-3-benzazocin-1(2H)-one (0.12 g, 57% yield), as a light-yellow oil. $^1$H NMR (500 MHz, CDCl$_3$): δ 7.95 (m, 1H), 6.84-6.81 (m, 2H), 4.18 (m, 2H), 3.87 (m, 2H), 3.73-3.52 (m, 24H), 3.38 (s, 3H), 3.24 (m, 1H), 2.92 (m, 1H), 2.71 (m, 1H), 2.15 (m, 1H), 1.98 (m, 3H), 1.52 (m, 1H), 1.41 (s, 3H), 0.86 (m, 4H), 0.47 (m, 2H), 0.26 (m, 1H), 0.06 (m, 1H); MS (EI) for C$_{33}$H$_{53}$NO$_9$: 608 (MH$^+$).

Example 7

Preparation of (2S,6R,11R)-8-((2-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (7)

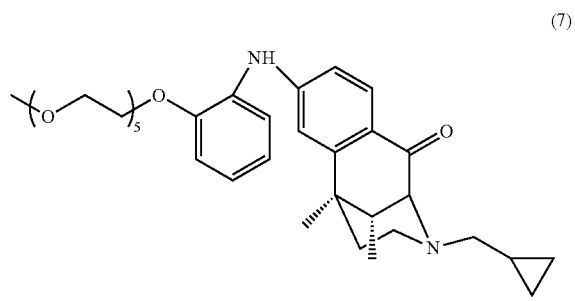

(7)

(2S,6R,11R)-8-((2-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (7) was prepared according to the following steps.

Step 1: Preparation of tert-butyl (2-hydroxyphenyl)carbamate

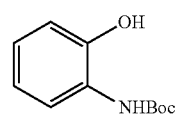

2-Amino phenol (6 g, 55 mmol) was dissolved in 60 mL of THF. (Boc)$_2$O (12 g, 55 mmol) was added to the above mixture and stirred for 16 h. The mixture was concentrated under vacuum to get a gummy mass. Gummy mass was precipitated using 20% MTBE/Hexane. Precipitated solid was filtered and washed with hexane to afford tert-butyl (2-hydroxyphenyl)carbamate (11.2 g, 97% yield)

Step 2: Preparation of tert-butyl (2-(2,5,8,11,14-pentaoxahexadecan-yloxy)phenyl)carbamate

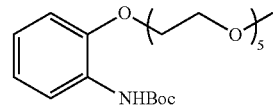

tert-Butyl (2-hydroxyphenyl)carbamate (3 g, 14.34 mmol), mPEG$_5$-OMs (5.21 g, 15.77 mmol) and K$_2$CO$_3$ (5.94 g. 43.0 mmol) were dissolved in 20 mL of DMF. The mixture was heated to 80° C. and stirred at that temperature for 18 h. Reaction was cooled to 25° C. and concentrated under vacuum to get a gummy mass. The gummy residue was dissolved in 30 mL of water (10 vol) and compound was extracted in EtOAc. Organic layer was washed with 1M aq NaOH and brine sequentially, then dried over anhydrous sodium sulfate & concentrated under vacuum to afford tert-butyl (2-(2,5,8,11,14-pentaoxahexadecan-yloxy)phenyl)carbamate (22) (4 g, 63% yield) as a viscous liquid.

Step 3: Preparation of 2-(2,5,8,11,14-pentaoxahexadecan-16-yloxy)aniline

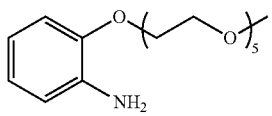

tert-Butyl (2-(2,5,8,11,14-pentaoxahexadecan-yloxy)phenyl)carbamate (3.2 g, 7.21 mmol) was dissolved in 25 mL of 4M HCl in IPA. The mixture was stirred for 1 h and concentrated under vacuum. The residue was dissolved in 50 mL of water and pH of the aqueous solution was adjusted to 9.0 (using 1M aq. NaOH). Compound was extracted into ethyl acetate, dried over anhydrous sodium sulfate, concentrated under vacuum to obtain (2,5,8,11,14-pentaoxahexadecan-16-yloxy)aniline as pale yellow gum (2 g, 86% yield).

Step 4: Preparation of (2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate

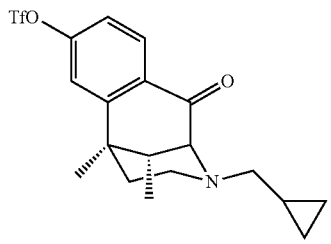

(2S,6R,11R)-3-(cyclopropylmethyl)-8-hydroxy-6,11-dimethyl-3,4,5,6-tetrahydro-2,6-methanobenzo[d]azocin-1(2H)-one (500 mg, 1.75 mmol) and triethyl amine (1.23 mL, 8.76 mmol) were dissolved in 10 mL of dichloromethane. PhNTf$_2$ (925 mg, 18.75 mmol) was added to the above mixture and the reaction, stirred for 16 h. upon completion the reaction was concentrated, Crude thus obtained, was purified (by column chromatography) to get (2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (709 mg, 97% yield).

Step 5: Preparation of (2S,6R,11R)-8-((2-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (7)

(7)

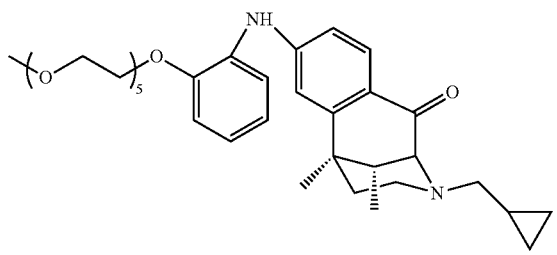

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (200 mg, 0.48 mmol) and (2,5,8,11,14-pentaoxahexadecan-16-yloxy)aniline (197 mg, 0.575 mmol) were dissolved in toluene. BINAP (89 mg, 0.144 mmol), Pd$_2$(dba)$_3$ (88 mg, 0.096 mmol) & Cs$_2$CO$_3$ (219 mg, 0.671 mmol) were added to the above mixture and stirred under heating at 110° C. for 2 h. The mixture was cooled to room temperature and concentrated under vacuum. Crude was purified by column chromatography to get (2S,6R,11R)-8-((2-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (7) (163 mg, 56% yield). $^1$H NMR (500 MHz, CDCl$_3$): δ 7.9 (d, 1H), 7.4-7.42 (m, 1H), 6.90-7.0 (m, 5H), 6.75 (m, 1H), 4.19 (t, 2H), 3.86 (t, 2H), 3.67-3.71 (m, 2H), 3.60-3.65 (m, 12H), 3.51-3.53 (m, 2H), 3.36 (s, 3H), 3.23 (m, 1H), 2.91-2.94 (m, 1H), 2.72-2.76 (m, 1H), 2.12-2.14 (m, 1H), 1.97-2.08 (m, 3H), 1.39 (s, 3H), 1.25 (m, 1H), 0.88-0.91 (m, 4H), 0.46-0.48 (m, 2H), 0.25-0.27 (m, 1H), 0.05-0.08 (m, 1H); MS (ESI) for C$_{35}$H$_{50}$N$_2$O$_7$: 611.3289 (MH$^+$). The free base was dissolved in 4M hydrochloride in 2-propanol. The mixture was concentrated to afford product as hydrochloride salt.

Example 8

Preparation of (2S,6R,11R)-8-((3-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (8)

(8)

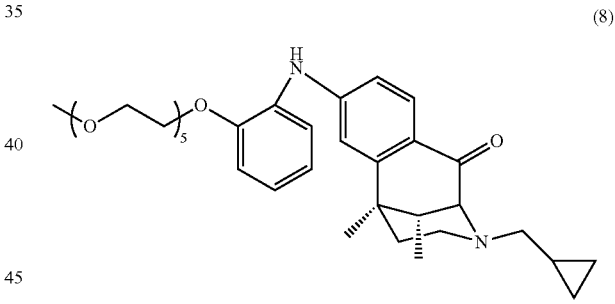

(2S,6R,11R)-8-((3-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (24) was prepared according to the following steps.

Step 1: Preparation of 3-(2,5,8,11,14-pentaoxahexadecan-16-yloxy)aniline

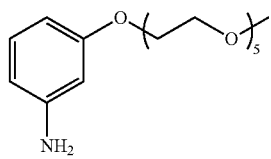

was prepared using procedures similar to Example 7, steps 1-3, wherein 3-amino phenol was used in place of 2-amino phenol in step 1. The product, 3-(2,5,8,11,14-pentaoxahexadecan-16-yloxy)aniline was prepared as a yellow gum (2.5 g, 90% yield)

Step 2: Preparation of (2S,6R,11R)-8-((3-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (8)

(8)

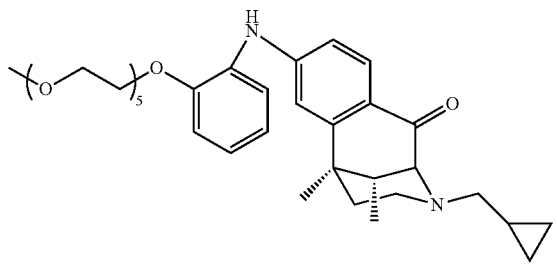

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (prepared in a manner similar to Example 7, step 4) (200 mg, 0.48 mmol) and 3-(2,5,8,11,14-pentaoxahexadecan-16-yloxy)aniline) (197 mg, 0.575 mmol) were dissolved in toluene. BINAP (89 mg, 0.144 mmol), Pd$_2$(dba)$_3$ (88 mg, 0.096 mmol) & Cs$_2$CO$_3$ (219 mg, 0.671 mmol) were added to the above mixture. The reaction mixture was heated to 110° C. & stirred for 2 h. The mixture was cooled to room temperature and concentrated under vacuum. Crude was purified by column chromatography to yield (2S,6R,11R)-8-((3-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (8) (200 mg, 68.3% yield). $^1$H NMR (500 MHz, CDCl$_3$): δ 7.88 (d, 1H), 7.2-7.24 (m, 1H), 6.92-6.94 (m, 1H), 6.83 (d, 1H), 6.74-6.78 (m, 2H), 6.62-6.64 (m, 1H), 6.19 (s, 1H), 4.12 (t, 2H), 3.85 (t, 2H), 3.63-3.73 (m, 14H), 3.53-3.55 (m, 2H), 3.36 (s, 3H), 3.23 (m, 1H), 2.91-2.94 (m, 1H), 2.72-2.76 (m, 1H), 2.11-2.13 (m, 1H), 1.97-2.08 (m, 3H), 1.38 (s, 3H), 1.25 (m, 1H), 0.89-0.91 (m, 4H), 0.46-0.49 (m, 2H), 0.25-0.27 (m, 1H), 0.05-0.08 (m, 1H); MS (ESI) for C$_{35}$H$_{50}$N$_2$O$_7$: 611.3289 (MH$^+$). The free base was dissolved in 4M hydrochloride in 2-propanol. The mixture was concentrated to afford product as hydrochloride salt.

Example 9

Preparation of (2S,6R,11R)-8-((4-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (9)

(9)

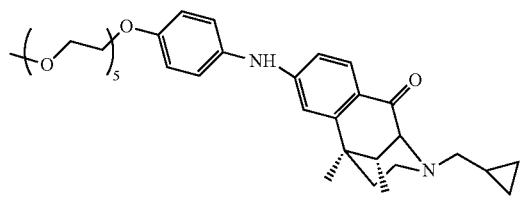

(2S,6R,11R)-8-((4-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one hydrochloride (28) was prepared according to the following steps.

Step 1: 4-(2,5,8,11,14-pentaoxahexadecan-16-yloxy)aniline

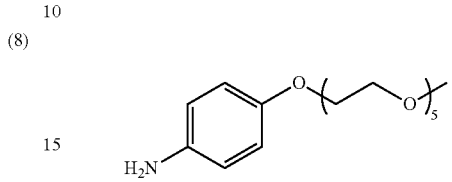

was prepared using procedures similar to Example 7, steps 1-3, wherein 4-amino phenol was used in place of 2-amino phenol in step 1. The product, 4-(2,5,8,11,14-pentaoxahexadecan-16-yloxy)aniline was isolated as a yellow gum (2.35 g, 96% yield)

Step 2: Preparation of (2S,6R,11R)-8-((4-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (9)

(9)

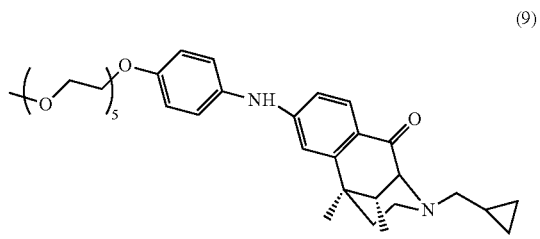

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (prepared in a manner similar to Example 7, step 4) (150 mg, 0.36 mmol) and 4-(2,5,8,11,14-pentaoxahexadecan-16-yloxy)aniline (148 mg, 0.431 mmol) were dissolved in toluene. BINAP (67 mg, 0.108 mmol), Pd$_2$(dba)$_3$ (66 mg, 0.072 mmol) & Cs$_2$CO$_3$ (328 mg, 1.00 mmol) were added to the above mixture and heated (110° C.) for 2 h. The mixture was cooled to room temperature and concentrated under vacuum. Crude was purified by column chromatography to afford (2S,6R,11R)-8-((4-(2,5,8,11,14-pentaoxahexadecan-16-yloxy)phenyl)amino)-3-(cyclopropylmethyl)-6,11-dimethyl-3,4,5,6-tetrahydro-2,6-methanobenzo[d]azocin-1(2H)-one (9) (180 mg, 61.5% yield). $^1$H NMR (500 MHz, CDCl$_3$): δ 7.85 (d, 1H), 7.11-7.13 (m, 2H), 6.91-6.93 (m, 2H), 6.71-6.73 (m, 1H), 6.65 (m, 1H), 5.94 (bs, 1H), 4.14 (t, 2H), 3.87 (t, 2H), 3.63-3.75 (m, 14H), 3.53-3.55 (m, 2H), 3.37 (s, 3H), 3.22 (m, 1H), 2.91-2.94 (m, 1H), 2.72-2.76 (m, 1H), 1.97-2.13 (m, 4H), 1.34 (s, 3H), 1.25 (m, 1H), 0.88-0.90 (m, 4H), 0.46-0.48 (m, 2H), 0.26 (m, 1H), 0.04-0.07 (m, 1H); MS (ESI) for C$_{35}$H$_{50}$N$_2$O$_7$: 611.3289 (MH$^+$). The free base was dissolved in 4M hydrochloride in 2-propanol. The mixture was concentrated to afford product as hydrochloride salt.

Example 10

Preparation of (2S,6R,11R)-8-((4-(2,5,8,11,14-pentaoxahexadecan-16-ylamino)phenyl)amino)-3 (cyclopropylmethyl)-6,11-dimethyl-3,4,5,6-tetrahydro-2,6-methanobenzo[d]azocin-1(2H)-one (10)

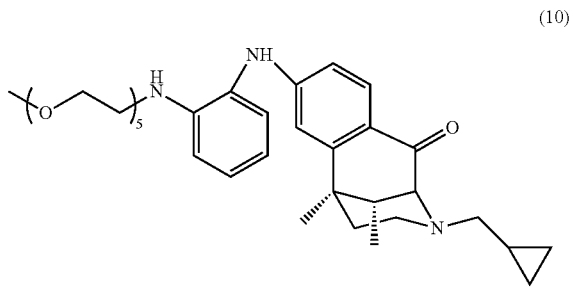

(2S,6R,11R)-8-((4-(2,5,8,11,14-pentaoxahexadecan-16-ylamino)phenyl)amino)-3 (cyclopropylmethyl)-6,11-dimethyl-3,4,5,6-tetrahydro-2,6-methanobenzo[d]azocin-1(2H)-one (10) was prepared according to the following steps.

Step 1: Preparation of tert-butyl (2-aminophenyl)carbamate

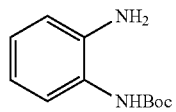

Benzene-1,2-diamine (10 g. 92.47 mmol) was dissolved in 200 mL of dioxane/water (2:1 ratio) and stirred for 10 min. Boc anhydride (21.2 mL, 92.47 mmol) was added to the above mixture and stirred for 5 h. Dioxane was distilled off and mixture was cooled to room temperature. Compound was extracted into MTBE, dried over anhydrous sodium sulfate, and conc. under vacuum to get tert-butyl (2-aminophenyl)carbamate (7) (12.1 g, 63% yield)

Step 2: Preparation of tert-butyl (2-(2,5,8,11,14-pentaoxahexadecan-16-ylamino)phenyl)carbamate

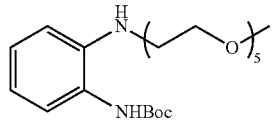

tert-Butyl (2-aminophenyl)carbamate (3 g, 14.41 mmol), sodium bicarbonate (1.45 g, 17.296 mmol) and sodium lauryl sulfate (70 mg, 0.245 mmol) were mixed in 70 mL of water. The mixture was heated to 80° C. and to it was charged mPEG$_5$-OMs (5.71 g, 17.296 mmol). The mixture was stirred under heating for 16 h and then cooled to room temperature. The cooled reaction mixture was extracted with ethyl acetate. The ethyl acetate layer was dried over anhydrous sodium sulfate & conc. under vacuum. Crude was purified by column chromatography to yield tert-butyl (2-(2,5,8,11,14-pentaoxahexadecan-16 ylamino)phenyl) carbamate (2 g, 31% yield).

Step 3: Preparation of N1-(2,5,8,11,14-pentaoxahexadecan-16-yl)benzene-1,2-diamine

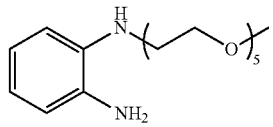

tert-Butyl (2-(2,5,8,11,14-pentaoxahexadecan-16 ylamino)phenyl) carbamate (2 g, 4.52 mmol) was dissolved in 25 mL of 4M HCl in IPA. The mixture was stirred for 1 h and concentrated under vacuum. The residue was dissolved in 50 mL of water and pH was adjusted to 9.0 using 1M aq. NaOH. The Compound was extracted into ethyl acetate, the organic layer was dried over anhydrous sodium sulfate, concentrated under vacuum to get N1-(2,5,8,11,14-pentaoxahexadecan-16-yl)benzene-1,2-diamine as dark brown gum (1.22 g, 79% yield).

Step 4: (2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate

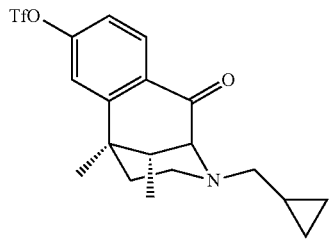 [SMILES: C[C@H]1C2C(=O)c3ccc(OS(=O)(=O)C(F)(F)F)cc3[C@]1(C)CCN2CC1CC1]

was prepared in a manner similar to Example 7, step 4.

Step 5: Preparation of (2S,6R,11R)-8-((4-(2,5,8,11,14-pentaoxahexadecan-16-ylamino)phenyl)amino)-3-(cyclopropylmethyl)-6,11-dimethyl-3,4,5,6-tetrahydro-2,6 methanobenzo[d]azocin-1(2H)-one (10)

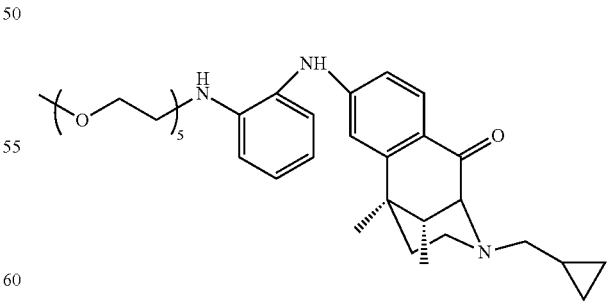

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (100 mg, 0.24 mmol) and N1-(2,5,8,11,14-pentaoxahexadecan-16-yl)benzene-1,2-diamine were dissolved in toluene. BINAP (44.7 mg, 0.0718 mmol), Pd₂dba₃ (43.86 mg, 0.0479 mmol) & Cs₂CO₃ (109.25 mg, 0.3353 mmol) were added to the above mixture and heated to 110° C. for 2 h. The mixture was cooled to room temperature and concentrated under vacuum. Crude was purified by flash chromatography to yield (2S,6R,11R)-8-((4-(2,5,8,11,14-pentaoxahexadecan-16-ylamino)phenyl) amino)-3-(cyclopropylmethyl)-6,11-dimethyl-3,4,5,6-tetrahydro-2,6 methanobenzo[d]azocin-1(2H)-one (10) (93 mg, 63% yield). ¹H NMR (500 MHz, CDCl₃): δ 7.83 (d, 1H), 7.12-7.18 (m, 2H), 6.70-6.75 (m, 2H), 6.58-6.61 (m, 2H), 5.95 (s, 1H), 4.45 (bs, 1H), 3.63-3.68 (m, 2H), 3.55-3.62 (m, 14H), 3.49-3.54 (m, 2H), 3.33 (m, 5H), 3.21 (m, 1H), 2.9-2.94 (m, 1H), 2.72-2.76 (m, 1H), 1.96-2.15 (m, 3H), 1.41-1.44 (m, 1H), 1.37 (s, 3H), 1.25 (m, 1H), 0.88-0.90 (m, 3H), 0.46-0.48 (m, 2H), 0.25-0.27 (m, 1H), 0.07 (m, 2H); MS (ESI) for C₃₅H₅₁N₃O₆: 610.3262 (MH⁺). The free base was dissolved in 4M hydrochloride in 2-propanol. The mixture was concentrated to afford product as hydrochloride salt.

Example 11

Preparation of (2S,6R,11R)-8-((3-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one (11)

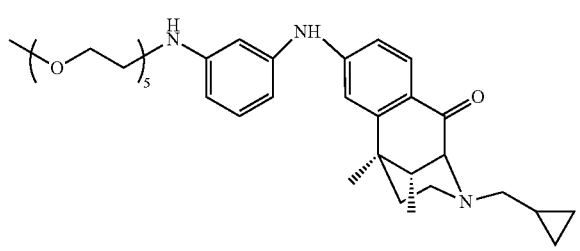

(11)

(2S,6R,11R)-8-((3-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one (8) was prepared according to the following steps.

Step 1: Preparation of N1-(2,5,8,11,14-pentaoxahexadecan-16-yl)benzene-1,3-diamine

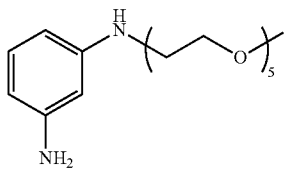

N1-(2,5,8,11,14-pentaoxahexadecan-16-yl)benzene-1,3-diamine was prepared in a manner similar to steps 1-3 of example 7, with the exception that Benzene-1,3-diamine was used as the starting material in step 1 in order to arrive at the present orientation on the phenyl ring to yield N1-(2,5,8,11,14-pentaoxahexadecan-16-yl)benzene-1,3-diamine, as a dark brown gum (1.8 g, 94% yield)

Step 2: Preparation of (2S,6R,11R)-8-((3-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one (11)

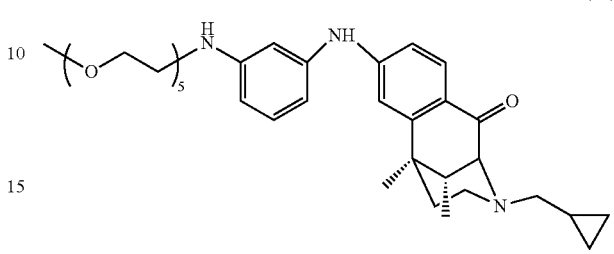

(11)

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (prepared in a manner similar to Example 7, Step 4) (200 mg, 0.479 mmol) and N1-(2,5,8,11,14-pentaoxahexadecan-16-yl)benzene-1,3-diamine (147.66 mg, 0.431 mmol) were dissolved in toluene. DPPF (53.11 mg, 0.0958 mmol), Pd₂dba₃ (29.83 mg, 0.0325 mmol) & sodium tert-butoxide (55.24 mg, 0.575 mmol) were added to the above mixture. The reaction mix was heated to 110° C. and stirred at that temperature for 3 h. Thereafter the mixture was cooled to room temperature and concentrated under vacuum. Crude was purified by preparative HPLC; giving (2S,6R,11R)-8-((3-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one (11) (95 mg, 32% yield). ¹H NMR (500 MHz, CDCl₃): δ 7.87 (d, 1H), 7.12 (t, 1H), 6.90-6.92 (m, 1H), 6.82 (d, 1H), 6.53-6.55 (m, 1H), 6.44-6.45 (m, 1H), 6.35-6.37 (m, 1H), 6.19 (s, 1H), 4.3 (bs, 1H), 3.69-3.71 (t, 2H), 3.62-3.65 (m, 14H), 3.53-3.55 (m, 2H), 3.36 (s, 3H), 3.28 (t, 2H), 3.23 (m, 1H), 2.92-2.94 (m, 1H), 2.72-2.76 (m, 1H), 2.14-2.06 (m, 1H), 1.93-2.10 (m, 3H), 1.49-1.51 (m, 1H), 1.37 (s, 3H), 1.25-1.29 (m, 1H), 0.89-0.91 (m, 3H), 0.44-0.50 (m, 2H), 0.25-0.27 (m, 1H), 0.05-0.07 (m, 1H); MS (ESI) for C₃₅H₅₁N₃O₆: 610.3419 (MH⁺). The free base was dissolved in 4M hydrochloride in 2-propanol. The mixture was concentrated to afford product as hydrochloride salt.

Example 12

Preparation of (2S,6R,11R)-8-((4-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one (12)

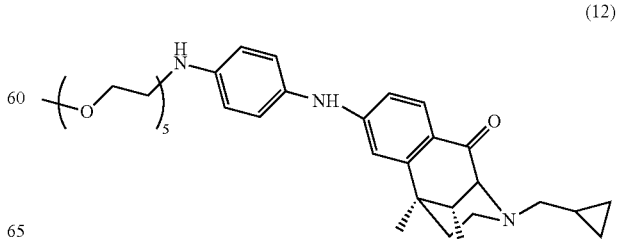

(12)

(2S,6R,11R)-8-((4-(2,5,8,11,14-pentaoxahexadecan-16-ylamino)phenyl)amino)-3-(cyclopropylmethyl)-6,11-dimethyl-3,4,5,6-tetrahydro-2,6-methanobenzo[d]azocin-1(2H)-one (12) was prepared according to the following steps.

Step 1: N1-(2,5,8,11,14-pentaoxahexadecan-16-yl)benzene-1,4-diamine

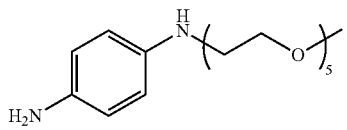

was prepared in a manner similar to steps 1-3 of Example 8, with the exception that benzene-1,4-diamine was used as the starting material in step 1 in order to arrive at the present orientation on the phenyl ring to arrive at N1-(2,5,8,11,14-pentaoxahexadecan-16-yl)benzene-1,4-diamine as dark brown gum (3.1 g, 98% yield)

Step 2: Preparation of (2S,6R,11R)-8-((4-(2,5,8,11,14-pentaoxahexadecan-16-ylamino) phenyl)amino)-3-(cyclopropylmethyl)-6,11-dimethyl-3,4,5,6-tetrahydro-2,6-methanobenzo[d]azocin-1(2H)-one (12)

(12)

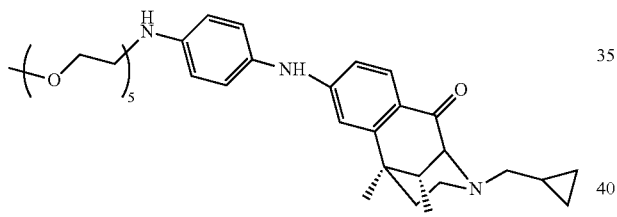

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (prepared in a manner similar to Example 7, Step 4) (3.6 g, 8.62 mmol) and N1-(2,5,8,11,14-pentaoxahexadecan-16-yl)benzene-1,4-diamine (2.95 g, 8.62 mmol) were dissolved in toluene. BINAP (1.61 g, 2.58 mmol), Pd$_2$dba$_3$ (1.58 g, 1.72 mmol) & Cs$_2$CO$_3$ (3.93 g, 8.62 mmol) were added to the above mixture. The reaction mixture was heated to 110° C. and was stirred for 2 h. The mixture was cooled to room temperature and concentrated under vacuum. Crude was purified by flash chromatography to yield (2S,6R,11R)-8-((4-(2,5,8,11,14-pentaoxahexadecan-16-ylamino) phenyl)amino)-3-(cyclopropylmethyl)-6,11-dimethyl-3,4,5,6-tetrahydro-2,6-methanobenzo[d]azocin-1(2H)-one (12) (1.7 g, 33.7% yield). $^1$H NMR (500 MHz, CDCl$_3$): δ 7.83 (d, 1H), 7.03 (d, 2H), 6.64-6.66 (m, 3H), 6.82 (d, 1H), 5.87 (s, 1H), 4.18 (bs, 1H), 3.72-3.74 (t, 2H), 3.63-3.67 (m, 14H), 3.53-3.55 (m, 2H), 3.37 (s, 3H), 3.30 (t, 2H), 3.21 (m, 1H), 2.88-2.96 (m, 1H), 2.72-2.76 (m, 1H), 1.93-2.10 (m, 4H), 1.48-1.50 (m, 1H), 1.37 (s, 3H), 1.25 (m, 1H), 0.88-0.90 (m, 3H), 0.44-0.50 (m, 2H), 0.25-0.27 (m, 1H), 0.05-0.07 (m, 1H); MS (ESI) for C$_{35}$H$_{51}$N$_3$O$_6$: 610.3393 (MH$^+$). The free base was dissolved in 4M hydrochloride in 2-propanol. The mixture was concentrated to afford product as hydrochloride salt.

Example 13

Preparation of (6S,10R,12R)-2-(2,5,8,11,14-pentaoxahexadecan-16-ylamino)-7-(cyclopropylmethyl)-10,12-dimethyl-7,8,9,10-tetrahydro-6,10-methanothiazolo[4',5':4,5]benzo[1,2-d]azocin-5(6H)-one, hydrochloride salt (13)

(13)

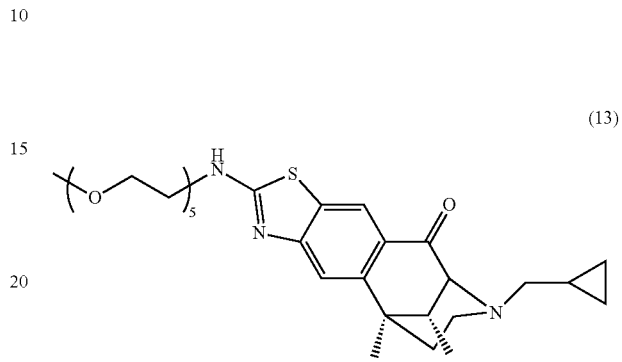

(6S,10R,12R)-2-(2,5,8,11,14-pentaoxahexadecan-16-ylamino)-7-(cyclopropylmethyl)-10,12-dimethyl-7,8,9,10-tetrahydro-6,10-methanothiazolo[4',5':4,5]benzo[1,2-d]azocin-5(6H)-one, hydrochloride salt (13) was prepared according to the following steps.

Step 1: Preparation of (6S,10R,12R)-2-amino-7-(cyclopropylmethyl)-10,12-dimethyl-7,8,9,10-tetrahydro-6,10-methanothiazolo[4',5':4,5]benzo[1,2-d]azocin-5(6H)-one

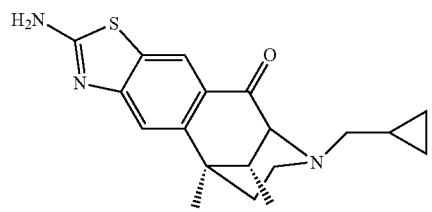 [SMILES: C[C@H]1C2C(=O)c3cc4sc(N)nc4cc3[C@]1(C)CCN2CC1CC1]

(2S,6R,11R)-8-amino-3-(cyclopropylmethyl)-6,11-dimethyl-3,4,5,6-tetrahydro-2,6-methanobenzo[d]azocin-1(2H)-one (synthesized as per Example 15, Step 3) (160 mg, 0.56 mmol) and potassium thiocyanate (280 mg, 2.88 mmol) were sonicated in 5 mL of acetic acid for 2 minutes. 8.9M Bromine in acetic acid (0.07 mL, 0.62 mmol) was then added into the solution. The mixture was stirred for 3 hours at 60° C. and then was concentrated. The residue was dissolved in dichloromethane (10 mL) and filtered, washed with 5N aqueous sodium hydroxide (2×30 mL), water (30 mL) and was dried over sodium sulfate. Evaporation of the solvent and purification of the residue by recrystallization in dichloromethane yielded (6S,10R,12R)-2-amino-7-(cyclopropylmethyl)-10,12-dimethyl-7,8,9,10-tetrahydro-6,10-methanothiazolo[4',5':4,5]benzo[1,2-d]azocin-5(6H)-one (180 mg, 94% yield).

Step 2: Preparation of tert-butyl ((6S,10R,12R)-7-(cyclopropylmethyl)-10,12-dimethyl-5-oxo-5,6,7,8,9,10-hexahydro-6,10-methanothiazolo[4',5':4,5]benzo[1,2-d]azocin-2-yl)carbamate

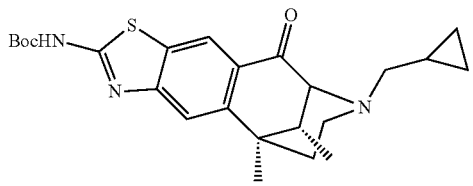 [SMILES: C[C@H]1C2C(=O)c3cc4sc(NC(=O)OC(C)(C)C)nc4cc3[C@]1(C)CCN2CC1CC1]

(6S,10R,12R)-2-amino-7-(cyclopropylmethyl)-10,12-dimethyl-7,8,9,10-tetrahydro-6,10-methanothiazolo[4',5':4,5]benzo[1,2-d]azocin-5(6H)-one (180 mg, 0.15 mmol), triethyl amine (0.184 mL, 1.318 mmol) and dimethylamino pyridine (12 mg, 0.1 mmol) were dissolved in 2 mL of tetrahydrofuran. The reaction mixture was stirred at room temperature for 10 min and then to it was added di-tert-butyl dicarbonate (150 mg, 0.68 mmol). The mixture was stirred for 4 hours at 60° C. and concentrated. The residue was purified by flash chromatography to yield tert-butyl ((6S,10R,12R)-7-(cyclopropylmethyl)-10,12-dimethyl-5-oxo-5,6,7,8,9,10-hexahydro-6,10-methanothiazolo[4',5':4,5]benzo[1,2-d]azocin-2-yl)carbamate (80 mg, 34% yield).

Step 3: Preparation of tert-butyl ((6S,10R,12R)-7-(cyclopropylmethyl)-10,12-dimethyl-5-oxo-5,6,7,8,9,10-hexahydro-6,10-methanothiazolo[4',5':4,5]benzo[1,2-d]azocin-2-yl)(2,5,8,11,14-pentaoxahexadecan-16-yl)carbamate

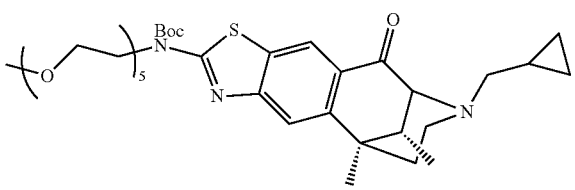

tert-butyl ((6S,10R,12R)-7-(cyclopropylmethyl)-10,12-dimethyl-5-oxo-5,6,7,8,9,10-hexahydro-6,10-methanothiazolo[4',5':4,5]benzo[1,2-d]azocin-2-yl)carbamate (80 mg, 0.18 mmol), triphenyl phosphine (57 mg, 0.21 mmol), and mPEG$_5$-OH (45 mg, 0.18 mmol) were dissolved in 2 mL of dichloromethane. The mixture was stirred for 5 minutes at room temperature and then cooled to 0° C. Diisopropyl azodicarboxylate (DIAD) (0.46 mL, 0.23 mmol) was added into the solution. The reaction mixture was stirred for 18 hours and then was concentrated. The residue was purified by flash chromatography to yield tert-butyl ((6S,10R,12R)-7-(cyclopropylmethyl)-10,12-dimethyl-5-oxo-5,6,7,8,9,10-hexahydro-6,10-methanothiazolo[4',5':4,5]benzo[1,2-d]azocin-2-yl)(2,5,8,11,14-pentaoxahexadecan-16-yl)carbamate (70 mg, 57% yield).

Step 4: Preparation of (6S,10R,12R)-2-(2,5,8,11,14-pentaoxahexadecan-16-ylamino)-7-(cyclopropylmethyl)-10,12-dimethyl-7,8,9,10-tetrahydro-6,10-methanothiazolo[4',5':4,5]benzo[1,2-d]azocin-5(6H)-one, hydrochloride salt (13)

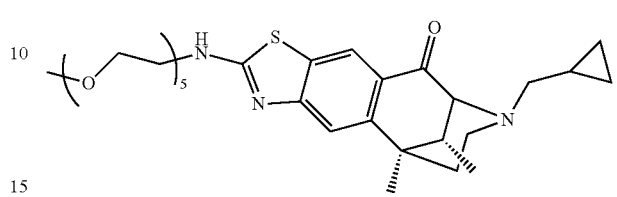

tert-butyl ((6S,10R,12R)-7-(cyclopropylmethyl)-10,12-dimethyl-5-oxo-5,6,7,8,9,10-hexahydro-6,10-methanothiazolo[4',5':4,5]benzo[1,2-d]azocin-2-yl)(2,5,8,11,14-pentaoxahexadecan-16-yl)carbamate (110 mg, 0.16 mmol) was dissolved in 1 mL of 4N hydrochloride in 2-propanol and stirred at room temperature for 1 hour, and concentrated. The residue partitioned between saturated sodium bicarbonate and dichloromethane, and the organic layer dried on sodium sulfate. Evaporation of solvent yielded (6S,10R,12R)-2-(2,5,8,11,14-pentaoxahexadecan-16-ylamino)-7-(cyclopropylmethyl)-10,12-dimethyl-7,8,9,10-tetrahydro-6,10-methanothiazolo[4',5':4,5]benzo[1,2-d]azocin-5(6H)-one (13) (80 mg, 85% yield). $^1$H NMR (500 MHz, CDCl$_3$): δ 8.21 (s, 1H), 7.42 (s, 1H), 6.71 (bs, 1H), 3.75-3.62 (m, 19H), 3.56-3.54 (m, 2H), 3.36 (s, 3H), 3.27 (d, 1H), 2.92-2.89 (m, 1H), 2.73 (dd, 1H), 2.17-2.14 (m, 1H), 2.03-1.96 (m, 2H), 1.51-1.53 (m, 1H), 1.47 (s, 3H), 0.88 (d, 3H), 0.89-0.86 (m, 2H), 0.49-0.46 (m, 2H), 0.26-0.24 (m, 1H), 0.06-0.04 (m, 1H). MS (ESI) for C$_{30}$H$_{45}$N$_3$O$_6$S: 576 (MH$^+$). The free base was dissolved in 1 mL of 4M hydrochloride in 2-propanol. The mixture was concentrated to afford product as hydrochloride salt.

Example 14

Preparation of (2S,6R,11R)-8-hydroxy-3-(2-(2-methoxyethoxy)ethyl)-6,11-dimethyl-3,4,5,6-tetrahydro-2,6-methanobenzo[d]azocin-1(2H)-one (14)

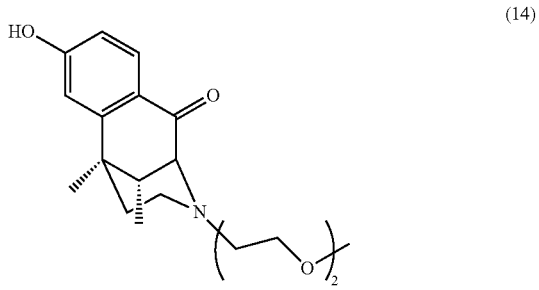

(14)

(2S,6R,11R)-8-hydroxy-3-(2-(2-methoxyethoxy)ethyl)-6,11-dimethyl-3,4,5,6-tetrahydro-2,6-methanobenzo[d]azocin-1(2H)-one (14) was prepared according to the following steps.

Step 1: (2S,6R,11R)-3-(cyclopropylmethyl)-6,11-dimethyl-1-oxo-1,2,3,4,5,6-hexahydro-2,6-methano-benzo[d]azocin-8-yltrifluoromethanesulfonate

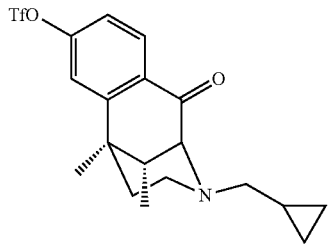 [SMILES: C[C@H]1C2C(=O)c3ccc(OS(=O)(=O)C(F)(F)F)cc3[C@]1(C)CCN2CC1CC1]

was prepared in a manner similar to Example 7, Step 4.

Step 2: Preparation of (2S,6R,11R)-8-hydroxy-3-(2-(2-methoxyethoxy)ethyl)-6,11-dimethyl-3,4,5,6-tetrahydro-2,6-methanobenzo[d]azocin-1(2H)-one (14)

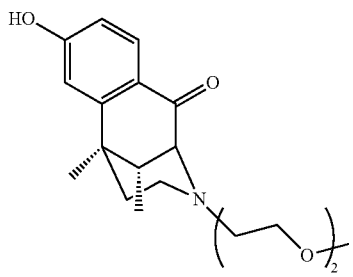

(14)

(2S,6R,11R)-6,11-dimethyl-1-oxo-1,2,3,4,5,6-hexahydro-2,6-methanobenzo[d]azocin-8-yl trifluoromethanesulfonate hydrochloride (120 mg, 0.33 mmol), $Cs_2CO_3$ (214.9 mg, 0.6494 mmol) and $mPEG_2$-Br (78.45 mg, 0.4286 mmol) were dissolved in acetonitrile. The mixture was heated to 75° C. for 16 h and cooled to room temperature. The mixture was concentrated under vacuum and purified by flash chromatography to yield (2S,6R,11R)-8-hydroxy-3-(2-(2-methoxyethoxy) ethyl)-6,11-dimethyl-3,4,5,6-tetrahydro-2,6-methanobenzo[d]azocin-1(2H)-one (14) (51.5 mg, 47% yield). $^1$H NMR (500 MHz, $CDCl_3$): δ 8.02 (d, 1H), 6.85 (m, 2H), 4.21-4.23 (m, 2H), 3.89 (t, 2H), 3.57-3.59 (m, 2H), 3.39 (s, 3H), 3.27 (d, 1H), 2.72-2.75 (m, 1H), 2.55-2.61 (m, 1H), 2.08-2.13 (m, 1H), 1.87-1.94 (m, 1H), 1.45-1.48 (m, 1H), 1.41 (s, 3H), 0.85 (d, 3H); MS (ESI) for $C_{19}H_{27}NO_4$: 334.1965 ($MH^+$). The free base was dissolved in 4M hydrochloride in 2-propanol. The mixture was concentrated to afford product as hydrochloride salt.

Example 15

Preparation of N-((2S,6R,11R)-3-(cyclopropylmethyl)-6,11-dimethyl-1-oxo-1,2,3,4,5,6-hexahydro-2,6-methanobenzo[d]azocin-8-yl)-2-(2-methoxyethoxy)acetamide (15)

(15)

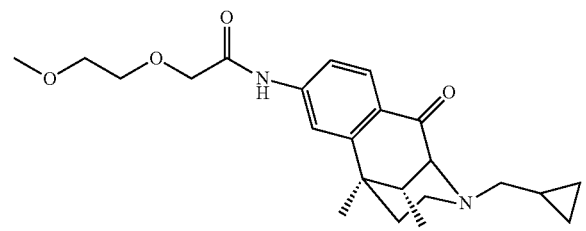

N-((2S,6R,11R)-3-(cyclopropylmethyl)-6,11-dimethyl-1-oxo-1,2,3,4,5,6-hexahydro-2,6-methanobenzo[d]azocin-8-yl)-2-(2-methoxyethoxy)acetamide (15) was prepared according to the following steps.

Step 1: (2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate

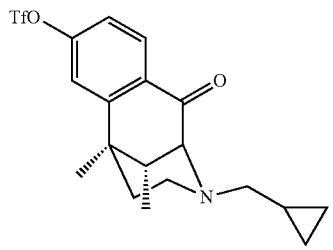 [SMILES: C[C@H]1C2C(=O)c3ccc(OS(=O)(=O)C(F)(F)F)cc3[C@]1(C)CCN2CC1CC1]

was prepared in a manner similar to Example 7, step 4.

Step 2: Preparation of (2S,6R,11R)-3-(cyclopropylmethyl)-8-((diphenylmethylene) amino)-6,11-dimethyl-3,4,5,6-tetrahydro-2,6-methanobenzo[d]azocin-1(2H)-one

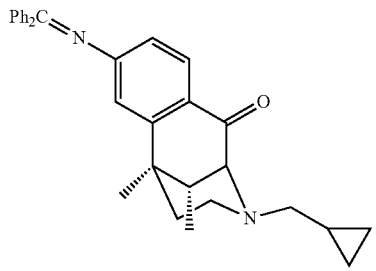

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (450 mg, 1.08 mmol) and benzophenone imine (292.7 mg, 1.61 mmol) were dissolved in 2 mL of toluene. BINAP (134.25 mg, 0.21 mmol), $Pd_2dba_3$ (177.7 mg, 0.19 mmol) & $Cs_2CO_3$ (1053.7 mg, 3.23 mmol) were added to the above reaction mixture and heated to 110° C. for 8-10 h. Reaction mixture was concentrated, the crude thus obtained was purified by column chromatography; yielding (2S,6R,11R)-3-(cyclopropylmethyl)-8-((diphenylmethylene)amino)-6,11-dimethyl-3,4,5,6-tetrahydro-2,6-methanobenzo[d]azocin-1(2H)-one (400 mg, 83% yield).

Step 3: Preparation of (2S,6R,11R)-8-amino-3-(cyclopropylmethyl)-6,11-dimethyl-3,4,5,6-tetrahydro-2,6-methanobenzo[d]azocin-1(2H)-one

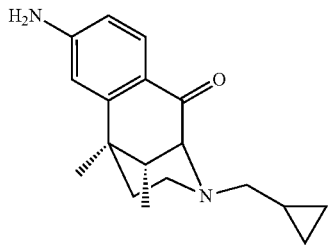

(2S,6R,11R)-3-(cyclopropylmethyl)-8-((diphenylmethylene)amino)-6,11-dimethyl-3,4,5,6-tetrahydro-2,6-methanobenzo[d]azocin-1(2H)-one (400 mg, 0.89 mmol), hydroxylamine hydrochloride (124 mg, 1.78 mmol) and sodium ethoxide (220 mg, 2.67 mmol) were dissolved in 10 mL of MeOH. The reaction mixture was stirred for 20 h and concentrated. The residue was partitioned between 5 M HCl (10 mL) & ethyl acetate (10 mL). The Aq. layer was washed with MTBE and retained. The pH of aqueous layer was adjusted to 11 and the product was extracted into dichloromethane. DCM layer was dried over anhydrous Sodium sulfate. and concentrated under vacuum to get (2S,6R,11R)-8-amino-3-(cyclopropylmethyl)-6,11-dimethyl-3,4,5,6-tetrahydro-2,6-methanobenzo[d]azocin-1(2H)-one, as a light yellow syrup (221 mg, 87% yield).

Step 4: Preparation of 2-(2-methoxyethoxy)acetic Acid

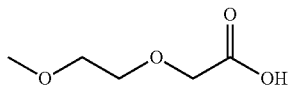

2-Methoxyethanol (10 g, 131.4 mmol) and potassium tert-butoxide (17.67 g, 157.68 mmol) were dissolved in 100 mL of THF. The mixture was heated to 45° C. for 1 h and cooled to room temperature. tert-Butylbromo acetate (25.63 g, 131.41 mmol) was added to the above mixture and stirred for 16 h at room temperature. Reaction mixture was concentrated, the residue dissolved in water. pH of the aq. layer was adjusted to 12-12.5 (using 1M aq. NaOH) and stirred for 12-14 h at room temperature. Thereafter, pH of the aq. layer was adjusted to 2 using 10% aq. phosphoric acid. Product was extracted into DCM. Recovery of DCM on a rotovap yielded 2-(2-methoxyethoxy)acetic acid, as an oily mass (4.1 g, 23% yield).

Step 5: Preparation of N-((2S,6R,11R)-3-(cyclopropylmethyl)-6,11-dimethyl-1-oxo-1,2,3,4,5,6-hexahydro-2,6-methanobenzo[d]azocin-8-yl)-2-(2-methoxyethoxy)acetamide (15)

(15)

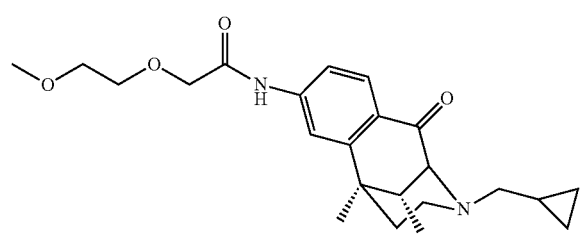

(2S,6R,11R)-8-amino-3-(cyclopropylmethyl)-6,11-dimethyl-3,4,5,6-tetrahydro-2,6-methanobenzo[d]azocin-1(2H)-one (150 mg, 0.527 mmol), 2-(2-methoxyethoxy)acetic acid (5) (106 mg, 0.79 mmol) and HOBT (93 mg, 0.68 mmol) were dissolved in 8 mL of dichloromethane. DCC (131 mg, 0.633 mmol) was added and the mixture was stirred for 70 h. RM was filtered through Celite and the bed, washed with DCM. The filtrate was concentrated and purified using preparative HPLC to get N-((2S,6R,11R)-3-(cyclopropylmethyl)-6,11-dimethyl-1-oxo-1,2,3,4,5,6-hexahydro-2,6-methanobenzo[d]azocin-8-yl)-2-(2-methoxyethoxy)acetamide (15) as a yellow gum (84 mg, 40% yield). $^1$H NMR (500 MHz, CDCl$_3$): δ 9.957 (s, 1H), 7.8 (d, 1H), 7.68-7.70 (m, 2H), 4.1 (s, 2H), 3.66-3.68 (m, 2H), 3.52-3.54 (m, 2H), 3.3 (s, 3H), 3.15 (d, 1H), 2.78-2.81 (m, 1H), 2.45-2.48 (m, 1H), 2.05-2.06 (m, 1H), 1.82-1.96 (m, 2H), 1.41-1.44 (m, 1H), 1.37 (s, 3H), 0.9 (m, 1H), 0.77-0.83 (m, 3H), 0.39-0.46 (m, 2H), 0.18-0.21 (m, 1H), 0.01-0.02 (m, 2H); MS (ESI) for C$_{23}$H$_{32}$N$_2$O$_4$: 400.2005 (MH$^+$). The free base was dissolved in 4M hydrochloride in 2-propanol. The mixture was concentrated to afford product as hydrochloride salt.

Example 16

Preparation of (2S,6R,11R)-3-(cyclopropylmethyl)-N-(2-methoxyethyl)-6,11-dimethyl-1-oxo-1,2,3,4,5,6-hexahydro-2,6-methanobenzo[d]azocine-8-carboxamide (16)

(16)

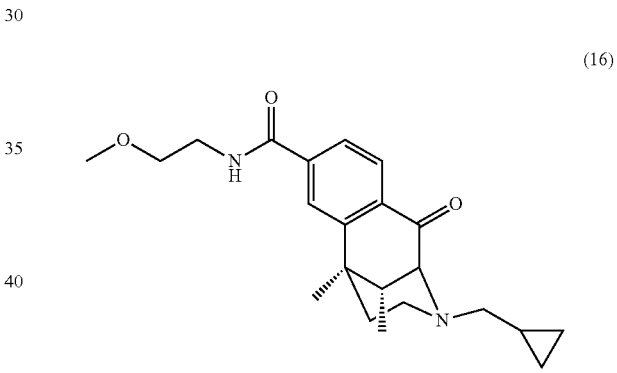

(2S,6R,11R)-3-(cyclopropylmethyl)-N-(2-methoxyethyl)-6,11-dimethyl-1-oxo-1,2,3,4,5,6-hexahydro-2,6-methanobenzo[d]azocine-8-carboxamide (16) was prepared according to the following steps.

Step 1: (2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate

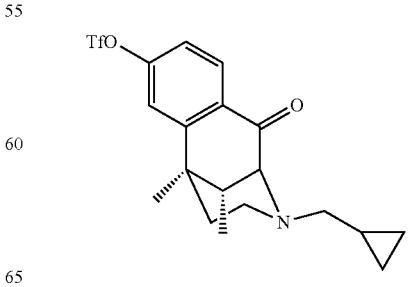

was prepared in a manner similar to Example 7, step 4.

Step 2: Preparation of (2S,6R,11R)-3-(cyclopropylmethyl)-6,11-dimethyl-1-oxo-1,2,3,4,5,6-hexahydro-2,6-methanobenzo[d]azocine-8-carbonitrile

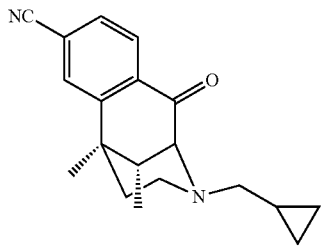 [SMILES: C[C@H]1C2C(=O)c3ccc(C#N)cc3[C@]1(C)CCN2CC1CC1]

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (800 mg, 1.92 mmol), Zn(CN)$_2$ (1351 mg, 5.75 mmol) and Pd(PPh$_3$)$_4$ (886 mg, 0.77 mmol) were dissolved in 10 mL of DMF in sealed tube. The mixture was heated to 130° C. for 5 h and cooled to room temperature. DMF was concentrated under vacuum and residue was dissolved in water. Aq. layer was extracted with EtOAc, The organic layer was dried over sodium sulfate and concentrated under vacuum. The residue was purified by column chromatography; to afford (2S,6R,11R)-3-(cyclopropylmethyl)-6,11-dimethyl-1-oxo-1,2,3,4,5,6-hexahydro-2,6-methanobenzo[d]azocine-8-carbonitrile (520 mg, 92% yield).

Step 3: (2S,6R,11R)-3-(cyclopropylmethyl)-6,11-dimethyl-1-oxo-1,2,3,4,5,6-hexahydro-2,6-methanobenzo[d]azocine-8-carboxylic Acid

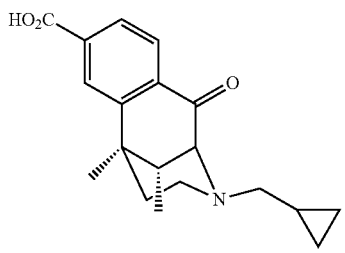 [SMILES: C[C@H]1C2C(=O)c3ccc(C(=O)O)cc3[C@]1(C)CCN2CC1CC1]

(2S,6R,11R)-3-(cyclopropylmethyl)-6,11-dimethyl-1-oxo-1,2,3,4,5,6-hexahydro-2,6-methano benzo[d]azocine-8-carbonitrile (120 mg, 0.410 mmol) was dissolved in MeOH. 25% aq. KOH (5 mL) and 30% H$_2$O$_2$ (1 mL) were added to it. Reaction mix was stir heated at 85° C. for 15 h. Reaction mixture was cooled to room temperature and diluted with water (5 mL). pH of the above mixture was adjusted to 2-3 using 1 M aq. HCl. Compound was extracted into EtOAc, dried over anhydrous sodium sulfate and the ethyl acetate layer was concentrated under vacuum to afford (2S,6R,11R)-3-(cyclopropylmethyl)-6,11-dimethyl-1-oxo-1,2,3,4,5,6-hexahydro-2,6-methanobenzo[d]azocine-8-carboxylic acid (120 mg, 94% yield)

Step 4: (2S,6R,11R)-3-(cyclopropylmethyl)-N-(2-methoxyethyl)-6,11-dimethyl-1-oxo-1,2,3,4,5,6-hexahydro-2,6-methanobenzo[d]azocine-8-carboxamide

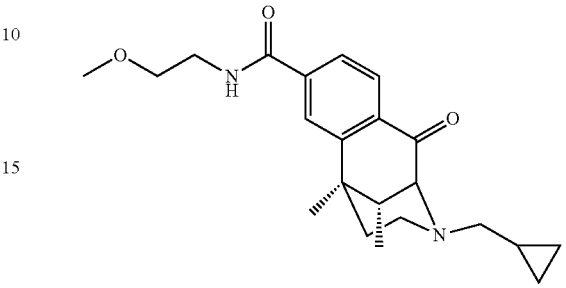

(16)

(2S,6R,11R)-3-(cyclopropylmethyl)-6,11-dimethyl-1-oxo-1,2,3,4,5,6-hexahydro-2,6-methanobenzo[d]azocine-8-carboxylic acid (120 g, 0.383 mmol), mPEG$_1$-NH$_2$ (31.6 mg, 0.421 mmol) and TEA (0.067 mL, 0.479 mmol) was dissolved in 1.2 mL of DCM. HOBt (62 mg, 0.46 mmol) and DCC (79 mg, 0.383 mmol) were added to the above mixture and stirred for 4 h at room temperature. Reaction mixture was filtered through celite and concentrated under vacuum to a residue. Residue was purified by column chromatography to yield (2S,6R,11R)-3-(cyclopropylmethyl)-N-(2-methoxyethyl)-6,11-dimethyl-1-oxo-1,2,3,4,5,6-hexahydro-2,6-methanobenzo[d]azocine-8-carboxamide (16) (130 mg, 92% yield). $^1$H NMR (500 MHz, DMSO-D6): δ 8.72 (t, 1H), 7.85-7.90 (m, 2H), 7.79-7.81 (m, 1H), 3.42-3.48 (m, 4H), 3.27 (s, 3H), 3.23 (m, 1H), 2.80-2.83 (m, 1H), 2.10-2.12 (m, 1H), 1.94-1.98 (m, 2H), 1.60-1.78 (m, 3H), 1.24 (s, 3H), 0.84-0.88 (m, 1H), 0.77 (d, 3H), 0.40-0.47 (m, 2H), 0.19-0.21 (m, 1H), 0.01-0.03 (m, 1H); MS (ESI) for C$_{22}$H$_{30}$N$_2$O$_3$: 371.1961 (MH$^+$). The free base was dissolved in 4M hydrochloride in 2-propanol. The mixture was concentrated to afford product as hydrochloride salt.

Example 17

Preparation of N,N-(((2S,6R,11R)-3-(cyclopropylmethyl)-6,11-dimethyl-1-oxo-1,2,3,4,5,6-hexahydro-2,6-methanobenzo[d]azocin-8-yl)methyl)-2-(2-methoxyethoxy)acetamide (17)

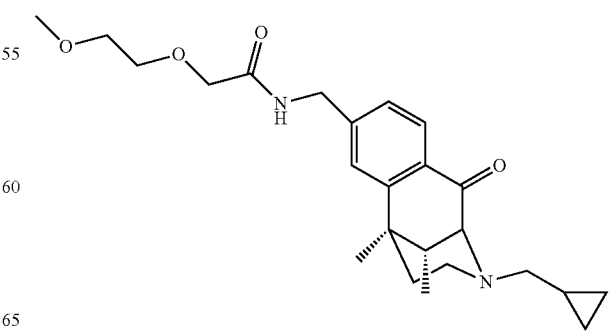

(17)

N,N-(((2S,6R,11R)-3-(cyclopropylmethyl)-6,11-dimethyl-1-oxo-1,2,3,4,5,6-hexahydro-2,6-methanobenzo[d]azocin-8-yl)methyl)-2-(2-methoxyethoxy)acetamide (17) was prepared according to the following steps.

Step 1: Preparation of (2S,6R,11R)-8-(aminomethyl)-3-(cyclopropylmethyl)-6,11-dimethyl-3,4,5,6-tetrahydro-2,6-methanobenzo[d]azocin-1(2H)-one

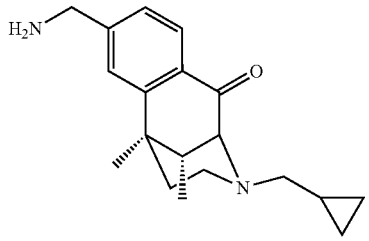 [SMILES: C[C@H]1C2C(=O)c3ccc(CN)cc3[C@]1(C)CCN2CC1CC1]

(2S,6R,11R)-3-(cyclopropylmethyl)-6,11-dimethyl-1-oxo-1,2,3,4,5,6-hexahydro-2,6-methano benzo[d]azocine-8-carbonitrile (320 mg, 1.09 mmol), prepared in a manner similar to Example 16, step 2, was dissolved in methanol. 10% Pd/C (~50% wet) (50 mg) was added to the above mixture and reaction was under hydrogen balloon pressure for 4 h. Reaction mixture was filter through celite bed, the bed washed with methanol. Organic layer was concentrated under vacuum to yield (2S,6R,11R)-8-(aminomethyl)-3-(cyclopropylmethyl)-6,11-dimethyl-3,4,5,6-tetrahydro-2,6-methanobenzo[d]azocin-1(2H)-one (320 mg, 99% yield).

Step 2: Preparation of N,N-(((2S,6R,11R)-3-(cyclopropylmethyl)-6,11-dimethyl-1-oxo-1,2,3,4,5,6-hexahydro-2,6-methanobenzo[d]azocin-8-yl)methyl)-2-(2-methoxyethoxy) acetamide

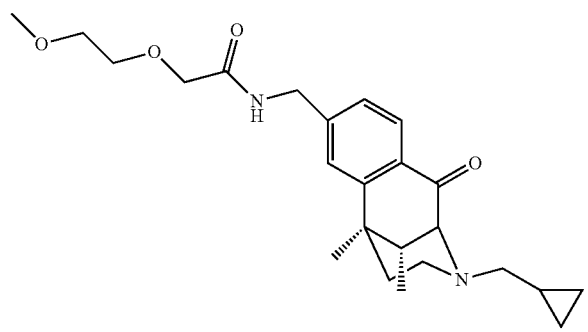 [SMILES: COCCOCC(=O)NCc1ccc2c(c1)[C@]1(C)CCN(CC3CC3)C(C2=O)[C@@H]1C]

(2S,6R,11R)-8-(aminomethyl)-3-(cyclopropylmethyl)-6,11-dimethyl-3,4,5,6-tetrahydro-2,6-methanobenzo[d]azocin-1(2H)-one (110 mg, 0.37 mmol), 2-(2-methoxyethoxy) acetic acid (64.3 mg, 0.48 mmol) and TEA (0.8 mL, 0.461 mmol) were dissolved in 1 mL of DCM. The mixture was stirred for 10 min. Following which, HOBT (59.7 mg, 0.442 mmol) and DCC (114 mg, 0.553 mmol) were added and stirring was continued for another 2 h. Reaction mixture was filtered and concentrated under vacuum to get a residue. The residue was purified by column chromatography to afford N,N-(((2S,6R,11R)-3-(cyclopropylmethyl)-6,11-dimethyl-1-oxo-1,2,3,4,5,6-hexahydro-2,6-methanobenzo[d]azocin-8-yl)methyl)-2-(2-methoxyethoxy)acetamide (17) (62 mg, 41% yield). $^1$H NMR (500 MHz, CDCl$_3$): δ 8.1 (m, 1H), 7.5 (m, 1H), 7.21-7.23 (m, 2H), 3.88 (s, 2H), 3.6-3.7 (m, 4H), 3.55 (s, 2H), 3.37 (s, 3H), 2.85 (m, 1H), 2.92-2.95 (m, 1H), 2.63-2.67 (m, 1H), 1.93-2.22 (m, 4H), 1.45 (s, 3H), 1.25 (m, 1H), 0.87-0.88 (m, 4H), 0.46-0.53 (m, 2H), 0.26 (m, 1H), 0.04-0.07 (m, 1H); MS (ESI) for C$_{24}$H$_{34}$N$_2$O$_4$: 415.2243 (MH$^+$). The free base was dissolved in 4M hydrochloride in 2-propanol. The mixture was concentrated to afford product as hydrochloride salt.

Example 18

Preparation of (2S,6R,11R)-3-(cyclopropylmethyl)-8-(((2-(2-methoxyethoxy) ethyl)amino)methyl)-6,11-dimethyl-3,4,5,6-tetrahydro-2,6-methanobenzo[d]azocin-1(2H)-one (18)

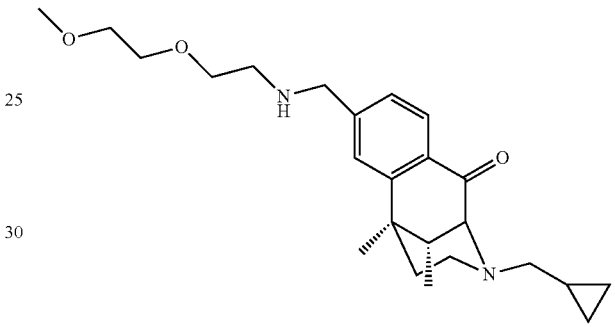

(2S,6R,11R)-3-(cyclopropylmethyl)-8-(((2-(2-methoxyethoxy)ethyl)amino)methyl)-6,11-dimethyl-3,4,5,6-tetrahydro-2,6-methanobenzo[d]azocin-1(2H)-one (18) was prepared according to the following steps.

Step 1: Preparation of (2S,6R,11R)-3-(cyclopropylmethyl)-8-(((2-(2-methoxyethoxy) ethyl)amino)methyl)-6,11-dimethyl-3,4,5,6-tetrahydro-2,6-methanobenzo[d]azocin-1(2H)-one (18)

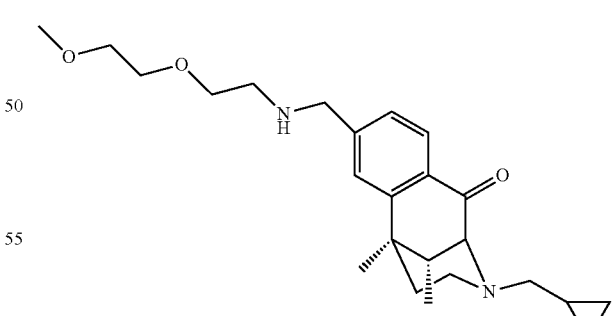

(2S,6R,11R)-8-(aminomethyl)-3-(cyclopropylmethyl)-6,11-dimethyl-3,4,5,6-tetrahydro-2,6-methanobenzo[d]azocin-1(2H)-one (160 mg, 0.54 mmol) prepared in a manner similar to Example 17, step 1, and mPEG$_1$-Br (981 mg, 5.4 mmol) was dissolved in 1.6 mL of DMF. NaOH (214 mg, 5.4 mmol) was added to the above mixture and reaction was stirred for 20 h at room temperature. Reaction mixture was filtered and concentrated under vacuum to get a residue. Residue was purified by column chromatography to yield (2S,6R,11R)-3-(cyclopropylmethyl)-8-(((2-(2-methoxyethoxy) ethyl)amino)methyl)-6,11-dimethyl-3,4,5,6-tetrahydro-2,6-methanobenzo[d]azocin-1(2H)-one (18) as gummy oil (110 mg, 51% yield). $^1$H NMR (500 MHz, CDCl$_3$): δ 7.95 (d, 1H), 7.3 (m, 2H), 3.88 (s, 2H), 3.6-3.7 (m, 4H), 3.52-3.55 (m, 2H), 3.37 (s, 3H), 3.3 (m, 1H), 2.92 (m, 1H), 2.85 (m, 1H), 2.91-2.94 (m, 1H), 2.72-2.76 (m, 1H), 1.97-2.13 (m, 4H), 1.34 (s, 3H), 1.25 (m, 1H), 0.88-0.90 (m, 4H), 0.46-0.48 (m, 2H), 0.26 (m, 1H), 0.04-0.07 (m, 1H), MS (ESI) for C$_{24}$H$_{36}$N$_2$O$_3$: 401.2616 (MH$^+$). The free base was dissolved in 4M hydrochloride in 2-propanol. The mixture was concentrated to afford product as hydrochloride salt.

Example 19

Preparation of (2S,6R,11R)-7-(2,5,8,11,14-pentaoxahexadecan-16-yloxy)-3-(cyclopropylmethyl)-8-hydroxy-6,11-dimethyl-3,4,5,6-tetrahydro-2,6-methanobenzo[d]azocin-1(2H)-one, hydrochloride salt (19)

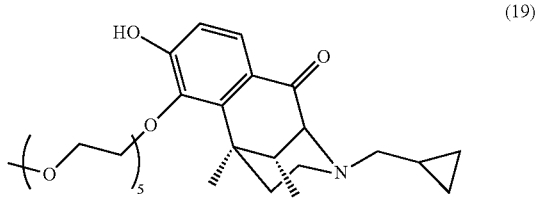

(19)

(2S,6R,11R)-7-(2,5,8,11,14-pentaoxahexadecan-16-yloxy)-3-(cyclopropylmethyl)-8-hydroxy-6,11-dimethyl-3,4,5,6-tetrahydro-2,6-methanobenzo[d]azocin-1(2H)-one, hydrochloride salt (19) was prepared according to the following steps.

Step 1: Preparation of (2S,6R,11R)-7-bromo-3-(cyclopropylmethyl)-8-hydroxy-6,11-dimethyl-3,4,5,6-tetrahydro-2,6-methanobenzo[d]azocin-1(2H)-one

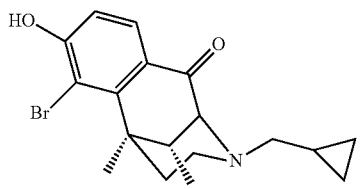 [SMILES: C[C@H]1C2C(=O)c3ccc(O)c(Br)c3[C@]1(C)CCN2CC1CC1]

(2S,6R,11R)-3-(cyclopropylmethyl)-8-hydroxy-6,11-dimethyl-3,4,5,6-tetrahydro-2,6-methanobenzo[d]azocin-1(2H)-one (ketazocine) (400 mg, 1.4 mmol) and 8.9M bromine in acetic acid (0.34 mL, 3.0 mmol) were dissolved in 4 mL of acetic acid. The mixture was stirred for 18 hours at 80° C. and then was concentrated. The residue was dissolved in methanol (10 mL) and charged with 10% palladium-carbon (10% w/w). The mixture was stirred under hydrogen atmosphere for 30 minutes at room temperature. The reaction mixture filtered, evaporation of the solvent and purification of the residue by flash chromatography yielded (2S,6R,11R)-7-bromo-3-(cyclopropylmethyl)-8-hydroxy-6,11-dimethyl-3,4,5,6-tetrahydro-2,6-methanobenzo[d]azocin-1(2H)-one (220 mg, 43% yield).

Step 2: Preparation of (2S,6R,11R)-7-(2,5,8,11,14-pentaoxahexadecan-16-yloxy)-3-(cyclopropylmethyl)-8-hydroxy-6,11-dimethyl-3,4,5,6-tetrahydro-2,6-methanobenzo[d]azocin-1(2H)-one, hydrochloride salt (19)

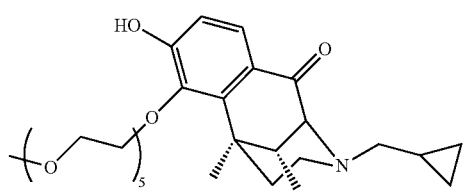

mPEG$_5$-OH (770 mg, 3.0 mmol) was dissolved in 2 mL of toluene:N,N-dimethylformamide (9:1), and sodium hydride (138 mg of 60% in mineral oil, 3.4 mmol) was added into the solution. (2S,6R,11R)-7-bromo-3-(cyclopropylmethyl)-8-hydroxy-6,11-dimethyl-3,4,5,6-tetrahydro-2,6-methanobenzo[d]azocin-1(2H)-one (140 mg, 0.38 mmol) and cuprous iodide (50 mg, 0.26 mmol) were then added under stirring. The reaction mixture was stirred at 120° C. for 3 hours. 15 mL of dichloromethane was added into the reaction mixture. The solution was washed with water (10 mL×3) and was dried over sodium sulfate. Evaporation of the solvent and purification of the residue by flash chromatography yielded (2S,6R,11R)-7-(2,5,8,11,14-pentaoxahexadecan-16-yloxy)-3-(cyclopropylmethyl)-8-hydroxy-6,11-dimethyl-3,4,5,6-tetrahydro-2,6-methanobenzo[d]azocin-1(2H)-one (19) (90 mg, 43% yield). $^1$H NMR (500 MHz, CDCl$_3$): δ 8.8 (bs, 1H), 7.81 (d, 1H), 6.88 (d, 1H), 4.10-4.07 (m, 1H), 3.95-3.82 (m, 5H), 3.76-3.74 (m, 2H), 3.68-3.62 (m, 10H), 3.54-3.52 (m, 2H), 3.37 (s, 3H), 3.24 (bs, 1H), 2.97-2.96 (m, 1H), 2.72 (dd, 1H), 2.05-1.98 (m, 1H), 1.82-1.73 (m, 2H), 1.63 (s, 3H), 0.91 (d, 3H), 0.89-0.86 (m, 2H), 0.49-0.45 (m, 2H), 0.25-0.24 (m, 1H), 0.07-0.04 (m, 1H). MS (ESI) for C$_{29}$H$_{45}$NO$_3$: 536 (MH$^+$). The free base was dissolved in 4M hydrochloride in 2-propanol. Evaporation of volatiles afforded product as hydrochloride salt.

Example 20

Preparation of (2S,6R,11R)-3-(cyclopropylmethyl)-6,11-dimethyl-8-((4-((1,1,1-trifluoro-2,5,8,11,14-pentaoxahexadecan-16-yl)amino)phenyl)amino)-3,4,5,6-tetrahydro-2,6-methanobenzo[d]azocin-1(2H)-one (20)

(20)

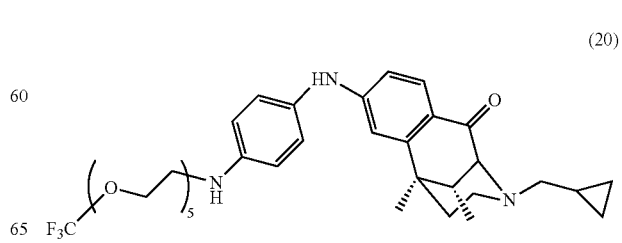

(2S,6R,11R)-3-(cyclopropylmethyl)-6,11-dimethyl-8-((4-((1,1,1-trifluoro-2,5,8,11,14-pentaoxahexadecan-16-yl)amino)phenyl)amino)-3,4,5,6-tetrahydro-2,6-methanobenzo[d]azocin-1(2H)-one (20) was prepared according to the following steps.

Step 1: Preparation of S-methyl O-(1-phenyl-2,5,8,11,14-pentaoxahexadecan-16-yl) carbonodithioate

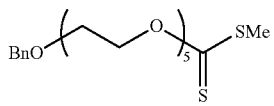

1-Phenyl-2,5,8,11,14-pentaoxahexadecan-16-ol (T. Shiyama et al., Bioorg. Med. Chem. (2004), #12, 2831) (13.0 g, 39.6 mmol) was dissolved in 250 mL of tetrahydrofuran and sodium hydride (1.9 g of 60% in mineral oil, 47.5 mmol) was added into the solution. The mixture was stirred for 10 minutes at room temperature and then cooled to 0° C. Carbon disulfide (3.1 mL, 51.5 mmol) was then added under stirring. The reaction mixture stirred for 1 hour and then methyl iodide (3.2 mL, 51.5 mmol) was added drop wise at 0° C., stirred for 18 h at room temperature, and concentrated. The residue was dissolved in ethyl acetate (200 mL) and was washed with water (2×300 mL), brine (300 mL) and was dried over sodium sulfate. Evaporation of the solvent and purification of the residue by flash chromatography yielded S-methyl O-(1-phenyl-2,5,8,11,14-pentaoxahexadecan-16-yl) carbonodithioate (150 g, 91% yield).

Step 2: Preparation of 1,1,1-trifluoro-2,5,8,11,14-pentaoxahexadecan-16-ol

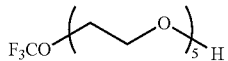

To the suspension of 1,3-dibromo-5,5-dimethylhydantoin (34.0 g, 120.0 mmol) in dichloromethane (300 mL) was added HF-pyridine (40.0 mL, 1600 mmol) at −78° C., and then S-methyl O-(1-phenyl-2,5,8,11,14-pentaoxahexadecan-16-yl) carbonodithioate (15.0 g, 40.0 mmol) added at same temperature. The reaction mixture was stirred at −78° C. further for 1 hour and subsequently warmed to 0° C. and stirred at the same temperature for 2 hours. 150 mL of dichloromethane was added into the reaction mixture. The solution was washed with water (100 mL×3), saturated sodium bisulfite and dried over sodium sulfate. Then the crude was dissolved in MeOH and hydrogenated at room temperature with addition of Pd—C (10%) (1.5 g) under hydrogen atmosphere. The reaction mixture was filtered and evaporated, giving the 1,1,1-trifluoro-2,5,8,11,14-pentaoxahexadecan-16-ol (10.0 g, 86% yield).

Step 3: Preparation of 1,1,1-trifluoro-2,5,8,11,14-pentaoxahexadecan-16-yl methanesulfonate

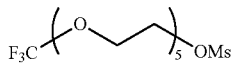

To the mixture of 1,1,1-trifluoro-2,5,8,11,14-pentaoxahexadecan-16-ol (8.0 g, 26.1 mmol), and TEA (4.7 mL, 34.0 mmol) in dichloromethane (150 mL) was added methane sulfonyl chloride (2.2 mL g, 28.7 mmol) at 0° C. The reaction mixture was stirred at room temperature for 1 hour. 150 mL of dichloromethane was added into the reaction mixture. The solution was washed with water (200 mL×3) and was dried over sodium sulfate. Evaporation of the solvent and purification of the residue by flash chromatography yielded 1,1,1-trifluoro-2,5,8,11,14-pentaoxahexadecan-16-yl methanesulfonate (9.0 g, 90% yield).

Step 4: Preparation of N1-(1,1,1-trifluoro-2,5,8,11,14-pentaoxahexadecan-16-yl)benzene-1,4-diamine

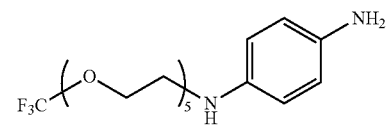

tert-butyl (4-aminophenyl)carbamate (Karra et. al., Bioorganic & Medicinal Chemistry Letters (2013), #23, 3081) (0.9 g, 2.3 mmol) was dissolved in 3 mL of N,N-dimethylformamide and sodium hydride (0.112 g of 60% in mineral oil, 2.81 mmol) was added into the solution. The mixture was stirred for 10 minutes at room temperature and then cooled to 0° C. 1,1,1-trifluoro-2,5,8,11,14-pentaoxahexadecan-16-yl methanesulfonate (0.6 g, 2.6 mmol) was then added under stirring. The reaction mixture was stirred for 18 hours at room temperature and concentrated. The residue was dissolved in ethyl acetate (20 mL) and was washed with water (2×30 mL), brine (30 mL) and was dried over sodium sulfate. Residue obtained after evaporation was dissolved in 3 mL of 4N hydrochloride in 2-propanol. Evaporation of volatiles afforded product as hydrochloride salt The residue partitioned between saturated sodium bicarbonate and dichloromethane, and the organic layer dried on sodium sulfate. Evaporation of solvent and purification of residue by flash chromatography yielded N1-(1,1,1-trifluoro-2,5,8,11,14-pentaoxahexadecan-16-yl)benzene-1,4-diamine (0.4 g, 51% yield).

Step 5: (2S,6R,11R)-3-(cyclopropylmethyl)-6,11-dimethyl-8-((4-((1,1,1-trifluoro-2,5,8,11,14-pentaoxahexadecan-16-yl)amino)phenyl)amino)-3,4,5,6-tetrahydro-2,6-methanobenzo[d]azocin-1(2H)-one (20)

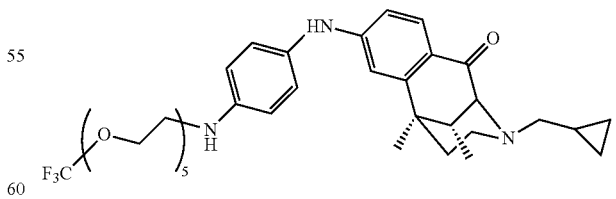

(2S,6R,11R)-3-(cyclopropylmethyl)-6,11-dimethyl-1-oxo-1,2,3,4,5,6-hexahydro-2,6-methanobenzo[d]azocin-8-yl trifluoromethanesulfonate (prepared in a manner similar to Example 7, Step 4) (170 mg, 0.4 mmol), Pd$_2$dba$_3$ (88 mg, 0.09 mmol), BINAP (88 mg, 0.13 mmol), N1-(1,1,1-trifluoro-2,5,8,11,14-pentaoxahexadecan-16-yl)benzene-1,4- diamine (160 mg, 0.44 mmol) and Cs₂CO₃ (470 mg, 1.22 mmol) were suspended in 5 mL of toluene. The mixture was stirred at 110° C. for 1 hour. 20 mL of dichloromethane was added into the reaction mixture. The solution was washed with water (10 mL×3) and was dried over sodium sulfate. Evaporation of the solvent and purification of the residue by flash chromatography yielded (2S,6R,11R)-3-(cyclopropylmethyl)-6,11-dimethyl-8-((4-((1,1,1-trifluoro-2,5,8,11,14-pentaoxahexadecan-16-yl)amino)phenyl)amino)-3,4,5,6-tetrahydro-2,6-methanobenzo[d]azocin-1(2H)-one (20) (110 mg, 40% yield). δ 7.83 (d, 1H), 7.04-7.02 (m, 2H), 6.66-6.59 (m, 3H), 6.59 (d, 1H), 5.85 (bs, 1H), 4.20 (bs, 1H), 4.09 (m, 2H), 3.73-3.71 (m, 4H), 3.68-3.67 (m, 12H), 3.30 (t, 2H), 3.21-3.20 (m, 1H), 2.92-2.90 (m, 1H), 2.74 (dd, 1H), 2.12-1.93 (m, 3H), 1.50-1.48 (m, 1H), 1.33 (s, 3H), 0.91 (d, 3H), 0.89-0.86 (m, 2H), 0.47-0.43 (m, 2H), 0.26-0.24 (m, 1H), 0.07-0.04 (m, 1H). MS (ESI) for $C_{35}H_{48}F_3N_3O_6$: 664 (MH⁺). The free base was dissolved in 4M hydrochloride in 2-propanol. The mixture was concentrated to afford product as hydrochloride salt.

Example 21

Preparation of (2S,6R,11R)-3-(cyclopropylmethyl)-8-((16-(hydroxymethyl)-2,5,8,11,14-pentaoxaheptadecan-17-yl)amino)-6,11-dimethyl-3,4,5,6-tetrahydro-2,6-methanobenzo[d]azocin-1(2H)-one (21)

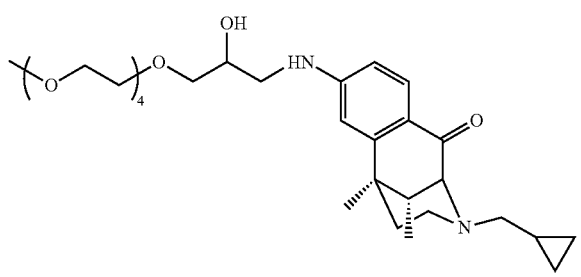

(21)

(2S,6R,11R)-3-(cyclopropylmethyl)-8-((16-(hydroxymethyl)-2,5,8,11,14-pentaoxaheptadecan-17-yl)amino)-6,11-dimethyl-3,4,5,6-tetrahydro-2,6-methanobenzo[d]azocin-1(2H)-one (21) was prepared according to the following steps.

Step 1: Preparation of 16-(benzyloxy)-2,5,8,11,14-pentaoxaheptadecan-17-amine

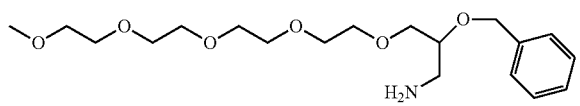 [SMILES: COCCOCCOCCOCCOCC(CN)OCc1ccccc1]

16-(Benzyloxy)-2,5,8,11,14-pentaoxaheptadecan-17-yl methanesulfonate (500 mg, 0.11 mmol) was dissolved in 5 mL of acetonitrile in a sealed tube. 25% aq. ammonia (5 mL) was added and reaction mixture was heated at 80 C for 16 h. Reaction mixture was cooled to room temperature and compound was extracted into EtOAc, dried over anhydrous sodium sulfate, conc. under vacuum to get crude compound. Crude was purified by column chromatography, to afford 16-(benzyloxy)-2,5,8,11,14-pentaoxaheptadecan-17-amine (300 mg, 72.8% yield) as a thick yellow colored liquid.

Step 2: Preparation of (2S,6R,11R)-3-(cyclopropylmethyl)-6,11-dimethyl-8-((16-(phenoxymethyl)-2,5,8,11,14-pentaoxaheptadecan-17-yl)amino)-3,4,5,6-tetrahydro-2,6-methanobenzo[d]azocin-1(2H)-one

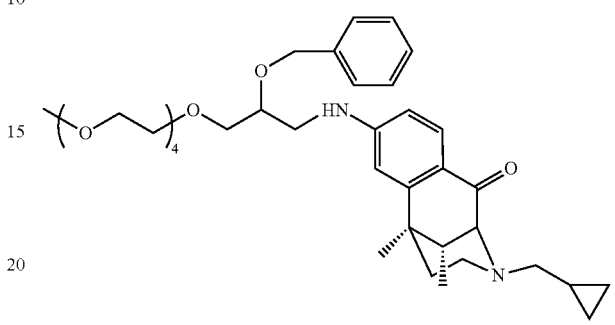

(2S,6R,11R)-3-(cyclopropylmethyl)-6,11-dimethyl-1-oxo-1,2,3,4,5,6-hexahydro-2,6-methanobenzo[d]azocin-8-yltrifluoromethanesulfonate (300 mg, 0.719 mmol) prepared in a manner similar to Example 7, step 4 and 16-(benzyloxy)-2,5,8,11,14-pentaoxaheptadecan-17-amine (293 mg, 0.719 mmol) were dissolved in toluene. BINAP (89.6 mg, 0.144 mmol), Pd₂(dba)₃ (118 mg, 0.0129 mmol) & Cs₂CO₃ (705 mg, 0.215 mmol) were added to the above mixture and heated to 110° C. for 2 h. The mixture was cooled to room temperature and conc. under vacuum. Crude was purified by column chromatography to yield (2S,6R,11R)-3-(cyclopropylmethyl)-6,11-dimethyl-8-((16-(phenoxymethyl)-2,5,8,11,14-pentaoxaheptadecan-17-yl)amino)-3,4,5,6-tetrahydro-2,6-methanobenzo[d]azocin-1(2H)-one (200 mg, 43.6% yield).

Step 3: Preparation of (2S,6R,11R)-3-(cyclopropylmethyl)-8-((16-(hydroxymethyl)-2,5,8,11,14-pentaoxaheptadecan-17-yl)amino)-6,11-dimethyl-3,4,5,6-tetrahydro-2,6-methanobenzo[d]azocin-1(2H)-one

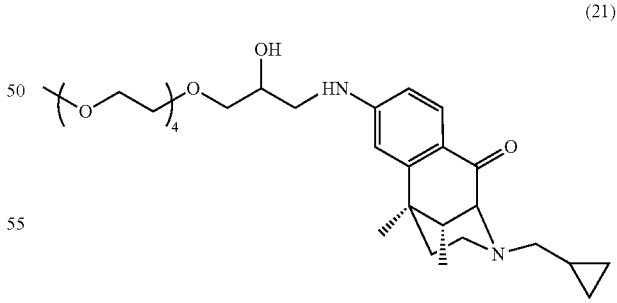

(21)

(2S,6R,11R)-3-(cyclopropylmethyl)-6,11-dimethyl-8-((16-(phenoxymethyl)-2,5,8,11,14-pentaoxaheptadecan-17-yl)amino)-3,4,5,6-tetrahydro-2,6-methanobenzo[d]azocin-1(2H)-one (200 mg). 10% Pd/C (~50% wet) (40 mg) was added to the above mixture and reaction was stirred under hydrogen gas (balloon pressure) for 4 h. Reaction mixture was filtered through celite bed and the bed was washed with methanol. Organic layer was conc. under vacuum to yield (2S,6R,11R)-3-(cyclopropylmethyl)-8-((16-(hydroxymethyl)-2,5,8,11,14-pentaoxaheptadecan-17-yl)amino)-6,11-dimethyl-3,4,5,6-tetrahydro-2,6-methanobenzo[d]azocin-1(2H)-one (21) (125 mg, 81.7% yield). $^1$H NMR (500 MHz, CDCl$_3$): δ7.9 (m, 1H), 7.6 (m, 1H), 7.4 (s, 1H), 4.05 (m, 1H), 3.9 (m, 2H), 3.6-3.7 (m, 16H), 3.55 (s, 2H), 3.37 (s, 3H), 2.85 (m, 1H), 2.92-2.95 (m, 1H), 2.63-2.67 (m, 1H), 1.93-2.22 (m, 4H), 1.45 (s, 3H), 1.25 (m, 1H), 0.87-0.88 (m, 4H), 0.46-0.53 (m, 2H), 0.26 (m, 1H), 0.04-0.07 (m, 1H); MS (ESI) for C$_{30}$H$_{46}$N$_2$O$_7$: 549.3317 (MH$^+$). The free base was dissolved in 4M hydrochloride in 2-propanol. The mixture was concentrated to afford product as hydrochloride salt.

Example 22

Preparation of (7S,11R,12R)-2-(2,5,8,11,14-pentaoxahexadecan-16-ylamino)-8-(cyclopropylmethyl)-11,12-dimethyl-8,9,10,11-tetrahydro-7,11-methanothiazolo[5',4':3,4]benzo[1,2-d]azocin-6(7H)-one (22)

(22)

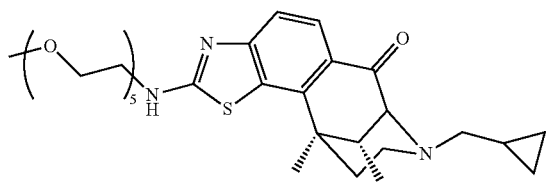

(7S,11R,12R)-2-(2,5,8,11,14-pentaoxahexadecan-16-ylamino)-8-(cyclopropylmethyl)-11,12-dimethyl-8,9,10,11-tetrahydro-7,11-methanothiazolo[5',4':3,4]benzo[1,2-d]azocin-6(7H)-one (22) was prepared according to the following steps.

Step 1: Preparation of 1-((2S,6R,11R)-3-(cyclopropylmethyl)-6,11-dimethyl-1-oxo-1,2,3,4,5,6-hexahydro-2,6-methanobenzo[d]azocin-8-yl)-3-(2,5,8,11,14-pentaoxahexadecan-16-yl)thiourea

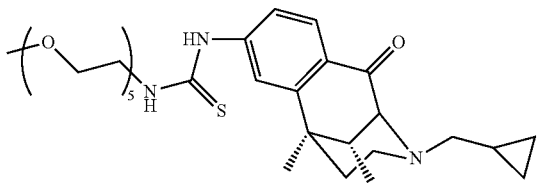

(2S,6R,11R)-8-amino-3-(cyclopropylmethyl)-6,11-dimethyl-3,4,5,6-tetrahydro-2,6-methanobenzo[d]azocin-1(2H)-one (prepared in a manner similar to Example 15, Step 3) (60 mg, 0.21 mmol), and O,O-di(pyridin-2-yl) carbonothioate (49 mg, 0.22 mmol) were dissolved in 2 mL of tetrahydrofuran. The mixture was stirred for 2 hours at 65° C. and then cooled to room temperature. mPEG$_5$-NH$_2$ (53 g, 0.22 mmol) was added into the solution. The reaction mixture was stirred for 1 hour and then was concentrated. Residue was purified by flash chromatography to yield 1-((2S,6R,11R)-3-(cyclopropylmethyl)-6,11-dimethyl-1-oxo-1,2,3,4,5,6-hexahydro-2,6-methanobenzo[d]azocin-8-yl)-3-(2,5,8,11,14-pentaoxahexadecan-16-yl)thiourea (70 mg, 57% yield)

Step 2: Preparation of (7S,11R,12R)-2-(2,5,8,11,14-pentaoxahexadecan-16-ylamino)-8-(cyclopropylmethyl)-11,12-dimethyl-8,9,10,11-tetrahydro-7,11-methanothiazolo[5',4':3,4]benzo[1,2-d]azocin-6(7H)-one (22)

(22)

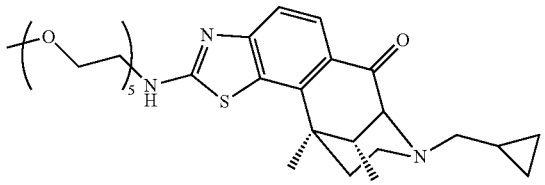

1-((2S,6R,11R)-3-(cyclopropylmethyl)-6,11-dimethyl-1-oxo-1,2,3,4,5,6-hexahydro-2,6-methanobenzo[d]azocin-8-yl)-3-(2,5,8,11,14-pentaoxahexadecan-16-yl)thiourea (120 mg, 0.2 mmol) was dissolved in 5 mL of dichloromethane and benzyltrimethyl ammonium tribromide (80 mg, 0.2 mmol) was added into the solution. The reaction mixture was stirred at room temperature for 18 hours. 20 mL of dichloromethane was added into the reaction mixture. The solution was washed with 5% aqueous NaHCO$_3$ (30 mL), water (10 mL×3) and was dried over sodium sulfate. Evaporation of the solvent and purification of the residue by flash chromatography yielded (7S,11R,12R)-2-(2,5,8,11,14-pentaoxahexadecan-16-ylamino)-8-(cyclopropylmethyl)-11,12-dimethyl-8,9,10,11-tetrahydro-7,11-methanothiazolo[5',4':3,4]benzo[1,2-d]azocin-6(7H)-one (22) (55 mg, 46% yield). $^1$H NMR (500 MHz, CDCl$_3$): δ 8.02 (d, 1H), 7.43 (d, 1H), 6.43 (bs, 1H), 3.75-3.63 (m, 19H), 3.55-3.53 (m, 2H), 3.36 (s, 3H), 3.27 (d, 1H), 2.92-2.89 (m, 1H), 2.71 (dd, 1H), 2.16-2.13 (m, 1H), 2.01-1.82 (m, 2H), 1.63 (s, 3H), 0.96 (d, 3H), 0.89-0.86 (m, 2H), 0.48-0.45 (m, 2H), 0.26-0.23 (m, 1H), 0.06-0.02 (m, 1H). MS (ESI) for C$_{30}$H$_{45}$N$_3$O$_6$S: 576 (MH$^+$). The free base was dissolved in 1 mL of 4M hydrochloride in 2-propanol. The mixture was concentrated to afford product as hydrochloride salt.

Example 23

Preparation of (2S,6R,11R)-3-(Cyclopropylmethyl)-8-((1-hydroxy-2-methylpropan-2-yl)amino)-6,11-dimethyl-3,4,5,6-tetrahydro-2,6-methanobenzo[d]azocin-1(2H)-one (23)

(23)

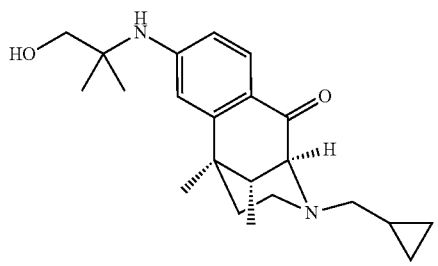

(2S,6R,11R)-3-(Cyclopropylmethyl)-8-((1-hydroxy-2-methylpropan-2-yl)amino)-6,11-dimethyl-3,4,5,6-tetrahydro-2,6-methanobenzo[d]azocin-1(2H)-one (23) was prepared according to the following steps

Step 1: Preparation of tert-butyl (1-hydroxy-2-methylpropan-2-yl)carbamate

2-Amino-2-methyl-1-propanol (5 g, 56.1 mmol), (Boc)$_2$O (13.46 g, 61.7 mmol) and triethyl amine (6.24 g, 61.7 mmol) were dissolved in 50 mL of dichloromethane. The reaction mixture was stirred for 4 h at 22 to 25° C. Above mixture was washed with water (25 mL×2), dried over anhydrous sodium sulfate and concentrated under vacuum to get tert-butyl (1-hydroxy-2-methylpropan-2-yl)carbamate (10.3 g, 97% yield).

Step 2: Preparation of tert-butyl (1-(benzyloxy)-2-methylpropan-2-yl)carbamate

tert-Butyl (1-hydroxy-2-methylpropan-2-yl)carbamate (2) (2 g, 10.57 mmol), potassium hydroxide (1.10 g, 19.55 mmol), and benzyl bromide (3.34 g, 19.55 mmol) were dissolved in 20 mL of DMF. The mixture was stirred for 2 h and concentrated under vacuum. Crude was purified by column chromatography yielded tert-butyl (1-(benzyloxy)-2-methylpropan-2-yl)carbamate (2.65 g, 90% yield).

Step 3: Preparation of 1-(benzyloxy)-2-methylpropan-2-amine

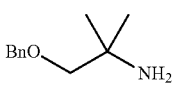

tert-Butyl (1-(benzyloxy)-2-methylpropan-2-yl)carbamate (2 g, 7.16 mmol) was dissolved in 25 mL of 4M HCl in IPA. The mixture was stirred for 1 h and concentrated under vacuum. The residue was dissolved in 50 mL of water and pH was adjusted to 9.0 using 1M aq. NaOH. The compound was extracted into ethyl acetate, dried over anhydrous sodium sulfate, concentrated under vacuum to yield 1-(benzyloxy)-2-methylpropan-2-amine as brown gum (0.90 g, 70% yield).

Step 4: Preparation of (2S,6R,11R)-8-((1-(benzyloxy)-2-methylpropan-2-yl)amino)-3-(cyclopropylmethyl)-6,11-dimethyl-3,4,5,6-tetrahydro-2,6-methanobenzo[d]azocin-1(2H)-one

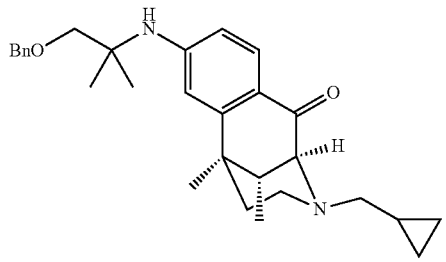 [SMILES: C[C@H]1[C@H]2C(=O)c3ccc(NC(C)(C)COCc4ccccc4)cc3[C@]1(C)CCN2CC1CC1]

(2S,6R,11R)-3-(Cyclopropylmethyl)-6,11-dimethyl-1-oxo-1,2,3,4,5,6-hexahydro-2,6-methanobenzo[d]azocin-8-yl trifluoromethanesulfonate (0.450 mg, 1.078 mmol) and 1-(benzyloxy)-2-methylpropan-2-amine (0.193 g, 1.078 mmol) were dissolved in toluene. BINAP (0.199 g, 0.32 mmol), Pd$_2$dba$_3$ (0.198 g, 0.216 mmol) and Cs$_2$CO$_3$ (0.490 g, 1.51 mmol) were added to the above mixture and heated to 110° C. for 3 h. The mixture was cooled to room temperature and concentrated under vacuum. Crude was purified by flash chromatography to yield (2S,6R,11R)-8-((1-(benzyloxy)-2-methylpropan-2-yl)amino)-3-(cyclopropylmethyl)-6,11-dimethyl-3,4,5,6-tetrahydro-2,6-methanobenzo[d]azocin-1(2H)-one (200 mg, 42% yield).

Step 5: Preparation of (2S,6R,11R)-3-(cyclopropylmethyl)-8-((1-hydroxy-2-methylpropan-2-yl)amino)-6,11-dimethyl-3,4,5,6-tetrahydro-2,6-methanobenzo[d]azocin-1(2H)-one (23)

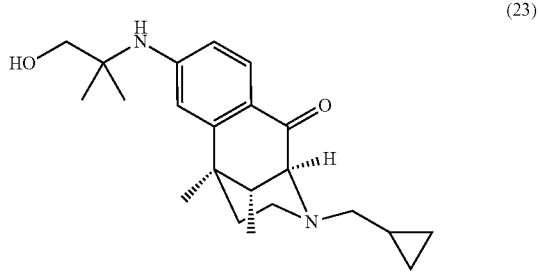 [SMILES: C[C@H]1[C@H]2C(=O)c3ccc(NC(C)(C)CO)cc3[C@]1(C)CCN2CC1CC1]

(23)

(2S,6R,11R)-8-((1-(benzyloxy)-2-methylpropan-2-yl)amino)-3-(cyclopropylmethyl)-6,11-dimethyl-3,4,5,6-tetrahydro-2,6-methanobenzo[d]azocin-1(2H)-one (190 mg, 0.425 mmol) was dissolved in 10 mL of methanol. 10% Pd/C (~50% wet) (20 mg) was added to the above mixture and the reaction was performed under hydrogen balloon pressure for 4 h. Reaction mixture was filtered through a celite bed and washed with methanol. Evaporation of solvent under vacuum yielded (2S,6R,11R)-3-(cyclopropylmethyl)-8-((1-hydroxy-2-methylpropan-2-yl)amino)-6,11-dimethyl-3,4,5,6-tetrahydro-2,6-methanobenzo[d]azocin-1(2H)-one (160 mg, 99% yield). $^1$H NMR (500 MHz, DMSO-d$_6$): δ 11.36 (bs, 1H), 7.71 (d, 1H), 6.69-6.73 (m, 3H), 3.86 (bs, 1H), 3.4-3.43 (m, 2H), 3.17 (s, 1H), 3.06-3.16 (m, 1H), 2.6-2.67 (m, 3H), 2.24-2.31 (m, 1H), 1.63-1.66 (m, 1H), 1.37 (m, 3H), 1.23-1.29 (m, 10H), 0.81-0.87 (m, 3H), 0.6-0.63 (m, 2H), 0.47-0.49 (m, 2H); MS (ESI) for $C_{22}H_{32}N_2O_2$: 357.2401 (MH$^+$). The free base was dissolved in 4M hydrochloride in 2-propanol. The mixture was concentrated to afford product as hydrochloride salt.

Example 24

Preparation of (2S,6R,11R)-3-(cyclopropylmethyl)-8-((1,3-dihydroxypropan-2-yl)amino)-6,11-dimethyl-3,4,5,6-tetrahydro-2,6-methanobenzo[d]azocin-1(2H)-one (24)

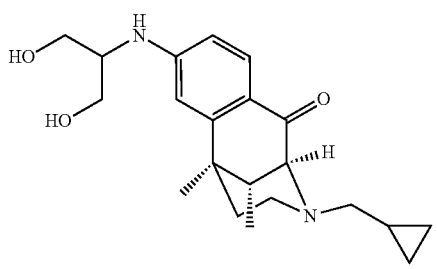

(24)

(2S,6R,11R)-3-(cyclopropylmethyl)-8-((1,3-dihydroxypropan-2-yl)amino)-6,11-dimethyl-3,4,5,6-tetrahydro-2,6-methanobenzo[d]azocin-1(2H)-one (24) was prepared according to the following steps.

Step 1: Preparation of tert-butyl (1,3-dihydroxypropan-2-yl)carbamate

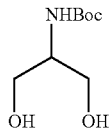

Serinol (2.00 g, 21.96 mmol) and (Boc)$_2$O (4.80 g, 21.96 mmol) was dissolved in 20 mL of dichloromethane. The reaction mixture was stirred for 4 h at 22 to 25° C. The above mixture was washed with water (25 mL×2), dried over anhydrous sodium sulfate and concentrated under vacuum to yield tert-butyl (1,3-dihydroxypropan-2-yl)carbamate (4.1 g, 97% yield).

Step 2: Preparation of tert-butyl (1,3-bis(benzyloxy)propan-2-yl)carbamate

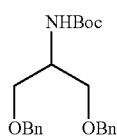

tert-Butyl (1,3-dihydroxypropan-2-yl)carbamate (3.7 g, 19.35 mmol), potassium hydroxide (4.0 g, 71.59 mmol), and benzyl bromide (12.24 g, 71.59 mmol) were dissolved in 50 mL of DMF. The mixture was stirred for 2 h and concentrated under vacuum. The crude product was purified using column chromatography to yield tert-butyl (1,3-bis(benzyloxy)propan-2-yl)carbamate (3.25 g, 45% yield).

Step 3: Preparation of 1,3-bis(benzyloxy)propan-2-amine

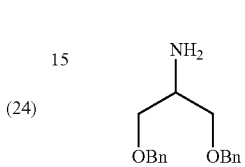

tert-butyl (1,3-bis(benzyloxy)propan-2-yl)carbamate (3.00 g, 8.076 mmol) was dissolved in 25 mL of 4M HCl in IPA. The mixture was stirred for 1 hour and concentrated under vacuum. The residue was dissolved in 50 mL of water and pH was adjusted to 9.0 using 1M aq. NaOH. The compound was extracted into ethyl acetate, dried over anhydrous sodium sulfate, and concentrated under vacuum to yield 1,3-bis(benzyloxy)propan-2-amine as a brown gum (2.00 g, 91% yield).

Step 4: Preparation of (2S,6R,11R)-8-((1,3-bis(benzyloxy)propan-2-yl)amino)-3-(cyclopropylmethyl)-6,11-dimethyl-3,4,5,6-tetrahydro-2,6-methanobenzo[d]azocin-1(2H)-one

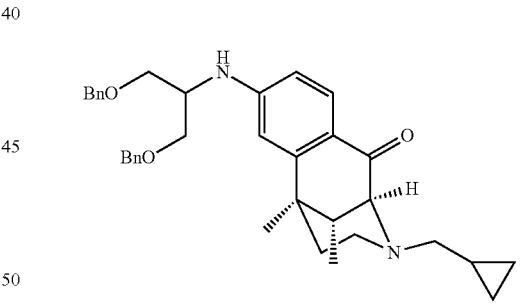

(2S,6R,11R)-3-(Cyclopropylmethyl)-6,11-dimethyl-1-oxo-1,2,3,4,5,6-hexahydro-2,6-methanobenzo[d]azocin-8-yl trifluoromethanesulfonate (0.450 mg, 1.078 mmol) and 1,3-bis(benzyloxy)propan-2-amine (0.351 g, 1.29 mmol) were dissolved in toluene. BINAP (0.199 g, 0.32 mmol), Pd$_2$dba$_3$ (0.198 g, 0.216 mmol) and Cs$_2$CO$_3$ (0.490 g, 1.51 mmol) were added to the above mixture and heated to 110° C. for 3 hours. The mixture was cooled to room temperature and concentrated under vacuum. Crude on purification using flash chromatography yielded (2S,6R,11R)-8-((1,3-bis(benzyloxy)propan-2-yl)amino)-3-(cyclopropylmethyl)-6,11-dimethyl-3,4,5,6-tetrahydro-2,6-methanobenzo[d]azocin-1(2H)-one (0.545 g, 94% yield).

Preparation of (2S,6R,11R)-3-(cyclopropylmethyl)-8-((1,3-dihydroxypropan-2-yl)amino)-6,11-dimethyl-3,4,5,6-tetrahydro-2,6-methanobenzo[d]azocin-1(2H)-one (24)

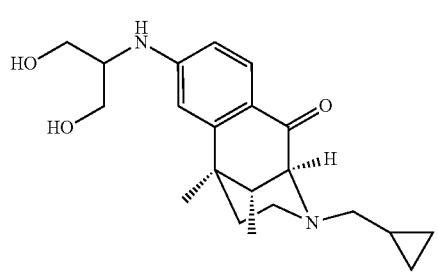

(24)

(2S,6R,11R)-8-((1,3-bis(benzyloxy)propan-2-yl)amino)-3-(cyclopropylmethyl)-6,11-dimethyl-3,4,5,6-tetrahydro-2,6-methanobenzo[d]azocin-1(2H)-one (0.545 g, 1.01 mmol) was dissolved in 10 mL of methanol. 10% Pd/C (~50% wet) (50 mg) was added to the above mixture and reaction was performed under hydrogen balloon pressure for 4 hours. The reaction mixture was filter through a celite bed and washed with methanol. Concentration of the organic layer under vacuum yielded (2S,6R,11R)-3-(cyclopropylmethyl)-8-((1,3-dihydroxypropan-2-yl)amino)-6,11-dimethyl-3,4,5,6-tetrahydro-2,6-methanobenzo[d]azocin-1(2H)-one (0.350 g, 97% yield). $^1$H NMR (500 MHz, DMSO-$d_6$): δ 10.99 (bs, 1H), 7.72 (d, 1H), 6.9-6.96 (m, 1H), 6.59-6.67 (m, 2H), 3.87 (bs, 1H), 3.41-3.52 (m, 10H), 3.17 (s, 1H), 3.08-3.12 (m, 1H), 2.57-2.68 (m, 3H), 2.19-2.25 (m, 1H), 1.65-1.67 (m, 1H), 1.38 (m, 3H), 1.22-1.29 (m, 3H), 0.81-0.86 (m, 3H), 0.6-0.62 (m, 2H), 0.47-0.48 (m, 2H); MS (ESI) for $C_{22}H_{32}N_2O_2$: 359.2196 (MH$^+$). The free base was dissolved in 4M hydrochloride in 2-propanol. The mixture was concentrated to afford product as hydrochloride salt.

Example 25

Preparation of (1R,2S,6R,11R)-1-(2,5,8,11,14-pentaoxahexadecan-16-yloxy)-3-(cyclopropylmethyl)-6,11-dimethyl-1,2,3,4,5,6-hexahydro-2,6-methanobenzo[d]azocin-8-ol (25)

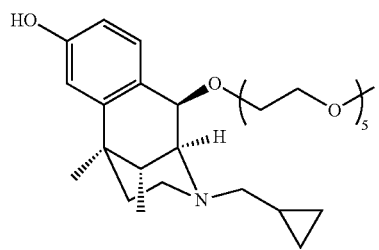

(25)

(1R,2S,6R,11R)-1-(2,5,8,11,14-Pentaoxahexadecan-16-yloxy)-3-(cyclopropylmethyl)-6,11-dimethyl-1,2,3,4,5,6-hexahydro-2,6-methanobenzo[d]azocin-8-ol (25) was prepared according to the following steps.

Step 1: Preparation of (2S,6R,11R)-8-(benzyloxy)-3-(cyclopropylmethyl)-6,11-dimethyl-3,4,5,6-tetrahydro-2,6-methanobenzo[d]azocin-1(2H)-one

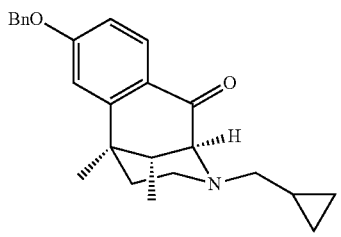 [SMILES: C[C@H]1[C@H]2C(=O)c3ccc(OCc4ccccc4)cc3[C@]1(C)CCN2CC1CC1]

(2S,6R,11R)-3-(cyclopropylmethyl)-8-hydroxy-6,11-dimethyl-3,4,5,6-tetrahydro-2,6-methanobenzo[d]azocin-1(2H)-one (1.0 g, 3.5 mmol) was dissolved in 20 mL of acetonitrile and cesium carbonate (4.5 g, 14.0 mmol) was added into the solution. The mixture was stirred for 10 minutes at 60° C. Benzyl bromide (0.4 mL, 3.5 mmol) was then added under stirring. The reaction mixture stirred for 1 hour at 60° C., filtered and concentrated. The residue was dissolved in ethyl acetate (60 mL) and was washed with water (2×50 mL), dried over anhydrous sodium sulfate. Evaporation of the solvent and purification of residue by flash chromatography yielded (2S,6R,11R)-8-(benzyloxy)-3-(cyclopropylmethyl)-6,11-dimethyl-3,4,5,6-tetrahydro-2,6-methanobenzo[d]azocin-1(2H)-one (1.2 g, 91% yield).

Step 2: Preparation of (1R,2S,6R,11R)-8-(benzyloxy)-3-(cyclopropylmethyl)-6,11-dimethyl-1,2,3,4,5,6-hexahydro-2,6-methanobenzo[d]azocin-1-ol

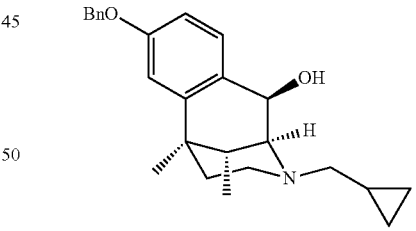

To the solution of (2S,6R,11R)-8-(benzyloxy)-3-(cyclopropylmethyl)-6,11-dimethyl-3,4,5,6-tetrahydro-2,6-methanobenzo[d]azocin-1(2H)-one (1.0 g, 2.6 mmol) in tetrahydrofuran (30 mL) was added 1M lithium aluminium hydride solution in THF (2.6 mL, 2.6 mmol) at 0° C. The reaction mixture was stirred at room temperature for 18 hours. 10 mL of ethyl acetate was added into the reaction mixture. The suspension was passed through plug of celite. Evaporation of the solvent and purification of the residue by flash chromatography yielded (1R,2S,6R,11R)-8-(benzyloxy)-3-(cyclopropylmethyl)-6,11-dimethyl-1,2,3,4,5,6-hexahydro-2,6-methanobenzo[d]azocin-1-ol (0.7 g, 69% yield).

Step 3: Preparation of (1R,2S,6R,11R)-1-(2,5,8,11,14-pentaoxahexadecan-16-yloxy)-8-(benzyloxy)-3-(cyclopropylmethyl)-6,11-dimethyl-1,2,3,4,5,6-hexahydro-2,6-methanobenzo[d]azocine

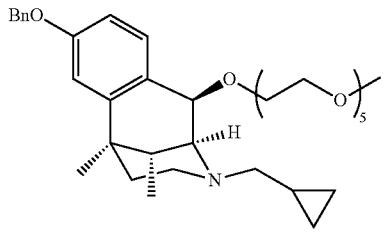

(1R,2S,6R,11R)-8-(Benzyloxy)-3-(cyclopropylmethyl)-6,11-dimethyl-1,2,3,4,5,6-hexahydro-2,6-methanobenzo[d]azocin-1-ol (0.7 g, 1.8 mmol) was dissolved in 3 mL of N,N-dimethylformamide and sodium hydride (0.148 g of 60% in mineral oil, 3.7 mmol) was added into the solution. The mixture was stirred for 10 minutes at room temperature and then heated to 70° C. mPEG$_5$-OMs (0.86 g, 2.6 mmol) was then added under stirring. The reaction mixture was stirred 70° C. for 18 h. Reaction mixture was dissolved in ethyl acetate (20 mL) and was washed with water (2×50 mL), brine (30 mL) and was dried over any sodium sulfate. Evaporation of solvent and purification of residue by flash chromatography yielded of (1R,2S,6R,11R)-1-(2,5,8,11,14-pentaoxahexadecan-16-yloxy)-8-(benzyloxy)-3-(cyclopropylmethyl)-6,11-dimethyl-1,2,3,4,5,6-hexahydro-2,6-methanobenzo[d]azocine (0.4 g, 35% yield).

Step 4: Preparation of (1R,2S,6R,11R)-1-(2,5,8,11,14-Pentaoxahexadecan-16-yloxy)-3-(cyclopropylmethyl)-6,11-dimethyl-1,2,3,4,5,6-hexahydro-2,6-methanobenzo[d]azocin-8-ol (25)

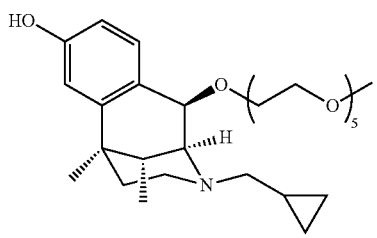

(25)

(1R,2S,6R,11R)-1-(2,5,8,11,14-pentaoxahexadecan-16-yloxy)-8-(benzyloxy)-3-(cyclopropylmethyl)-6,11-dimethyl-1,2,3,4,5,6-hexahydro-2,6-methanobenzo[d]azocine (0.400 g, 0.4 mmol) was dissolved in MeOH and hydrogenated at room temperature with addition of Pd—C (10%) (0.100 g) under hydrogen atmosphere. The reaction mixture filtered and evaporated and the purification of residue by flash chromatography yielded (1R,2S,6R,11R)-1-(2,5,8,11,14-Pentaoxahexadecan-16-yloxy)-3-(cyclopropylmethyl)-6,11-dimethyl-1,2,3,4,5,6-hexahydro-2,6-methanobenzo[d]azocin-8-ol (0.170 g, 49% yield). $^1$H NMR (500 MHz, CDCl$_3$): δ 7.47 (d, 1H), 6.74 (dd, 1H), 6.64 (d, 1H), 5.85 (bs, 1H), 4.54 (d, 1H), 3.94-3.95 (m, 1H), 3.57-3.74 (m, 19H), 3.39 (s, 3H), 3.17 (t, 1H), 2.96 (dd, 1H), 2.81 (dd, 1H), 2.63 (dd, 1H), 2.48 (dt, 1H), 2.04-2.10 (m, 1H), 1.78 (dt, 1H), 1.30 (s, 3H), 1.13-1.15 (m, 1H), 0.87 (d, 3H), 0.79-0.81 (m, 1H), 0.47-0.52 (m, 1H), 0.36-0.42 (m, 1H), 0.06-0.12 (m, 2H). MS (ESI) for C$_{29}$H$_{47}$NO$_7$: 522 (MH$^+$). The free base (170 mg) was dissolved in 2 mL of 4N hydrochloride in 2-propanol. The mixture was concentrated to afford product as hydrochloride salt.

Example 26

Preparation of (2S,6R,11R)-7-(2,5,8,11,14-pentaoxahexadecan-16-ylamino)-3-(cyclopropylmethyl)-8-hydroxy-6,11-dimethyl-3,4,5,6-tetrahydro-2,6-methanobenzo[d]azocin-1(2H)-one, hydrochloride Salt (26)

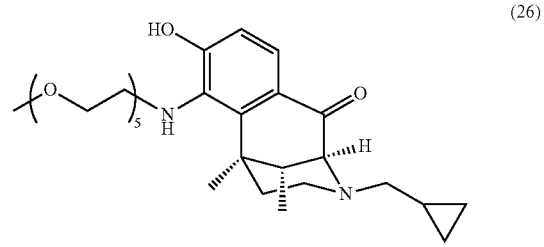

(26)

(2S,6R,11R)-7-(2,5,8,11,14-pentaoxahexadecan-16-ylamino)-3-(cyclopropylmethyl)-8-hydroxy-6,11-dimethyl-3,4,5,6-tetrahydro-2,6-methanobenzo[d]azocin-1(2H)-one, hydrochloride salt (26) was prepared according to the following steps.

Step 1: Preparation of (2S,6R,11R)-8-(benzyloxy)-7-bromo-3-(cyclopropylmethyl)-6,11-dimethyl-3,4,5,6-tetrahydro-2,6-methanobenzo[d]azocin-1(2H)-one

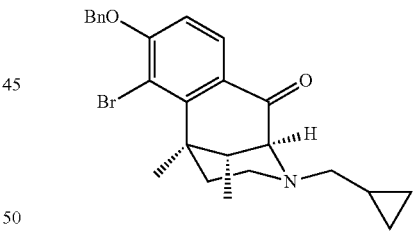

(2S,6R,11R)-7-bromo-3-(cyclopropylmethyl)-8-hydroxy-6,11-dimethyl-3,4,5,6-tetrahydro-2,6-methanobenzo[d]azocin-1(2H)-one (0.450 g, 1.2 mmol) was dissolved in 10 mL of acetonitrile and cesium carbonate (0.80 g, 2.4 mmol) was added into the solution. The mixture was stirred for 10 minutes at 60° C. Benzyl bromide (0.15 mL, 1.2 mmol) was then added under stirring. The reaction mixture stirred for 1 hour at 60° C., filtered and concentrated. The residue was dissolved in ethyl acetate (20 mL) and was washed with water (2×20 mL), dried over sodium sulfate. Evaporation of the solvent and purification of the residue by flash chromatography yielded (2S,6R,11R)-8-(benzyloxy)-7-bromo-3-(cyclopropylmethyl)-6,11-dimethyl-3,4,5,6-tetrahydro-2,6-methanobenzo[d]azocin-1(2H)-one (0.450 g, 80% yield).

Step 2: Preparation of (2S,6R,11R)-7-(2,5,8,11,14-pentaoxahexadecan-16-ylamino)-8-(benzyloxy)-3-(cyclopropylmethyl)-6,11-dimethyl-3,4,5,6-tetrahydro-2,6-methanobenzo[d]azocin-1(2H)-one

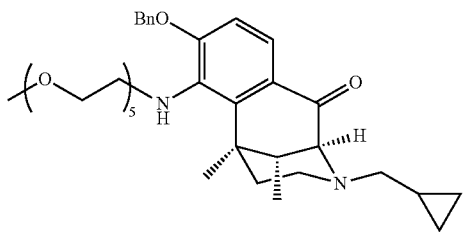

(2S,6R,11R)-8-(benzyloxy)-7-bromo-3-(cyclopropylmethyl)-6,11-dimethyl-3,4,5,6-tetrahydro-2,6-methanobenzo[d]azocin-1(2H)-one (0.370 g, 0.8 mmol), BrettPHOS palladacycle (0.065 g, 0.08 mmol), BrettPHOS (0.044 g, 0.08 mmol), 2,5,8,11,14-pentaoxahexadecan-16-amine (0.37 g, 1.4 mmol) and 2M Sodium ter-butoxide solution in THF (1.2 mL, 2.4 mmol) were suspended in 3 mL of toluene. The mixture was stirred at 90° C. for 4 hours. 20 mL of ethyl acetate was added into the reaction mixture. The solution was washed with water (2×10 mL) and was dried over sodium sulfate. Evaporation of the solvent and purification of the residue by flash chromatography yielded (2S,6R,11R)-7-(2,5,8,11,14-pentaoxahexadecan-16-ylamino)-8-(benzyloxy)-3-(cyclopropylmethyl)-6,11-dimethyl-3,4,5,6-tetrahydro-2,6-methanobenzo[d]azocin-1(2H)-one (0.200 g, 40% yield).

Step 3: Preparation of (2S,6R,11R)-7-(2,5,8,11,14-pentaoxahexadecan-16-ylamino)-3-(cyclopropylmethyl)-8-hydroxy-6,11-dimethyl-3,4,5,6-tetrahydro-2,6-methanobenzo[d]azocin-1(2H)-one, hydrochloride salt (26)

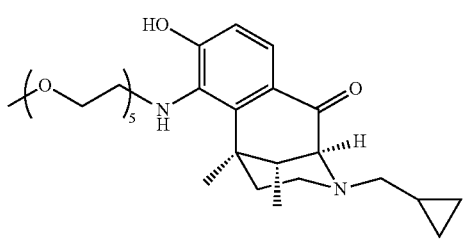

(26)

(2S,6R,11R)-7-(2,5,8,11,14-pentaoxahexadecan-16-ylamino)-8-(benzyloxy)-3-(cyclopropylmethyl)-6,11-dimethyl-3,4,5,6-tetrahydro-2,6-methanobenzo[d]azocin-1(2H)-one (0.220 g, 0.35 mmol) was dissolved in MeOH and hydrogenated at room temperature with addition of Pd—C (10%) (~50% wet) (0.050 g) under hydrogen atmosphere. The reaction mixture filtered and evaporated, and the purification of residue by flash chromatography yielded (2S,6R,11R)-7-(2,5,8,11,14-pentaoxahexadecan-16-ylamino)-3-(cyclopropylmethyl)-8-hydroxy-6,11-dimethyl-3,4,5,6-tetrahydro-2,6-methanobenzo[d]azocin-1(2H)-one (0.105 g, 55% yield). $^1$H NMR (500 MHz, CDCl$_3$): δ 8.3-8.7 (bs, 1H), 7.87 (d, 1H), 6.89 (d, 1H), 3.72-3.78 (m, 4H), 3.62-3.69 (m, 14H), 3.53-3.57 (m, 2H), 3.37 (s, 3H), 3.21 (d, 1H), 3.08-3.12 (m, 2H), 2.97-2.98 (m, 1H), 2.91-2.94 (m, 1H), 2.71 (dd, 1H), 1.92-2.03 (m, 2H), 1.73-1.75 (m, 1H), 1.65 (s, 3H), 0.93 (d, 3H), 0.83-0.90 (m, 1H), 0.43-0.49 (m, 2H), 0.22-0.24 (m, 1H), 0.03-0.06 (m, 1H). MS (ESI) for C$_{29}$H$_{46}$N$_2$O$_7$: 535 (MH$^+$). The free base (100 mg) was dissolved in 2 mL of 4N hydrochloride in 2-propanol. The mixture was concentrated to afford product as hydrochloride salt.

Example 27

Preparation of (2S,6R,11R)-3-(cyclopropylmethyl)-8-((1-(2-methoxyethyl)piperidin-4-yl)amino)-6,11-dimethyl-3,4,5,6-tetrahydro-2,6-methanobenzo[d]azocin-1(2H)-one (27)

(27)

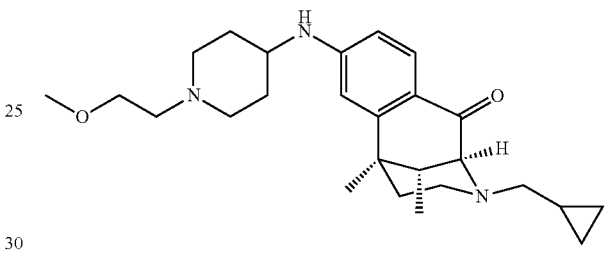

(2S,6R,11R)-3-(cyclopropylmethyl)-8-((1-(2-methoxyethyl)piperidin-4-yl)amino)-6,11-dimethyl-3,4,5,6-tetrahydro-2,6-methanobenzo[d]azocin-1(2H)-one (27) was prepared according to the following steps.

Step 1: Preparation of 1-(2-methoxyethyl)piperidin-4-amine

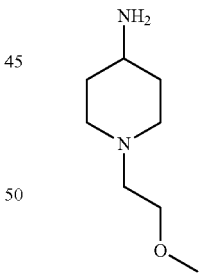

4-amino piperidine (2 g. 19.96 mmol) and anhydrous sodium carbonate (5.29 g, 49.9 mmol) was dissolved in 25 mL of methyl isobutyl ketone. The heterogeneous reaction mass was heated to reflux, and maintained for 4 h. 2-Methoxyethyl methanesulfonate (2.77 g, 17.96 mmol) was added to the above mixture and stirred for 16 h at 22 to 25° C. The reaction mass was filtered and 25 mL of 1N aq.HCl was added and stirred for another 1 h. The aqueous phase was separated, and pH was adjusted to 11.0 using 1N aq. NaOH. Compound was extracted into DCM, dried over anhydrous sodium sulfate and conc under vacuum to get 1-(2-methoxyethyl)piperidin-4-amine ((300 mg, 9.5% yield)

Step 2: Preparation of (2S,6R,11R)-3-(cyclopropylmethyl)-8-((1-(2-methoxyethyl)piperidin-4-yl)amino)-6,11-dimethyl-3,4,5,6-tetrahydro-2,6-methanobenzo[d]azocin-1(2H)-one (27)

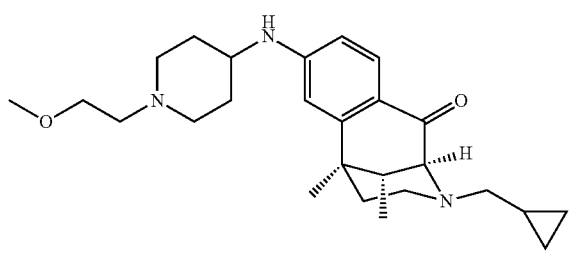

(27)

(2S,6R,11R)-3-(cyclopropylmethyl)-6,11-dimethyl-1-oxo-1,2,3,4,5,6-hexahydro-2,6-methanobenzo[d]azocin-8-yl trifluoromethanesulfonate (0.350 g, 0.8384 mmol) and 1-(2-methoxyethyl)piperidin-4-amine (0.159 g, 1.006 mmol) were dissolved in toluene. BINAP (0.156 g, 0.2515 mmol), $Pd_2dba_3$ (0.153 g, 0.1676 mmol) & $Cs_2CO_3$ (0.39 g, 1.1737 mmol) were added to the above mixture and heated to 110° C. for 2 h. The mixture was cooled to room temperature and concentrated under vacuum. Crude was purified by silica gel column chromatography to get pure (2S,6R,11R)-3-(cyclopropylmethyl)-8-((1-(2-methoxyethyl)piperidin-4-yl)amino)-6,11-dimethyl-3,4,5,6-tetrahydro-2,6-methanobenzo[d]azocin-1(2H)-one (0.170 g, 48% yield). $^1$H NMR (500 MHz, $CDCl_3$): δ 7.8 (d, 1H), 7.68-7.70 (m, 2H), 3.5 (t, 2H), 3.35 (s, 3H), 3.15 (d, 1H), 2.9 (m, 2H), 2.78-2.81 (m, 1H), 2.65 (m, 2H), 2.55 (t, 2H), 2.45-2.48 (m, 1H), 2.05-2.06 (m, 2H), 1.82-1.96 (m, 3H), 1.41-1.44 (m, 3H), 1.37 (s, 3H), 1.1-1.3 (m, 2H), 0.9 (m, 1H), 0.77-0.83 (m, 3H), 0.39-0.46 (m, 2H), 0.18-0.21 (m, 1H), 0.01-0.02 (m, 2H); MS (ESI) for $C_{26}H_{39}N_3O_2$: 426.3116 (MH$^+$). The free base was dissolved in 2 mL of 4N hydrochloride in 2-propanol. The mixture was concentrated to afford product as hydrochloride salt.

Example 28

Preparation of (2S,6R,11R)-3-(cyclopropylmethyl)-8-(4-(2-(2-(2-methoxyethoxy)ethoxy)ethyl)piperazin-1-yl)-6,11-dimethyl-3,4,5,6-tetrahydro-2,6-methanobenzo[d]azocin-1(2H)-one (1)

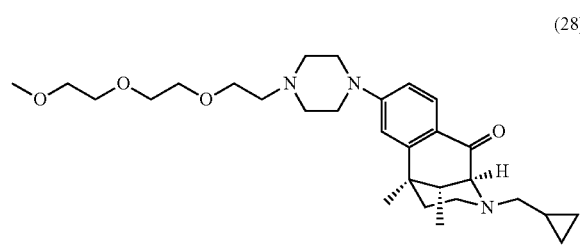 [SMILES: COCCOCCOCCN1CCN(c2ccc3c(c2)[C@]2(C)CCN(CC4CC4)[C@H](C3=O)[C@@H]2C)CC1]

(28)

(2S,6R,11R)-3-(cyclopropylmethyl)-8-(4-(2-(2-(2-methoxyethoxy)ethoxy)ethyl)piperazin-1-yl)-6,11-dimethyl-3,4,5,6-tetrahydro-2,6-methanobenzo[d]azocin-1(2H)-one (28) was prepared according to the following steps

Step 1: Preparation of tert-butyl 4-(2-(2-(2-methoxyethoxy)ethoxy)ethyl)piperazine-1-carboxylate

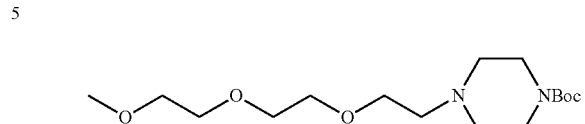

To a mixture of tert-butyl piperazine-1-carboxylate (2 g, 10.74 mmol), $K_2CO_3$ (4.45 g, 32.22 mmol) in acetone (20 mL) was charged 2-(2-(2-methoxyethoxy)ethoxy)ethyl methanesulfonate (2.86 g, 11.81 mmol). The mixture was stirred for four hours at 50° C. The reaction mass was concentrated under vacuum. The obtained crude was dissolved in EtOAc (20 mL) and washed with water (10 mL×2) and brine (10 mL). The organic layer was dried over anhydrous $Na_2SO_4$ and concentrated under vacuum to give tert-butyl 4-(2-(2-(2-methoxyethoxy)ethoxy)ethyl)piperazine-1-carboxylate (2.49 g, 70% yield) as a brown color gum.

Step 2: Preparation of 1-(2-(2-(2-methoxyethoxy)ethoxy)ethyl)piperazine

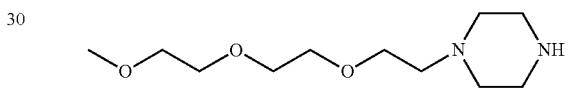

To a mixture of tert-butyl 4-(2-(2-(2-methoxyethoxy)ethoxy)ethyl)piperazine-1-carboxylate (1.0 g, 3.00 mmol) in DCM (10 mL), was added 4.0 M HCl in IPA (1 mL) at ambient temperature. The mixture was stirred for two hours, and washed with saturated $NaHCO_3$ (15 mL×2), water (10 mL×1) and brine (10 mL×1). The organic layer was dried over anhydrous $Na_2SO_4$, and concentrated under vacuum to give 1-(2-(2-(2-methoxyethoxy)ethoxy)ethyl)piperazine (0.63 g, 90% yield) as a brown gum.

Step 3: Preparation of (2S,6R,11R)-3-(cyclopropylmethyl)-8-(4-(2-(2-(2-methoxyethoxy)ethoxy)ethyl)piperazin-1-yl)-6,11-dimethyl-3,4,5,6-tetrahydro-2,6-methanobenzo[d]azocin-1(2H)-one (28)

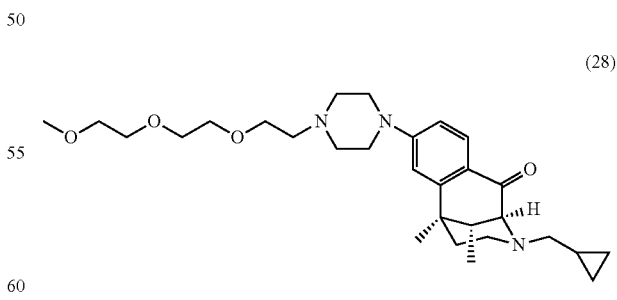

(28)

(2S,6R,11R)-3-(Cyclopropylmethyl)-6,11-dimethyl-1-oxo-1,2,3,4,5,6-hexahydro-2,6-methanobenzo[d]azocin-8-yl trifluoromethanesulfonate (200 mg, 0.479 mmol) and 1-(2-(2-(2-methoxyethoxy)ethoxy)ethyl)piperazine (122 mg, 0.527 mmol) were dissolved in toluene. BINAP (98 mg, 0.144 mmol), $Pd_2dba_3$ (88 mg, 0.096 mmol) and $Cs_2CO_3$ (219 mg, 0.671 mmol) were added to the above mixture and heated to 110° C. for two hours. The mixture was cooled to room temperature and concentrated under vacuum. A crude product was purified by column chromatography to obtain a pure (2S,6R,11R)-3-(cyclopropylmethyl)-8-(4-(2-(2-(2-methoxyethoxy)ethoxy)ethyl)piperazin-1-yl)-6,11-dimethyl-3,4,5,6-tetrahydro-2,6-methanobenzo[d]azocin-1(2H)-one (28) (124 mg, 55% yield). $^1$H NMR (500 MHz, CDCl$_3$): δ 7.8 (d, 1H), 7.70-7.65 (m, 2H), 4.05 (br, s, 1H), 3.7-3.54 (m, 10H), 3.45 (s, 3H), 3.40-3.25 (m, 8H), 2.57-2.51 (m, 4H), 2.35-2.28 (m, 4H), 2.20 (t, 2H), 1.41-1.44 (m, 3H), 1.37 (s, 3H), 0.46-0.39 (m, 2H), 0.21-0.18 (m, 1H), 0.20-0.10 (m, 2H); MS (ESI) for C$_{29}$H$_{45}$N$_3$O$_4$: 500.39 (MH$^+$). The free base was dissolved in 2 mL of 4N hydrochloride in 2-propanol. The mixture was concentrated to afford product as hydrochloride salt.

It is understood that each of Examples 1-28 described above may be modified to introduce oligomers of various lengths for each compound, as disclosed herein.

Example 29

Radioligand Competition Binding Assay

The binding affinities of certain compounds of the present invention were evaluated using radioligand binding assays in membranes prepared from CHO-K1 cells expressing recombinant human kappa (KOR) or mu (MOR) opioid receptors.

Competition binding experiments were conducted by incubating membrane protein to equilibrium in triplicate in the presence of a fixed concentration of radioligand and increasing concentrations of test compound for evaluation of binding to KOR or single concentration (10 μM) of test compound for evaluation of binding to MOR in 101 μL final volume. The radioligands used were specific for each receptor type, and the assay conditions are described in Table 1. Following incubations, the membranes were rapidly filtered through GF/B filter plate (presoaked with 0.5% polyethyleneimine), washed five times with cold 50 mM Tris-HCl, pH 7.5, and the bound radioactivity was then measured by liquid scintillation counting. Non-specific binding was measured in the presence of excess ligand; this value was subtracted from the total binding to yield the specific binding at each test concentration. Assay conditions are reported in Table 1 below.

TABLE 1

| Receptor | Receptor Source | Membrane Protein | Radioligand | K$_d$ | Non-specific binding | Methods |
|---|---|---|---|---|---|---|
| Kappa Opioid | Human recombinant in CHO-K1 cells | 2.5 μg/well | [$^3$H] Diprenorphine (1 nM) | 0.3 nM | U-50488 (10 μM) | Reaction in 50 mM Tris-HCl (pH 7.5), 5 mM MgCl$_2$, 0.05% BSA at room temperature for 1 h with shaking |
| Mu Opioid | Human recombinant in CHO-K1 cells | 5 μg/well | [$^3$H] Naloxone (4 nM) | — | Naloxone (10 μM) | Reaction in 50 mM Tris-HCl (pH 7.5), 5 mM MgCl$_2$ at room temperature for 1 h with shaking |

For KOR binding, IC$_{50}$ (concentration of test compound required to inhibit 50% of specific binding) values were obtained from non-linear regression analysis of dose-response curves, using GraphPad's Prism 5.01 software, and were calculated for those compounds that showed >50% inhibition of specific binding at the highest concentration tested. K$_i$ (affinity of test compound) was obtained using the Cheng Prusoff correction using experimental K$_d$ (affinity of radioligand) values that were previously determined under these assay conditions. For MOR binding, compounds were tested at one concentration, 10 μM, to evaluate its ability to inhibit specific radioligand binding. The values are expressed as percent inhibition of specific binding and greater than 50% inhibition of binding was considered to be significant.

With respect to determining MOR binding, an approach similar to one used for KOR binding was used.

Data are expressed as means of one experiment in triplicate determination and reported in Table 2.

TABLE 2

Binding Activities of Selected Compounds

| Compound No. (Example No.) | Kappa receptor binding | | Mu receptor % inhibition at single concentration % inhib @ 10 uM | Mu receptor binding | |
|---|---|---|---|---|---|
| | IC50 (nM) | Ki (nM) | | IC50 (nM) | Ki (nM) |
| 1 | 2682 | 618.9 | 81.9 | — | — |
| 2 | 2380 | 549.2 | 85.5 | — | — |
| 3 | 3333 | 769.2 | 80.6 | — | — |
| 4 | 879 | 202.9 | 89.2 | — | — |
| 5 | 12820 | 2959 | 51.2 | — | — |
| 6 | 6079 | 1403 | 48.6 | — | — |
| 12 | | 5.004 | | | 58.48 |
| 20 | | 2.861 | | | 44.3 |
| 23 | | 1055 | | | 7957 |
| 24 | | 493.9 | | | 1807 |
| 25 | | 955.2 | | | 3918 |
| Ketazocine | 5.6 | 1.3 | 99.2 | 8.4 | |

Ketazocine was assayed as a known kappa and mu opioid agonist. The notation "--" indicates that the assay was not performed for the referenced compounds.

Example 30 cAMP Accumulation Assay

Inhibition of cAMP accumulation by select compounds was measured in forskolin-stimulated CHO-K1 cells stably expressing KOR. CHO-K1 cells stably expressing KOR were harvested using Invitrogen Cell Dissociation Buffer, and then centrifuged at 1200 rpm for five minutes. The supernatant was aspirated and cells were resuspended in assay buffer to a density of 4×10$^5$ cells/mL. 25 μL of cells were added into a white half-area 96 well plate. Fourteen point serial dilutions of test compounds were carried out in assay buffer (PBS with 0.5 mM IBMX). Ketazocine was used as a positive control for each assay. 12.5 μL of compound was added to the cells in duplicate for each test concentration. The cells were then stimulated with 12.5 μL forskolin at a final concentration 20 μM. Cells were incubated for 45 minutes in a 37° C., 5% $CO_2$ water jacketed incubator. CisBio HTRF cAMP assay reagent was used for cAMP quantitation. Two hours after substrate addition, signal at 665/615 nm was measured using the Perkin Elmer Victor X4 HTRF reader. Data analysis was done using GraphPad Prism, sigmoidal dose-response (variable slope) curve fitting.

Using a similar approach, inhibition of cAMP accumulation by select compounds was also determined in forskolin-simulated CHO-K1 cells stably expressing MOR (wherein for this assay a density of 8×105 cells/mL was used and the positive control was DAMGO). Certain compounds of the present invention were tested as described above. Data is reported in Table 3 below.

TABLE 3

| Compound | EC50 cAMP (nM) - KOR | EC50 cAMP (nM) - MOR |
|---|---|---|
| 1 | 153 | |
| 2 | 139 | |
| 3 | 122 | |
| 4 | 9.35 | |
| 5 | 350 | |
| 6 | 357 | |
| 12 | 7 | 189.1 |
| 20 | 6.1 | 127.9 |
| 23 | 395.2 | 3288 |
| 24 | 106.8 | 597.8 |
| 25 | 195 | 1209 |
| Ketazocine | 0.55 | |

The data in Table 3 indicates that the tested compounds were effective in reducing cAMP in cells following KOR and MOR binding, indicating that the compounds function as agonists at the kappa and mu opioid receptors.

Example 31

In Situ Rat Brain Perfusion

The in situ perfusion experiment measures the relative permeability of compounds across a model of the blood-brain barrier. In situ perfusion of opioids into rat brain is performed as described in Summerfield et al., *J Pharmacol Exp Ther* 322: 205-213 (2007).

Adult male Sprague Dawley rats are used for the study. Rats are anaesthetized and the left common carotid artery is surgically cannulated for perfusion. Test compounds are perfused at concentrations of 5-50 μM in a Krebs Ringer perfusion buffer (pH 7.4). Atenolol and antipyrine are included as low and moderate permeability markers, respectively. At the end of a 30 second perfusion, the brains are removed, the left brain hemisphere is excised and homogenized. Test compounds are extracted and analyzed using LC-MS/MS. The brain permeability of the test compounds is calculated as follows:

$$P = Kin/S,$$

where P is the permeability in cm/s, Kin is the unidirectional transfer constant (ml/min/gram), and S is the luminal area of the brain vascular space.

The relative permeability as determined in the in situ brain perfusion experiment provides information regarding the rates at which compounds enter the central nervous system from the periphery. It is used to characterize and compare the degree to which compounds of the present invention penetrate the BBB as compared to known compounds or analogs of the tested compounds.

Example 32

Acetic Acid Writhing

An analgesic assay was used to determine whether a given compound can reduce and/or prevent visceral pain in mice. The assay utilizes Swiss Albino or CD-1 male mice (5-10 mice per group), each mouse being approximately 0.015-0.030 kg on the study day. Mice were treated according to standard protocols.

Mice were given a single "pretreatment" dose of a compound of the present invention, a known compound, such as diclofenac (which is a known analgesic which has been shown to reduce writhing behavior in this model), or control solution at fifteen minutes (for subcutaneous route) or thirty minutes (for orally route) prior to the administration of the acetic acid solution. The animal was given an intraperitoneal (IP) injection of an irritant (acetic acid) that induces "writhing" which may include: contractions of the abdomen, twisting and turning of the trunk, arching of the back and the extension of the hindlimbs. Mice are given a single IP injection (0.1 mL/10 g bodyweight) of a 0.5% acetic acid solution. After the injection the animals were returned to their observation enclosure and their behavior was observed. Contractions were counted between 0 and 20 minutes after the injection. The animals were used once. In certain instances, the test articles were administered at multiple doses to determine a dose response curve.

Table 4 provides the results for certain compounds of the present invention that were administered subcutaneously. Table 5 provides the results for certain compounds of the present invention that were administered orally.

TABLE 4

AAW Efficacy Following Subcutaneous Administration

| Example No. | Dose (mg/kg) | % Efficacy |
|---|---|---|
| ketazocine | 0.01 | 10.57 |
| | 0.1 | 50.03 |
| | 1 | 100.00 |
| 4 | 3 | 0.0 |
| | 10 | 39.7 |
| | 30 | 100.0 |
| 7 | 3 | 38.8 |
| | 30 | 84.8 |
| 8 | 3 | 38.0 |
| | 30 | 100.0 |
| 9 | 0.3 | 13.3 |
| | 3 | 67.8 |
| | 3 | 61.4 |
| | 10 | 95.4 |
| | 30 | 99.2 |
| 10 | 3 | 34.0 |
| | 30 | 100.0 |
| 11 | 0.3 | 21.1 |
| | 3 | 62.2 |
| | 3 | 64.3 |
| | 10 | 99.1 |
| | 30 | 100.0 |
| 12 | 3 | 68.6 |
| | 30 | 100.0 |
| 15 | 10 | 100.0 |

TABLE 4-continued

AAW Efficacy Following Subcutaneous Administration

| Example No. | Dose (mg/kg) | % Efficacy |
| --- | --- | --- |
| 16 | 10 | 26.4 |
| 13 | 10 | 40.2 |
| Step 1 of 13 | 10 | 100 |
| 17 | 10 | 23.3 |
| 14 | 10 | 13.2 |
| 18 | 10 | 31.9 |
| 19 | 10 | 31.6 |
| 20 | 10 | 88.1 |

TABLE 5

AAW Efficacy following Oral Administration

| Example No. | Dose (mg/kg) | % Efficacy |
| --- | --- | --- |
| ketazocine | 0.1 | 12.8 |
|  | 1 | 34.5 |
|  | 10 | 58.9 |
|  | 100 | 100.0 |
| 4 | 200 | 3.8 |
| 9 | 10 | 38.5 |
| 11 | 10 | 31.2 |
| 12 | 0.1 | 22.5 |
|  | 1 | 56.9 |
|  | 10 | 97.2 |
|  | 10 | 90.2 |
| 20 | 0.3 | 39.1 |
|  | 3 | 79.5 |
|  | 30 | 100.0 |

In some instances, the percent efficacy following subcutaneous administration reported in Table 4 was derived with outlier data. If the outlier data is removed, the following percent efficacy values are obtained: Compound 7 (3 mg/kg)—31.95; Compound 8 (3 mg/kg)—31.07; Compound 9 (0.3 mg/kg)—13.18, (3 mg/kg)—64.20, (3 mg/kg)—57.09 and (10 mg/kg)—94.93; Compound 10 (3 mg/kg)—26.63; Compound 11 (0.3 mg/kg)—12.30, (3 mg/kg)—56.21, (3 mg/kg)—60.30 and (10 mg/kg)—99.00; and Compound 12 (3 mg/kg)—65.09.

Example 33

Locomotor Activity

Male Swiss Albino mice were treated orally with vehicle (0.5% HPMC+0.1% Tween80), ketazocine, Compound 12 (0.3, 3 and 30 mg/kg) or Compound 20 (0.3, 3 and 30 mg/kg) thirty minutes prior to placement in the locomotor activity chamber. Total distance traveled was measured over the twenty minute observation time following placement in the locomotor activity chamber. Data are normalized relative to percent distance traveled in the vehicle group. The efficacy of Compound 12 (reported as percent distance traveled in comparison to vehicle) was 88.85%, 83.74% and 0.08% at 0.3, 3 and 30 mg/kg dosages, respectively, while the locomotor activity of Compound 20 (reported as percent distance traveled in comparison to vehicle) was 100%, 88% and 0.03% at 0.3, 3 and 30 mg/kg dosages, respectively.

What is claimed is:

1. A compound selected from the formula:

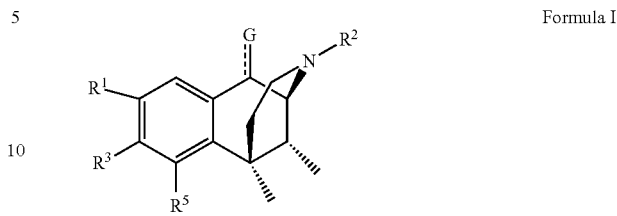

Formula I wherein:
R² is an substituted alkyl;
(i) R¹ and R³ are taken together with their intervening atoms to form a fused, substituted thiazole and R⁵ is hydrogen, where R¹ and R³ are positions 4 and 5 of the thiazole, wherein the thiazole is substituted with —X-POLY at position 2 of the thiazole; or
(ii) R³ and R⁵ are taken together with their intervening atoms to form a fused, substituted thiazole and R¹ is hydrogen, where R¹ and R³ are positions 4 and 5 of the thiazole, wherein the thiazole is substituted with —X-POLY at position 2 of the thiazole;
═ is a double bond;
G is ═O;
X is a spacer moiety selected from a covalent bond, —C(O)—, —NHC(O)—, —NH—, —CH₂CHOHCH₂NH—, and —O—;
POLY is a poly(alkylene oxide) oligomer;
or pharmaceutically acceptable salts thereof.

2. The compound of claim 1, wherein R⁵ is hydrogen.
3. The compound of claim 1, wherein R² is alkyl or cyclopropylmethyl.
4. The compound of claim 1, wherein R¹ is hydrogen.
5. The compound of claim 1, wherein the compound of Formula I is selected from the formulae:

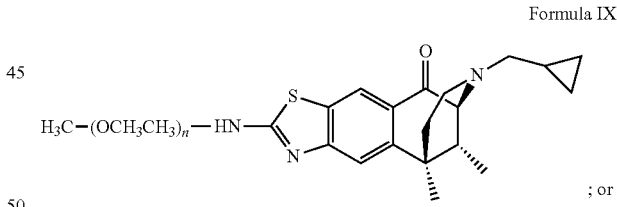

Formula IX

; or

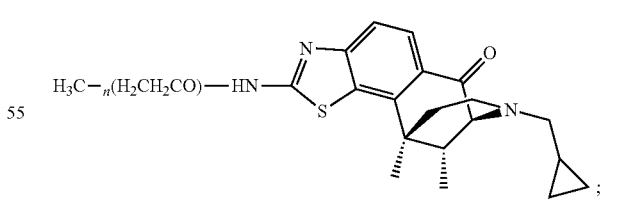

Formula XIX and
wherein n is an integer from 1 to 30.

6. The compound of claim 5, wherein n is an integer from 1 to 10.
7. The compound of claim 1, wherein R³ and R⁵ are taken together with their intervening atoms to form the substituted thiazole.

8. A compound, selected from
(6S,10R,12R)-2-(2,5,8,11,14-pentaoxahexadecan-16-ylamino)-7-(cyclopropylmethyl)-10,12-dimethyl-7,8,9,10-tetrahydro-6,10-methanothiazolo[4',5':4,5]benzo[1,2-d]azocin-5(6H)-one; and
(7S,11R,12R)-2-(2,5,8,11,14-pentaoxahexadecan-16-ylamino)-8-(cyclopropylmethyl)-11,12-dimethyl-8,9,10,11-tetrahydro-7,11-methanothiazolo[5',4':3,4]benzo[1,2-d]azocin-6(7H)-one;
or pharmaceutically acceptable salts thereof.

9. A pharmaceutical composition comprising the compound of claim 1 and at least one pharmaceutically acceptable excipient.

10. A composition of matter comprising the compound of claim 1, wherein the compound is present in a dosage form.

11. The compound of claim 1, wherein the poly(alkylene oxide) oligomer is a poly(alkylene glycol) oligomer.

* * * * *